US007745578B2

(12) United States Patent
Poznansky et al.

(10) Patent No.: US 7,745,578 B2
(45) Date of Patent: Jun. 29, 2010

(54) FUGETACTIC PROTEINS, COMPOSITIONS AND METHODS OF USE

(75) Inventors: Mark C. Poznansky, Charlestown, MA (US); Dahlia Doughty, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 319 days.

(21) Appl. No.: 10/563,726

(22) PCT Filed: Jul. 7, 2004

(86) PCT No.: PCT/US2004/021725

§ 371 (c)(1),
(2), (4) Date: Jun. 30, 2006

(87) PCT Pub. No.: WO2005/009350

PCT Pub. Date: Feb. 3, 2005

(65) Prior Publication Data

US 2006/0276389 A1 Dec. 7, 2006

Related U.S. Application Data

(60) Provisional application No. 60/485,550, filed on Jul. 7, 2003.

(51) Int. Cl.
*C07K 7/00* (2006.01)
*C07K 14/00* (2006.01)
*A61K 38/00* (2006.01)

(52) U.S. Cl. ......................... 530/328; 530/350; 514/12; 514/15

(58) Field of Classification Search ....................... None
See application file for complete search history.

(56) References Cited

U.S. PATENT DOCUMENTS

| | | | | |
|---|---|---|---|---|
| 5,750,119 A * | 5/1998 | Srivastava | ................ | 424/277.1 |
| 2003/0104622 A1 * | 6/2003 | Robbins et al. | ............. | 435/455 |

FOREIGN PATENT DOCUMENTS

| | | | |
|---|---|---|---|
| WO | WO 01/017554 | * | 3/2001 |
| WO | WO 01/52791 A2 | * | 7/2001 |

OTHER PUBLICATIONS

Wells et al., Biochemistry, vol. 29, 1990, pp. 8509-8517.*

Seffernick et al., J. of Bacteriology, Apr. 2001, pp. 2405-2410.*

Sequence alignment of instant SEQ ID No. 3 and GenBank X15183 (human HSP90) (Apr. 30, 2009).*

Yagita et al. "Molecular Cloning of a Novel Member of the HSP110 Family of Genes, Ischemia-Responsive Protein 94 kDa (irp94), Expressed in Rat Brain After Transient Forebrain Ischemia" J. of Neurochem. 72: 1544-1551 (1999).

Poznansky et al. "Thymocyte emigration is mediated by active movement away from stroma-derived factors" J. of Clin. Invest. 109(8): 1101-1110 (2002).

Shinomiya et al. "Complete Primary Structure and Phosphorylation Site of the 65-kDa Macrophage Protein Phosphorylated by Stimulation with Bacterial Lipopolysaccharide" J. of Immunol. 154: 3471-3478 (1995).

Shrikant et al. "Control of Syngeneic Tumor Growth by Activation of CD8+ T Cells: Efficacy Is Limited by Migration Away from the Site and Induction of Nonresponsiveness" J. of Immonul. 162: 2858-2866 (1999).

* cited by examiner

*Primary Examiner*—Suzanne M. Noakes
(74) *Attorney, Agent, or Firm*—Edwards Angell Palmer & Dodge LLP; Peter C. Lauro, Esq.

(57) ABSTRACT

This invention relates to compositions and methods that modulate the movement of cells with migratory capacity. More specifically, the invention relates to compositions and methods for promoting migratory movement, fugetaxis, of cells from a specific site in a subject. The foregoing are useful, inter alia, in the treatment of conditions characterized by a need to promote migratory cell movement away from specific sites in a subject. Specific sites include sites of inflammation, infection, an autoimmune reaction, a tumor and a transplanted organ or tissue.

2 Claims, 25 Drawing Sheets

FIG. 1

```
HSP 90-beta (Mouse)
SEQ ID NO:1

  1 mpeevhhgee evetfafqae iaqlmsliin tfysnkeifl relisnasda ldkiryeslt
 61 dpskldsgke lkidiipnpq ertltlvdtg igmtkadlin nlgtiaksgt kafmealqag
121 adismigqfg vgfysaylva ekvvvitkhn ddeqyawess aggsftvrad hgepigrgtk
181 vilhlkedqt eyleerrvke vvkkhsqfig ypitlyleke rekeisddea eeekgekeee
241 dkddeekpki edvgsdeedd sgkdkkkktk kikekyidqe elnktkpiwt rnpdditqee
301 ygefyksltn dwedhlavkh fsvegqlefr allfiprrap fdlfenkkkk nniklyvrrv
361 fimdscdeli peylnfirgv vdsedlplni sremlqqski lkvirknivk kclelfsela
421 edkenykkfy eafsknlklg ihedstnrrr lsellryhts qsgdemtsls eyvsrmketq
481 ksiyyitges keqvansafv ervrkrgfev vymtepidey cvqqlkefdg kslvsvtkeg
541 lelpedeeek kkmeeskakf enlcklmkei ldkkvekvti snrlvsspcc ivtstygwta
601 nmerimkaqa lrdnstmgym makkhleinp dhpivetlrq kaeadkndka vkdlvvllfe
661 tallssgfsl edpqthsnri yrmiklglgi dedevaaeep naavpdeipp legdedasrm
721 eevd

HSP 90-beta (Human)
SEQ ID NO:2

  1 mpeevhhgee evetfafqae iaqlmsliin tfysnkeifl relisnasda ldkiryeslt
 61 dpskldsgke lkidiipnpq ertltlvdtg igmtkadlin nlgtiaksgt kafmealqag
121 adismigqfg vgfysaylva ekvvvitkhn ddeqyawess aggsftvrad hgepigrgtk
181 vilhlkedqt eyleerrvke vvkkhsqfig ypitlyleke rekeisddea eeekgekeee
241 dkddeekpki edvgsdeedd sgkdkkkktk kikekyidqe elnktkpiwt rnpdditqee
301 ygefyksltn dwedhlavkh fsvegqlefr allfiprrap fdlfenkkkk nniklyvrrv
361 fimdscdeli peylnfirgv vdsedlplni sremlqqski lkvirknivk kclelfsela
421 edkenykkfy eafsknlklg ihedstnrrr lsellryhts qsgdemtsls eyvsrmketq
481 ksiyyitges keqvansafv ervrkrgfev vymtepidey cvqqlkefdg kslvsvtkeg
541 lelpedeeek kkmeeskakf enlcklmkei ldkkvekvti snrlvsspcc ivtstygwta
601 nmerimkaqa lrdnstmgym makkhleinp dhpivetlrq kaeadkndka vkdlvvllfe
661 tallssgfsl edpqthsnri yrmiklglgi dedevaaeep naavpdeipp legdedasrm
721 eevd

HSP 90-alpha (Human)
SEQ ID NO:3

  1 mpeetqtqdq pmeeeevetf afqaeiaqlm sliintfysn keiflrelis nssdaldkir
 61 yesltdpskl dsgkelhinl ipnkqdrtlt ivdtgigmtk adlinnlgti aksgtkafme
121 alqagadism igqfgvgfys aylvaekvtv itkhnddeqy awessaggsf tvrtdtgepm
181 grgtkvilhl kedqteylee rrikeivkkh sqfigypitl fvekerdkev sddeaeeked
241 keeekekeek esedkpeied vgsdeeeekk dgdkkkkkki kekyidqeel nktkpiwtrn
301 pdditneeyg efyksltndw edhlavkhfs vegqlefral lfvprrapfd lfenrkkknn
361 iklyvrrvfi mdnceelipe ylnfirgvvd sedlplnisr emlqqskilk virknlvkkc
421 lelftelaed kenykkfyeq fsknikigih edsqnrkkls ellryytsas gdemvslkdy
481 ctrmkenqkh iyyitgetkd qvansafver lrkhgleviy miepideycv qqlkefegkt
541 lvsvtkegle lpedeeekkk qeekktkfen lckimkdile kkvekvvvsn rlvtspcciv
601 tstygwtanm erimkaqalr dnstmgymaa kkhleinpdh siietlrqka eadkndksvk
661 dlvillyeta llssgfsled pqthanriyr miklglgide ddptaddtsa avteempple
721 gdddtsrmee vd
```

FIG. 1 (continued)

HSP 84 (Mouse)
SEQ ID NO:4

```
  1 mpeevhhgee evetfafqae iaqlmsliin tfysnkeifl relisnasda ldkiryeslt
 61 dpskldsgke lkidiipnpq ertltlvdtg igmtkadlin nlgtiaksgt kafmealqag
121 adismigqfg vgfysaylva ekvvvitkhn ddeqyawess aggsftvrad hgepigrgtk
181 vilhlkedqt eyleerrvke vvkkhsqfig ypitlyleke rekeisddea eeekgekeee
241 dkedeekpki edvgsdeedd sgkdkkkktk kikekyidqe elnktkpiwt rnpdditqee
301 ygefyksltn dwedhlavkh fsvegqlefr allfiprrap fdlfenkkkk nniklyvrrv
361 fimdscdeli peylnfirgv vdsedlplni sremlqqski lkvirknivk kclelfsela
421 edkenykkfy eafsknlklg ihedstnrrr lsellryhts qsgdemtsls eyvsrmketq
481 ksiyyitges keqvansafv ervrkrgfev vymtepidey cvqqlkefdg kslvsvtkeg
541 lelpedeeek kkmeeskakf enlcklmkei ldkkvekvti snrlvsspcc ivtstygwta
601 nmerimkaqa lrdnstmgym makkhleinp dhpivetlrq kaeadkndka vkdlvvllfe
661 tallssgfsl edpqthsnri yrmiklglgi dedevtaeep saavpdeipp legdedasrm
721 eevd
```

HSP 84 (Human)
SEQ ID NO:5

```
  1 mpeevhhgee evetfafqae iaqlmsliin tfysnkeifl relisnasda ldkiryeslt
 61 dpskldsgke lkidiipnpq ertltlvdtg igmtkadlin nlgtiaksgt kafmealqag
121 adismigqfg vgfysaylva ekvvvitkhn ddeqyawess aggsftvrad hgepigrgtk
181 vilhlkedqt eyleerrvke vvkkhsqfig ypitlyleke rekeisddea eeekgekeee
241 dkddeekpki edvgsdeedd sgkdkkkktk kikekyidqe elnktkpiwt rnpdditqee
301 ygefyksltn dwedhlavkh fsvegqlefr allfiprrap fdlfenkkkk nniklyvrrv
361 fimdscdeli peylnfirgv vdsedlplni sremlqqski lkvirknivk kclelfsela
421 edkenykkfy eafsknlklg ihedstnrrr lsellryhts qsgdemtsls eyvsrmketq
481 ksiyyitges keqvansafv ervrkrgfev vymtepidey cvqqlkefdg kslvsvtkeg
541 lelpedeeek kkmeeskakf enlcklmkei ldkkvekvti snrlvsspcc ivtstygwta
601 nmerimkaqa lrdnstmgym makkhleinp dhpivetlrq kaeadkndka vkdlvvllfe
661 tallssgfsl edpqthsnri yrmiklglgi dedevaaeep naavpdeipp legdedasrm
721 eevd
```

HSP 86 (Mouse)
SEQ ID NO:6

```
  1 mpeetqtqdq pmeeeevetf afqaeiaqlm sliintfysn keiflrelis nssdaldkir
 61 yesltdpskl dsgkelhinl ipskqdrtlt ivdtgigmtk adlinnlgti aksgtkafme
121 alqagadism igqfgvgfys aylvaekvtv itkhnddeqy awessaggsf tvrtdtgepm
181 grgtkvilhl kedqteylee rrikeivkkh sqfigypitl fvekerdkev sddeaeekee
241 keeekekeek esddkpeied vgsdeeeeek kdgdkkkkkk ikekyidqee lnktkpiwtr
301 npdditneey gefyksltnd weehlavkhf svegqlefra llfvprrapf dlfenrkkkn
361 niklyvrrvf imdnceelip eylnfirgvv dsedlplnis remlqqskil kvirknlvkk
421 clelftelae dkenykkfye qfskmiklgi hedsqnrkkl sellryytsa sgdemvslkd
481 yctrmkenqk hiyfitgetk dqvansafve rlrkhglevi ymiepideyc vqqlkefegk
541 tlvsvtkegl elpedeeekk kqeekktkfe nlckimkdil ekkvekvvvs nrlvtspcci
601 vtstygwtan merimkaqal rdnstmgyma akkhleinpd hsiietlrqk aeadkndksv
661 kdlvillyet allssgfsle dpqthanriy rmiklglgid eddptvddts aavteemppl
721 egdddtsrme evd
```

FIG. 1 (continued)

HSP 86, HSP 60 (Human)
SEQ ID NO:7

```
  1 mlrlptvfrq mrpvsirvlap hltrayakdv kfgadaralm lqgvdllada vavtmgpkgr
 61 tviieqswgs pkvtkdgvtv aksidlkdky knigaklvqd vanntneeag dgtttatvla
121 rsiakegfek iskganpvei rrgvmlavda viaelkkqsk pvttpeeiaq vatisangdk
181 eigniisdam kkvgrkgvit vkdgktlnde leiiegmkfd rgyispyfin tskgqkcefq
241 dayvllsekk issiqsivpa leianahrkp lviiaedvdg ealstlvlnr lkvglqvvav
301 kapgfgdnrk nqlkdmaiat ggavfgeegl tlnledvqph dlgkvgeviv tkddamllkg
361 kgdkaqiekr iqeiieqldv ttseyekekl nerlaklsdg vavlkvggts dvevnekkdr
421 vtdalnatra aveegivlgg gcallrcipa ldsltpaned qkigieiikr tlkipamtia
481 knagvegsli vekimqssse vgydamagdf vnmvekgiid ptkvvrtall daagvasllt
541 taevvvteip keekdpgmga mggmgggmgg gmf
```

L-plastin (Human)
SEQ ID NO:8

```
  1 margsvsdee mmelreafak vdtdgngyis fnelndlfka aclplpgyrv reitenlmat
 61 gdldqdgris fdefikifhg lkstdvaktf rkainkkegi caiggtseqs svgtqhsyse
121 eekyafvnwi nkalendpdc rhvipmnpnt ndlfnavgdg ivlckminls vpdtiderti
181 nkkkltpfti qenlnlalns asaigchvvn igaedlkegk pylvlgllwq vikiglfadi
241 elsrnealia llregesled lmklspeell lrwanyhlen agcnkignfs tdikdskayy
301 hlleqvapkg deegvpavvi dmsglrekdd iqraecmlqq aerlgcrqfv tatdvvrgnp
361 klnlafianl fnrypalhkp enqdidwgal egetreertf rnwmnslgvn prvnhlysdl
421 sdalvifqly ekikvpvdwn rvnkppypkl ggnmkklenc nyavelgknq akfslvgigg
481 qdlnegnrtl tlaliwqlmr rytlnileei gggqkvnddi ivnwvnetlr eaeksssiss
541 fkdpkistsl pvldlidaiq pgsinydllk tenlnddekl nnakyaisma rkigarvyal
601 pedlvevnpk mvmtvfaclm gkgmkrv
```

EL4CM24 SDS PAGE

Ion Exchange Chromatography

FIG. 12A

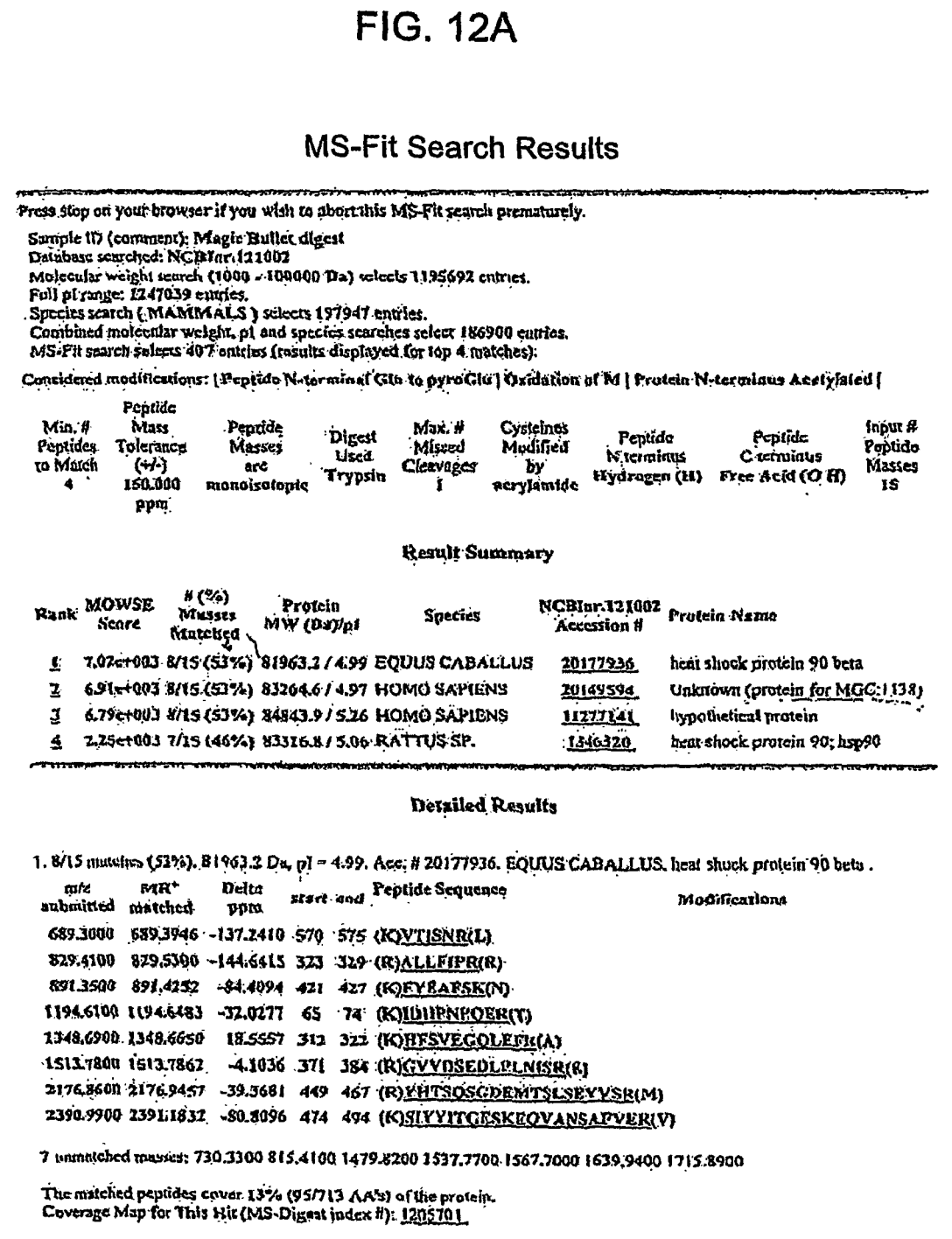

MS-Fit Search Results

Press stop on your browser if you wish to abort this MS-Fit search prematurely.

Sample ID (comment): Magic Bullet digest
Database searched: NCBInr.121002
Molecular weight search (1000 - 100000 Da) selects 1195692 entries.
Full pI range: 1247039 entries.
Species search (MAMMALS) selects 197947 entries.
Combined molecular weight, pI and species searches select 186900 entries.
MS-Fit search selects 407 entries (results displayed for top 4 matches).

Considered modifications: [ Peptide N-terminal Gln to pyroGlu | Oxidation of M | Protein N-terminus Acetylated ]

| Min. # Peptides to Match | Peptide Mass Tolerance (+/-) | Peptide Masses are | Digest Used | Max. # Missed Cleavages | Cysteines Modified by | Peptide N terminus | Peptide C terminus | Input # Peptide Masses |
|---|---|---|---|---|---|---|---|---|
| 4 | 150.000 ppm | monoisotopic | Trypsin | 1 | acrylamide | Hydrogen (H) | Free Acid (O H) | 15 |

Result Summary

| Rank | MOWSE Score | # (%) Masses Matched | Protein MW (Da)/pI | Species | NCBInr.121002 Accession # | Protein Name |
|---|---|---|---|---|---|---|
| 1 | 7.07e+003 | 8/15 (53%) | 81963.2 / 4.99 | EQUUS CABALLUS | 20177936 | heat shock protein 90 beta |
| 2 | 6.91e+003 | 8/15 (53%) | 83264.6 / 4.97 | HOMO SAPIENS | 20149594 | Unknown (protein for MGC:1138) |
| 3 | 6.79e+003 | 8/15 (53%) | 84843.9 / 5.26 | HOMO SAPIENS | 11277141 | hypothetical protein |
| 4 | 2.25e+003 | 7/15 (46%) | 83316.8 / 5.06 | RATTUS SP. | 1346320 | heat shock protein 90; hsp90 |

Detailed Results 1. 8/15 matches (53%). 81963.2 Da, pI = 4.99. Acc. # 20177936. EQUUS CABALLUS. heat shock protein 90 beta.

| m/z submitted | MH+ matched | Delta ppm | start | end | Peptide Sequence | Modifications |
|---|---|---|---|---|---|---|
| 689.3000 | 689.3946 | -137.2410 | 570 | 575 | (K)QVTISNR(L) | |
| 829.4100 | 829.5300 | -144.6415 | 323 | 329 | (R)ALLFIPR(R) | |
| 891.3500 | 891.4252 | -84.4094 | 421 | 427 | (K)EYRAFSK(N) | |
| 1194.6100 | 1194.6483 | -32.0277 | 65 | 74 | (K)IDIIPNPQER(T) | |
| 1348.6900 | 1348.6650 | 18.5557 | 312 | 322 | (K)HFSVEGQLEFR(A) | |
| 1513.7800 | 1513.7862 | -4.1036 | 371 | 384 | (R)GVVDSEDLPLNISR(E) | |
| 2176.8600 | 2176.9457 | -39.3681 | 449 | 467 | (R)YHTSQSGDEMTSLSEYVSR(M) | |
| 2390.9900 | 2391.1832 | -80.8096 | 474 | 494 | (K)SIYYITGESKEQVANSAFVER(V) | |

7 unmatched masses: 730.3300 815.4100 1479.8200 1537.7700 1567.7000 1639.9400 1715.8900

The matched peptides cover 13% (95/713 AA's) of the protein.
Coverage Map for This Hit (MS-Digest index #): 1205701

FIG. 12B 2. 8/15 matches (53%). 83164.6 Da, pI = 4.97. Acc. 20149594 HOMO SAPIENS; Unknown (protein for MGC:1138).

| m/z submitted | MH+ matched | Delta ppm | start | end | Peptide Sequence | Modifications |
|---|---|---|---|---|---|---|
| 689.3000 | 689.3946 | -137.2410 | 578 | 583 | (K)YTISNR(L) | |
| 829.4100 | 829.5300 | -144.6415 | 331 | 337 | (R)ALLFIPR(R) | |
| 891.3500 | 891.4252 | -84.4094 | 429 | 435 | (K)EYRAFSK(N) | |
| 1194.6100 | 1194.6483 | -32.0277 | 73 | 82 | (K)IDIIPNPQER(T) | |
| 1348.6900 | 1348.6650 | 18.5557 | 320 | 330 | (K)HFSVEGQLEFR(A) | |
| 1513.7800 | 1513.7862 | -4.1036 | 379 | 392 | (R)GVVDSEDLPLNISR(E) | |
| 2176.8600 | 2176.9457 | -39.3681 | 457 | 475 | (R)YHTSQSGDEMTSLSEYVSR(M) | |
| 2390.9900 | 2391.1832 | -80.8096 | 482 | 502 | (K)SIYYITGESKEQVANSAFVER(V) | |

7 unmatched masses: 730.3300 815.4100 1479.8200 1537.7700 1567.7000 1639.9400 1715.8900

The matched peptides cover 13% (95/724 AA's) of the protein.
Coverage Map for This Hit (MS-Digest index #): 137455

3. 8/15 matches (53%). 84843.9 Da, pI = 5.26. Acc. # 11277141. HOMO SAPIENS. hypothetical protein

| m/z submitted | MH+ matched | Delta ppm | start | end | Peptide Sequence | Modifications |
|---|---|---|---|---|---|---|
| 689.3000 | 689.3946 | -137.2410 | 578 | 583 | (K)YTISNR(L) | |
| 829.4100 | 829.5300 | -144.6415 | 331 | 337 | (R)ALLFIPR(R) | |
| 891.3500 | 891.4252 | -84.4094 | 429 | 435 | (K)EYRAFSK(N) | |
| 1194.6100 | 1194.6483 | -32.0277 | 73 | 82 | (K)IDIIPNPQER(T) | |
| 1348.6900 | 1348.6650 | 18.5557 | 320 | 330 | (K)HFSVEGQLEFR(A) | |
| 1513.7800 | 1513.7862 | -4.1036 | 379 | 392 | (R)GVVDSEDLPLNISR(E) | |
| 2176.8600 | 2176.9457 | -39.3681 | 457 | 475 | (R)YHTSQSGDEMTSLSEYVSR(M) | |
| 2390.9900 | 2391.1832 | -80.8096 | 482 | 502 | (K)SIYYITGESKEQVANSAFVER(V) | |

7 unmatched masses: 730.3300 815.4100 1479.8200 1537.7700 1567.7000 1639.9400 1715.8900.

The matched peptides cover 12% (95/737 AA's) of the protein.
Coverage Map for This Hit (MS-Digest index #): 1101236

4. 7/15 matches (46%) 83116.8 Da, pI = 5.06. Acc. # 1346320. RATTUS SP.. heat shock protein 90; hsp90.

| m/z submitted | MH+ matched | Delta ppm | start | end | Peptide Sequence | Modifications |
|---|---|---|---|---|---|---|
| 689.3000 | 689.3946 | -137.2410 | 578 | 583 | (K)YTISNR(L) | |
| 829.4100 | 829.5300 | -144.6415 | 331 | 337 | (R)ALLFIPR(R) | |
| 891.3500 | 891.4252 | -84.4094 | 429 | 435 | (K)EYRAFSK(N) | |
| 1348.6900 | 1348.6650 | 18.5557 | 320 | 330 | (K)HFSVEGQLEFR(A) | |
| 1513.7800 | 1513.7862 | -4.1036 | 379 | 392 | (R)GVVDSEDLPLNISR(E) | |
| 2176.8600 | 2176.9457 | -39.3681 | 457 | 475 | (K)YHTSQSGDEMTSLSEYVSR(M) | |
| 2390.9900 | 2391.1832 | -80.8096 | 482 | 502 | (K)SIYYITGESKEQVANSAFVER(V) | |

8 unmatched masses: 730.3300 815.4100 1194.6100 1479.8200 1537.7700 1567.7000 1639.9400 1715.8900

MS-Tag Search Results

Sample ID (comment): Apo A-1 1040 AKFVLEDLR
Database searched: NCBInr.121002
Full Molecular Weight range: 1347039 entries.
Full pI range: 1347039 entries.
Species search ( MAMMALS ) selects 197947 entries.
Number of sequences passing through parent mass filter: 4253
MS-Tag search selects 7 entries (results displayed for top 3 matches).

Parent mass: 1194.6100 (+/- 0.2000 Da)
Fragment Ions used in search: 175.31, 272.00, 329.20, 341.63, 355.43, 512.43, 529.50, 626.31, 713.44, 740.51, 866.33 (+/- 0.50 Da)
Ion Types Considered: a b B y p h I

| Search Mode | Max. # Unmatched Ions | Peptide Masses are | Digest Used | Max. # Missed Cleavages | Cysteines Modified by | Peptide N terminus | Peptide C terminus |
|---|---|---|---|---|---|---|---|
| identity | 1 | monoisotopic | Trypsin | 1 | acrylamide | Hydrogen (H) | Free Acid (O H) |

Result Summary

| Rank | # Unmatched Ions | Sequence | MH+ Calculated (Da) | MH+ Error (Da) | Protein MW (Da)/pI | Species | NCBInr.121002 Accession # | Protein Name |
|---|---|---|---|---|---|---|---|---|
| 1 | 0/11 | (K)IDIIPNPQER(T) | 1194.6483 | -0.0383 | 83325.7 / 4.97 | MOUSE | 123681 | Heat shock protein HSP 90-beta (HSP 84) (Tumor specific transplantation 84 kDa antigen) (TSTA) |
| 1 | 0/11 | (K)IDIIPNPQER(T) | 1194.6483 | -0.0383 | 83361.1 / 5.03 | MUS MUSCULUS | 6680305 | heat shock protein, 84 kDa 1 |
| 1 | 0/11 | (K)IDIIPNPQER(T) | 1194.6483 | -0.0383 | 14066.4 / 4.64 | HOMO SAPIENS | 2351110 | heat shock protein beta |

FIG. 12C

Detailed Results

| Rank | # Unmatched Ions | Sequence | MH+ Calculated (Da) | MH+ Error (Da) | Protein MW (Da)/pI | Species | NCBInr.121002 Accession # | MS-Digest Index # | Protein Name |
|---|---|---|---|---|---|---|---|---|---|
| | 0/11 | (K)IDILPNPQER(T) | 1194.6483 | -0.0383 | 83325.7 / 4.97 | MOUSE | 123681 | 318176 | Heat shock protein HSP 90-beta (HSP 84) (Tumor specific transplantation 84 kDa antigen) (TSTA) |
| | 0/11 | (K)IDILPNPQER(T) | 1194.6483 | -0.0383 | 83361.1 / 5.03 | MUS MUSCULUS | 6680305 | 583990 | heat shock protein, 84 kDa 1 |

| Fragment-Ion (m/z) | 175.31 | 212.00 | 229.20 | 342.62 | 355.43 | 512.43 | 529.50 | 626.31 | 723.44 | 740.58 | 966.73 |
|---|---|---|---|---|---|---|---|---|---|---|---|
| Ion-type<br>Delta Da | $y_1$<br>0.19 | NP<br>-0.10 | $b_2$<br>0.08<br>DI<br>0.08 | $b_3$<br>0.42<br>DIL<br>0.42 | PQE<br>0.27 | $y_4$-$NH_3$<br>0.18 | $y_4$<br>0.23 | $y_5$-$NH_3$<br>0.02 | $y_6$-$NH_3$<br>0.10 | $y_6$<br>0.21 | $y_8$<br>0.19 |

| Rank | # Unmatched Ions | Sequence | MH+ Calculated (Da) | MH+ Error (Da) | Protein MW (Da)/pI | Species | NCBInr.121002 Accession # | MS-Digest Index # | Protein Name |
|---|---|---|---|---|---|---|---|---|---|
| | 0/11 | (K)IDILPNPQER(T) | 1194.6483 | -0.0383 | 140664 / 4.64 | HOMO SAPIENS | 1351110 | 587097 | heat-shock protein beta |

| Fragment-Ion (m/z) | 175.31 | 212.00 | 229.20 | 342.62 | 355.43 | 512.43 | 529.50 | 626.31 | 723.44 | 740.58 | 966.73 |
|---|---|---|---|---|---|---|---|---|---|---|---|
| Ion-type<br>Delta Da | $y_1$<br>0.19 | NP<br>-0.10 | $b_2$<br>0.08<br>DI<br>0.08 | $b_3$<br>0.42<br>DII<br>0.42 | PQE<br>0.27 | $y_4$-$NH_3$<br>0.18 | $y_4$<br>0.23 | $y_5$-$NH_3$<br>0.02 | $y_6$-$NH_3$<br>0.10 | $y_6$<br>0.21 | $y_8$<br>0.19 |

MS-Tag Search Results

Sample ID (comment): Apo A-1 1040 AKPVLEDLR
Database searched: NCBInr.121002
Molecular weight search (1000 - 100000 Da) selects 1195692 entries.
Full pI range: 1147039 entries.
Species search ( MAMMALS ) selects 191947 entries.
Combined molecular weight, pI and species searches select 186900 entries.
Number of sequences passing through parent mass filter: 4989
MS-Tag search selects 18 entries (results displayed for top 3 matches).

Parent mass: 815.4100 (+/- 0.2000 Da)
Fragment Ions used in search: 185.26, 255.17, 272.34, 298.32, 354.45, 371.53, 417.39, 445.25, 518.35 (+/- 0.50 Da)

Ion Types Considered: a b B y n h I

| Search Mode | Max. # Unmatched Ions | Peptide Masses are | Digest Used | Max. # Missed Cleavages | Cysteines Modified by | Peptide N terminus | Peptide C terminus |
|---|---|---|---|---|---|---|---|
| Identity | 1 | monoisotopic | Trypsin | 1 | acrylamide | Hydrogen (H) | Free Acid (O H) |

Result Summary

| Rank | # Unmatched Ions | Sequence | MH+ Calculated (Da) | MH+ Error (Da) | Protein MW (Da)/pI | Species | NCBInr.121002 Accession # | Protein Name |
|---|---|---|---|---|---|---|---|---|
| 1 | 0/9 | (R)ALLFVPR(R) | 815.5143 | -0.1043 | 75541.0 / 5.28 | MUS MUSCULUS | 20882565 | similar to heat shock protein 86 |
| 1 | 0/9 | (R)ALLFVPR(R) | 815.5143 | -0.1043 | 84674.2 / 4.94 | HOMO SAPIENS | 123678 | 90 kDa heat-shock protein (AA 1-732) |
| 1 | 0/9 | (K)AILFVPR(R) | 815.5143 | -0.1043 | 57068.0 / 6.38 | HOMO SAPIENS | 12804541 | hypothetical protein LOC63929 |

Detailed Results

| Rank | # Unmatched Ions | Sequence | MH+ Calculated (Da) | MH+ Error (Da) | Protein MW (Da)/pI | Species | NCBInr.121002 Accession # | MS-Digest Index # | Protein Name |
|---|---|---|---|---|---|---|---|---|---|
| 1 | 0/9 | (R)ALLFVPR(R) | 815.5143 | -0.1043 | 75541.0 / 5.28 | MUS MUSCULUS | 20882565 | 615811 | similar to heat shock protein 86 |
| 1 | 0/9 | (R)ALLFVPR(R) | 815.5143 | -0.1043 | 84674.2 / 4.94 | HOMO SAPIENS | 123678 | 162860 | 90 kDa heat-shock protein (AA 1-732) |

| Fragment-Ion (m/z) | 185.26 | 255.27 | 272.34 | 298.32 | 354.45 | 371.53 | 417.39 | 445.25 | 518.35 |
|---|---|---|---|---|---|---|---|---|---|
| Ion-type<br>Delta Da | $b_2$<br>0.13 | $y_2$-$NH_3$<br>0.12 | $y_2$<br>0.17 | $b_3$<br>0.11 | $y_3$-$NH_3$<br>0.24 | $y_3$<br>0.29 | $a_4$<br>0.10 | $b_4$<br>-0.03 | $y_4$<br>0.04 |

| Rank | # Unmatched Ions | Sequence | MH+ Calculated (Da) | MH+ Error (Da) | Protein MW (Da)/pI | Species | NCBInr.121002 Accession # | MS-Digest Index # | Protein Name |
|---|---|---|---|---|---|---|---|---|---|
| 1 | 0/9 | (K)AILFVPR(R) | 815.5143 | -0.1043 | 57068.0 / 6.38 | HOMO SAPIENS | 12804541 | 171353 | hypothetical protein LOC63929 |

| Fragment-Ion (m/z) | 185.26 | 255.27 | 272.34 | 298.32 | 354.45 | 371.53 | 417.39 | 445.25 | 518.35 |
|---|---|---|---|---|---|---|---|---|---|
| Ion-type<br>Delta Da | $b_2$<br>0.13 | $y_2$-$NH_3$<br>0.12 | $y_2$<br>0.17 | $b_3$<br>0.11 | $y_3$-$NH_3$<br>0.24 | $y_3$<br>0.29 | $a_4$<br>0.10 | $b_4$<br>-0.03 | $y_4$<br>0.04 |

FIG. 13A

MS-Fit Search Results

Sample ID (comment): Magic Bullet digest
Database searched: NCBInr.51403
Molecular weight search (1000 - 200000 Da) selects 1421445 entries.
Full pI range: 1432416 entries.
Species search (HUMAN RODENT) selects 224836 entries.
Combined molecular weight, pI and species searches select 222557 entries.
MS-Fit search selects 5 entries (results displayed for top 3 matches).

Considered modifications: | Peptide N-terminal Gln to pyroGlu | Oxidation of M | Protein N-terminus Acetylated |

| Min. # Peptides to Match | Peptide Mass Tolerance (+/-) | Peptide Masses are | Digest Used | Max. # Missed Cleavages | Cysteines Modified by | Peptide N terminus | Peptide C terminus | Input # Peptide Masses |
|---|---|---|---|---|---|---|---|---|
| 7 | 150.000 ppm | monoisotopic | Trypsin | 1 | acrylamide | Hydrogen (H) | Free Acid (O H) | 13 |

Result Summary

| Rank | MOWSE Score | # (%) Masses Matched | Protein MW (Da)/pI | Species | NCBInr.51403 Accession # | Protein Name |
|---|---|---|---|---|---|---|
| 1 | 1.81e+003 | 7/13 (53%) | 94057.0 / 5.13 | RATTUS NORVEGICUS | 24025637 | ischemia responsive 94 kDa protein |
| 2 | 449 | 7/13 (53%) | 94081.1 / 5.13 | MUS MUSCULUS | 13277753 | heat shock protein 4 |
| 2 | 449 | 7/13 (53%) | 94133.1 / 5.15 | MUS MUSCULUS | 6680301 | apg-2 |

Detailed Results 1. 7/13 matches (53%). 94057.0 Da, pI = 5.13. Acc. # 24025637. RATTUS NORVEGICUS. ischemia responsive 94 kDa protein.

| m/z submitted | MH+ matched | Delta ppm | start | end | Peptide Sequence | Modifications |
|---|---|---|---|---|---|---|
| 798.5500 | 798.4514 | 123.4893 | 431 | 436 | (K)VLTKVR(K) | |
| 949.6100 | 949.5219 | 92.7425 | 62 | 69 | (K)NTVQGFKR(F) | |
| 1321.8500 | 1321.7116 | 104.7200 | 222 | 234 | (K)VLATAFDTTLGGR(K) | |
| 1402.7800 | 1402.6313 | 106.0213 | 619 | 629 | (K)NAVEEYVYEMR(D) | |
| 1495.8400 | 1495.7029 | 91.6785 | 20 | 33 | (R)AGGIETIANEYSDR(C) | |
| 1736.0700 | 1735.9271 | 82.3407 | 391 | 405 | (R)EFSITDVVPYPISLR(W) | |
| 1953.0400 | 1952.8336 | 105.6759 | 406 | 422 | (R)WNSPAEEGSSDCEVFPK(N) | |

6 unmatched masses: 915.6000 917.3600 1305.8400 1478.8800 1587.9500 1624.0500

The matched peptides cover 10% (84/840 AA's) of the protein.
Coverage Map for This Hit (MS-Digest index #): 787619

2. 7/13 matches (53%). 94081.1 Da, pI = 5.13. Acc. # 13277753. MUS MUSCULUS. heat shock protein 4.

FIG. 13B

| m/z submitted | MH+ matched | Delta ppm | start | end | Peptide Sequence | Modifications |
|---|---|---|---|---|---|---|
| 798.5500 | 798.4514 | 123.4893 | 431 | 436 | (K)VLTFYR(K) | |
| 949.6100 | 949.5219 | 92.7425 | 62 | 69 | (K)NTVQGFKR(F) | |
| 1305.8400 | 1305.7418 | 75.1849 | 670 | 680 | (K)QVYVDKLAELK(S) | |
| 1321.8500 | 1321.7116 | 104.7200 | 222 | 234 | (K)VLATAFDTTLGGR(K) | |
| 1402.7800 | 1402.6313 | 106.0213 | 620 | 630 | (K)NAVEEYVYEMR(D) | |
| 1495.8400 | 1495.7029 | 91.6785 | 20 | 33 | (R)AGGIETIANEYSDR(C) | |
| 1736.0700 | 1735.9271 | 82.3407 | 391 | 405 | (R)EFSITDVVPYPISLR(W) | |

6 unmatched masses: 915.6000 917.3600 1478.8800 1587.9500 1624.0500 1953.0400

The matched peptides cover 9% (78/841 AA's) of the protein.
Coverage Map for This Hit (MS-Digest index #): 302745.

2. 7/13 matches (53%). 94133.1 Da. pI = 5.15. Acc. # 6680301. MUS MUSCULUS. apg-2.

| m/z submitted | MH+ matched | Delta ppm | start | end | Peptide Sequence | Modifications |
|---|---|---|---|---|---|---|
| 798.5500 | 798.4514 | 123.4893 | 431 | 436 | (K)VLTFYR(K) | |
| 949.6100 | 949.5219 | 92.7425 | 62 | 69 | (K)NTVQGFKR(F) | |
| 1305.8400 | 1305.7418 | 75.1849 | 670 | 680 | (K)QVYVDKLAELK(S) | |
| 1321.8500 | 1321.7116 | 104.7200 | 222 | 234 | (K)VLATAFDTTLGGR(K) | |
| 1402.7800 | 1402.6313 | 106.0213 | 620 | 630 | (K)NAVEEYVYEMR(D) | |
| 1495.8400 | 1495.7029 | 91.6785 | 20 | 33 | (R)AGGIETIANEYSDR(C) | |
| 1736.0700 | 1735.9271 | 82.3407 | 391 | 405 | (R)EFSITDVVPYPISLR(W) | |

5 unmatched masses: 915.6000 917.3600 1478.8800 1587.9500 1624.0500 1953.0400

The matched peptides cover 9% (78/841 AA's) of the protein.
Coverage Map for This Hit (MS-Digest index #): 1179227.

FIG. 14A

MS-Fit Search Results

Sample ID (comment): Magic Bullet digest
Database searched: NCBInr.51403
Molecular weight search (1000 - 100000 Da) selects 1372760 entries.
Full pI range: 1432416 entries.
Species search ( HUMAN RODENT ) selects 224838 entries
Combined molecular weight, pI and species searches select 211465 entries.
MS-Fit search selects 335 entries (results displayed for top 3 matches).

Considered modifications: | Peptide N-terminal Gln to pyroGlu | Oxidation of M | Protein N-terminus Acetylated |

| Min. # Peptides to Match | Peptide Mass Tolerance (+/-) | Peptide Masses are | Digest Used | Max. # Missed Cleavages | Cysteines Modified by | Peptide N terminus | Peptide C terminus | Input # Peptide Masses |
|---|---|---|---|---|---|---|---|---|
| 4 | 150.000 ppm | monoisotopic | Trypsin | 1 | acrylamide | Hydrogen (H) | Free Acid (O H) | 17 |

Result Summary

| Rank | MOWSE Score | # (%) Masses Matched | Protein MW (Da)/pI | Species | NCBInr.51403 Accession # | Protein Name |
|---|---|---|---|---|---|---|
| 1 | 1.22e+005 | 11/17 (64%) | 70149.7 / 5.20 | MUS MUSCULUS | 29840803 | unnamed protein product |
| 2 | 1.22e+005 | 11/17 (64%) | 70163.8 / 5.24 | MUS MUSCULUS | 26326929 | unnamed protein product |
| 3 | 2.66e+004 | 10/17 (58%) | 70201.8 / 5.28 | MUS MUSCULUS | 6679385 | 65-kDa macrophage protein |

Detailed Results

11/17 matches (64%). 70149.7 Da, pI = 5.20. Acc. # 29840803. MUS MUSCULUS. unnamed protein product.

| m/z submitted | MH+ matched | Delta ppm | start | end | Peptide Sequence | Modifications |
|---|---|---|---|---|---|---|
| 700.4400 | 700.4146 | 36.2352 | 77 | 82 | (K)VFHGLK(S) | |
| 811.5200 | 811.4136 | 131.0872 | 585 | 591 | (K)YAISMAR(K) | |
| 942.5800 | 942.5413 | 41.0831 | 442 | 449 | (R)VNKPPVPK(L) | |
| 1069.7200 | 1069.6257 | 88.1285 | 264 | 272 | (K)LSPEELLLR(W) | |
| 1126.7200 | 1126.6373 | 73.4015 | 433 | 441 | (K)IKVPVDWNR(V) | |
| 1135.7100 | 1135.6111 | 87.0474 | 348 | 357 | (R)QEVTATDVVR(G) | |
| 1287.7700 | 1287.6268 | 111.2008 | 402 | 412 | (R)NWMNSLGVNPR(V) | |
| 1502.8900 | 1502.7525 | 91.5194 | 166 | 178 | (K)MINLSVPDTIDER(T) | |
| 1585.9400 | 1585.8477 | 58.1710 | 597 | 610 | (R)VYALPEDLVEVNPK(M) | |
| 1689.9700 | 1689.8560 | 67.4478 | 473 | 488 | (K)FSLVGIAGQDLNEGNR(T) | |
| 1758.0100 | 1757.8744 | 77.1528 | 310 | 326 | (K)GDREGIPAVVIDMSGLR(E) | |

unmatched masses: 927.5400 964.6000 1478.8800 1479.9200 1567.8600 1640.0900 he matched peptides cover 19% (120/627 AA's) of the protein.

FIG. 14B

Coverage Map for This Hit (MS-Digest index #): 372720

2. 11/17 matches (64%). 70163.8 Da, pI = 5.24. Acc. # 26326929. MUS MUSCULUS. unnamed protein product.

| m/z submitted | MH+ matched | Delta ppm | start | end | Peptide Sequence | Modifications |
|---|---|---|---|---|---|---|
| 700.4400 | 700.4146 | 36.2352 | 77 | 82 | (K)VFHGLK(S) | |
| 811.5200 | 811.4136 | 131.0872 | 585 | 591 | (K)YAISMAR(K) | |
| 942.5800 | 942.5413 | 41.0831 | 442 | 449 | (R)VNKPPYPK(L) | |
| 1069.7200 | 1069.6257 | 88.1285 | 264 | 272 | (K)LSPEELLLR(W) | |
| 1126.7200 | 1126.6373 | 73.4015 | 433 | 441 | (K)IKVPVDWNR(V) | |
| 1135.7100 | 1135.6111 | 87.0474 | 348 | 357 | (R)QFVTATDVVR(G) | |
| 1287.7700 | 1287.6268 | 111.2008 | 402 | 412 | (R)NWMNSLGVNPR(V) | |
| 1502.8900 | 1502.7525 | 91.5194 | 166 | 178 | (K)MINLSVPDTIDER(T) | |
| 1585.9400 | 1585.8477 | 58.1710 | 597 | 610 | (R)VYALPEDLVEVNPK(M) | |
| 1689.9700 | 1689.8560 | 67.4478 | 473 | 488 | (K)FSLVGIAGQDLNEGNR(T) | |
| 1758.0100 | 1757.8744 | 77.1528 | 310 | 326 | (K)GDEEGIPAVVIDMSGLR(E) | |

6 unmatched masses: 927.5400 964.6000 1478.8800 1479.9200 1567.8600 1640.0900

The matched peptides cover 19% (120/627 AA's) of the protein.
Coverage Map for This Hit (MS-Digest index #): 1174311

3. 10/17 matches (58%). 70201.8 Da, pI = 5.28. Acc. # 6679185. MUS MUSCULUS. 65-kDa macrophage protein.

| m/z submitted | MH+ matched | Delta ppm | start | end | Peptide Sequence | Modifications |
|---|---|---|---|---|---|---|
| 700.4400 | 700.4146 | 36.2352 | 77 | 82 | (K)VFHGLK(T) | |
| 811.5200 | 811.4136 | 131.0872 | 585 | 591 | (K)YAISMAR(K) | |
| 942.5800 | 942.5413 | 41.0831 | 442 | 449 | (R)VNKPPYPK(L) | |
| 1069.7200 | 1069.6257 | 88.1285 | 264 | 272 | (K)LSPEELLLR(W) | |
| 1126.7200 | 1126.6373 | 73.4015 | 433 | 441 | (K)IKVPVDWNR(V) | |
| 1135.7100 | 1135.6111 | 87.0474 | 348 | 357 | (R)QFVTATDVVR(G) | |
| 1287.7700 | 1287.6268 | 111.2008 | 402 | 412 | (R)NWMNSLGVNPR(V) | |
| 1502.8900 | 1502.7525 | 91.5194 | 166 | 178 | (K)MINLSVPDTIDER(T) | |
| 1585.9400 | 1585.8477 | 58.1710 | 597 | 610 | (R)VYALPEDLVEVNPK(M) | |
| 1758.0100 | 1757.8744 | 77.1528 | 310 | 326 | (K)GDEEGIPAVVIDMSGLR(E) | |

7 unmatched masses: 927.5400 964.6000 1478.8800 1479.9200 1567.8600 1640.0900 1689.9700

The matched peptides cover 16% (104/627 AA's) of the protein.
Coverage Map for This Hit (MS-Digest index #): 746520

FIG. 14C

MS-Tag Search Results

Sample ID (comment): Apo A-1 1040 AKPVLEDLR
Database searched: NCBInr.5.14.03
Molecular weight search (1000 - 200000 Da) selects 1421445 entries.
Full pI range: 1432416 entries.
Species search ( HUMAN RODENT ) selects 224838 entries.
Combined molecular weight, pI and species searches select 122557 entries.
Number of sequences passing through parent mass filter: 1727
MS-Tag search selects 6 entries.

Parent mass: 1287.7700 (+/- 0.2000 Da)
Fragment ions used in search: 175.00, 255.28, 272.30, 301.48, 369.37, 432.69, 542.65, 633.34, 655.97, 742.67, 840.69 (+/- 0.70 Da)

Ion Types Considered: a b B y n h

| Search Mode | Max. # Unmatched Ions | Peptide Masses are | Digest Used | Max. # Missed Cleavages | Cysteines Modified by | Peptide N terminus | Peptide C terminus |
|---|---|---|---|---|---|---|---|
| Identity | 2 | monoisotopic | Trypsin | 1 | acrylamide | Hydrogen (H) | Free Acid (O H) |

Result Summary

| Rk | # Unmatched Ions | Sequence | MH+ Calculated (Da) | MH+ Error (Da) | Protein MW (Da)/pI | Species | NCBInr.5.14.03 Accession # | Protein Name |
|---|---|---|---|---|---|---|---|---|
| 1 | 1/11 | (R)NWMNSLGVNPR(V) | 1287.6268 | 0.1432 | 70288.8 / 5.29 | HOMO SAPIENS | 8217500 | bA139H14.1 (lymphocyte cytosolic protein 1 (L-plastin)) |
| 1 | 1/11 | (R)NWMNSLGVNPR(V) | 1287.6268 | 0.1432 | 70289.7 / 5.20 | HOMO SAPIENS | 4504965 | lymphocyte cytosolic protein 1 (L-plastin) |
| 1 | 1/11 | (R)NWMNSLGVNPR(V) | 1287.6268 | 0.1432 | 70201.8 / 5.28 | MUS MUSCULUS | 6679385 | 65-kDa macrophage protein |
| 1 | 1/11 | (R)NWMNSLGVNPR(V) | 1287.6268 | 0.1432 | 32331.4 / 8.60 | MUS MUSCULUS | 12843863 | unnamed protein product |
| 1 | 1/11 | (R)NWMNSLGVNPR(V) | 1287.6268 | 0.1432 | 70163.8 / 5.24 | MUS MUSCULUS | 26326929 | unnamed protein product |
| 1 | 1/11 | (R)NWMNSLGVNPR(V) | 1287.6268 | 0.1432 | 70149.7 / 5.20 | MUS MUSCULUS | 19840803 | unnamed protein product |

Detailed Results

| Rank | # Unmatched Ions | Sequence | MH+ Calculated (Da) | MH+ Error (Da) | Protein MW (Da)/pI | Species | NCBInr.5.14.03 Accession # | MS-Digest Index # | Protein Name |
|---|---|---|---|---|---|---|---|---|---|
| 1 | 1/11 | (R)NWMNSLGVNPR(V) | 1287.6268 | 0.1432 | 70288.8 / 5.29 | HOMO SAPIENS | 8217500 | 696263 | bA139H14.1 (lymphocyte cytosolic protein 1 (L-plastin)) |
| 1 | 1/11 | (R)NWMNSLGVNPR(V) | 1287.6268 | 0.1432 | 70289.7 / 5.20 | HOMO SAPIENS | 4504965 | 725402 | lymphocyte cytosolic protein 1 (L-plastin) |
| 1 | 1/11 | (R)NWMNSLGVNPR(V) | 1287.6268 | 0.1432 | 70201.8 / 5.28 | MUS MUSCULUS | 6679385 | 746520 | 65-kDa macrophage protein |
| 1 | 1/11 | (R)NWMNSLGVNPR(V) | 1287.6268 | 0.1432 | 32331.4 / 8.60 | MUS MUSCULUS | 12843863 | 1146923 | unnamed protein product |
| 1 | 1/11 | (R)NWMNSLGVNPR(V) | 1287.6268 | 0.1432 | 70163.8 / 5.24 | MUS MUSCULUS | 16326929 | 1174311 | unnamed protein product |
| 1 | 1/11 | (R)NWMNSLGVNPR(V) | 1287.6268 | 0.1432 | 70149.7 / 5.20 | MUS MUSCULUS | 19840803 | 373720 | unnamed protein product |

| Fragment-ion (m/z) | 175.00 | 255.28 | 272.30 | 301.48 | 369.37 | 432.69 | 542.65 | 633.34 | 655.97 | 742.67 | 840.69 |
|---|---|---|---|---|---|---|---|---|---|---|---|
| Ion-type Delta Da | $y_1$ -0.12 | $y_2$-$NH_3$ 0.13 | $y_2$ 0.13 | $b_3$ 0.35 | $y_3$-$NH_3$ 0.18 | $b_4$ 0.52 | $y_4$ 0.34 | $b_5$ 0.09 | $y_6$ 0.58 | $y_7$ 0.25 | |

FIG. 15A

BLAST 2 SEQUENCES RESULTS VERSION BLASTP 2.2.4

Matrix [BLOSUM62] gap open: [11] gap extension: [1]
x_dropoff: [50] expect: [10.00] wordsize: [3] Filter ☑

Sequence 1 gi|17865718 Heat shock protein HSP 90-beta (HSP 84) (HSP 90) Length 724 (1 .. 724)
Sequence 2 gi|72223 heat shock protein 84 - mouse          Length 724 (1 .. 724)

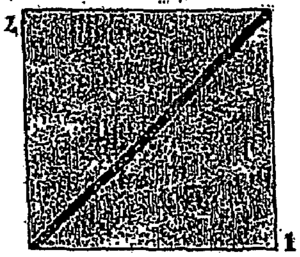

NOTE: The statistics (bitscore and expect value) is calculated based on the size of nr database

```
Score = 1178 bits (3047), Expect = 0.0
Identities = 616/724 (85%), Positives = 616/724 (85%)
```

```
Query: 1    MPXXXXXXXXXXXTFAFQAEIAQLMSLIINTFYSNKEIFLRELISNASDALDKIRYESLT 60
            MP           TFAFQAEIAQLMSLIINTFYSNKEIFLRELISNASDALDKIRYESLT
Sbjct: 1    MPEEVHHGEEEVETFAFQAEIAQLMSLIINTFYSNKEIFLRELISNASDALDKIRYESLT 60

Query: 61   DPSKLDSGKELKIDIIPNPQERTLTLVDTGIGMTKADLINNLGTIAKSGTKAFMEALQAG 120
            DPSKLDSGKELKIDIIPNPQERTLTLVDTGIGMTKADLINNLGTIAKSGTKAFMEALQAG
Sbjct: 61   DPSKLDSGKELKIDIIPNPQERTLTLVDTGIGMTKADLINNLGTIAKSGTKAFMEALQAG 120

Query: 121  ADISMIGQFGVGFYSAYLVAEKVVVITKHNDDEQYAWESSAGGSFTVRADHGEPIGRGTK 180
            ADISMIGQFGVGFYSAYLVAEKVVVITKHNDDEQYAWESSAGGSFTVRADHGEPIGRGTK
Sbjct: 121  ADISMIGQFGVGFYSAYLVAEKVVVITKHNDDEQYAWESSAGGSFTVRADHGEPIGRGTK 180

Query: 181  VILHLKEDQTEYLEERRVKEVVKKHSQFIGYPITLYLEKXXXXXXXXXXXXXXXXXXXXX 240
            VILHLKEDQTEYLEERRVKEVVKKHSQFIGYPITLYLEK
Sbjct: 181  VILHLKEDQTEYLEERRVKEVVKKHSQFIGYPITLYLEKEREKEISDDEAEEEKGEKEEE 240

Query: 241  XXXXXXXXXXXXXXXXXXXXXXXXXXXXXXXXXXXYIDQEELNKTKPIWTRNPDDITQEE 300
                                               YIDQEELNKTKPIWTRNPDDITQEE
Sbjct: 241  DKEDEEKPKIEDVGSDEEDDSGKDKKKKTKKIKEKYIDQEELNKTKPIWTRNPDDITQEE 300

Query: 301  YGEFYKSLTNDWEDHLAVKHFSVEGQLEFRALLFIPRRAPFDLFENKKKKNNIKLYVRRV 360
            YGEFYKSLTNDWEDHLAVKHFSVEGQLEFRALLFIPRRAPFDLFENKKKKNNIKLYVRRV
Sbjct: 301  YGEFYKSLTNDWEDHLAVKHFSVEGQLEFRALLFIPRRAPFDLFENKKKKNNIKLYVRRV 360

Query: 361  FIMDSCDELIPEYLNFIRGVVDSEDLPLNISREMLQQSKILKVIRKNIVKKCLELFSELA 420
```

FIG. 15B

```
             FIMDSCDELIPEYLNFIRG   SEDLPLNISREMLQQSKILKVIRKNIVKKCI    SELA
Sbjct: 361  FIMDSCDELIPEYLNFIRGVVDSEDLPLNISREMLQQSKILKVIRKNIVKKCLLLFSELA 420

Query: 421  EDKENYKKFYEAFSKNLKLGIHEDSTNRRRLSELLRYHTSQSGDEMTSLSEYVSRMKETQ 480
             EDKENYKKFYEAFSKNLKLGIHEDSTNRRRLSELLRYHTSQSGDEMTSLSEYVSRMKETQ
Sbjct: 421  EDKENYKKFYEAFSKNLKLGIHEDSTNRRRLSELLRYHTSQSGDEMTSLSEYVSRMKETQ 480

Query: 481  KSIYYITGESKEQVANSAFVERVRKRGFEVVYMTEPIDEYCVQQLKEFDGKSLVSVTXXX 540
             KSIYYITGESKEQVANSAFVERVRKRGFEVVYMTEPIDEYCVQQLKEFDGKSLVSVT
Sbjct: 481  KSIYYITGESKEQVANSAFVERVRKRGFEVVYMTEPIDEYCVQQLKEFDGKSLVSVTKEG 540

Query: 541  XXXXXXXXXXXXXXXXXXXXXNLCKLMKEILDKKVEKVTISNRLVSSPCCIVTSTYGWTA 600
                                  NLCKLMKEILDKKVEKVTISNRLVSSPCCIVTSTYGWTA
Sbjct: 541  LELPEDEEEKKKMEESKAKFENLCKLMKEILDKKVEKVTISNRLVSSPCCIVTSTYGWTA 600

Query: 601  NMERIMKAQALRDNSTMGYMMAKKHLEINPDHPIVETLRQKAEADKNDKAVKDLVVLLFE 660
             NMERIMKAQALRDNSTMGYMMAKKHLEINPDHPIVETLRQKAEADKNDKAVKDLVVLLFE
Sbjct: 601  NMERIMKAQALRDNSTMGYMMAKKHLEINPDHPIVETLRQKAEADKNDKAVKDLVVLLFE 660

Query: 661  TALLSSGFSLEDPQTHSNRIYRMIKLGLGIXXXXXXXXXXXXXXXXXXXIPPLEGDEDASRM 720
             TALLSSGFSLEDPQTHSNRIYRMIKLGLGI                   IPPLEGDEDASRM
Sbjct: 661  TALLSSGFSLEDPQTHSNRIYRMIKLGLGIDEDEVTAEEPSAAVPDEIPPLEGDEDASRM 720

Query: 721  EEVD 724
             EEVD
Sbjct: 721  EEVD 724

CPU time:     0.15 user secs.      0.06 sys. secs        0.21 total secs.

Lambda     K      H
   0.317    0.135    0.375

Gapped
Lambda     K      H
   0.267    0.0410    0.140

Matrix: BLOSUM62
Gap Penalties: Existence: 11, Extension: 1
Number of Hits to DB: 4890
Number of Sequences: 0
Number of extensions: 325
Number of successful extensions: 3
Number of sequences better than 10.0: 1
Number of HSP's better than 10.0 without gapping: 1
Number of HSP's successfully gapped in prelim test: 0
Number of HSP's that attempted gapping in prelim test: 0
Number of HSP's gapped (non-prelim): 1
length of query: 724
length of database: 405,742,523
effective HSP length: 134
effective length of query: 590
effective length of database: 405,742,389
effective search space: 239388009510
effective search space used: 239388009510
T: 9
A: 40
X1: 16 ( 7.3 bits)
X2: 129 (49.7 bits)
X3: 129 (49.7 bits)

S1: 41 (21.6 bits)
S2: 78 (34.7 bits)
```

FIG. 16A

BLAST 2 SEQUENCES RESULTS VERSION BLASTP 2.2.4

Matrix BLOSUM62 gap open: 11 gap extension: 1 x_dropoff: 50 expect: 10.00 wordsize: 3 Filter

Sequence 1 gi 72220 heat shock protein 86 - mouse Length 733 (1 .. 733)

Sequence 2 gi 72223 heat shock protein 84 - mouse Length 724 (1 .. 724)

2

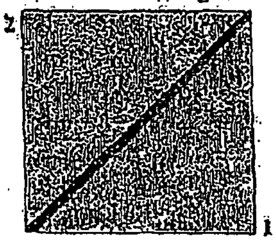

1

NOTE: The statistics (bitscore and expect value) is calculated based on the size of nr database

```
Score = 1102 bits (2851), Expect = 0.0
Identities = 561/733 (76%), Positives = 611/733 (82%), Gaps = 9/733 (1%)

Query: 1   MPEETQTQDQPMEEEEVETFAFQAEIAQLMSLIINTFYSNKEIFLRELISNSSDALDKIR 60
           MPEE          EEVETFAFQAEIAQLMSLIINTFYSNKEIFLRELISN+SDALDKIR
Sbjct: 1   MPEEVHHG-----EEVETFAFQAEIAQLMSLIINTFYSNKEIFLRELISNASDALDKIR 55

Query: 61  YESLTDPSKLDSGKELHINLIPSKQDRTLTIVDTGIGMTKADLINNLGTIAKSGTKAFME 120
           YESLTDPSKLDSGKEL I++IP+ Q+RTLT+VDTGIGMTKADLINNLGTIAKSGTKAFME
Sbjct: 56  YESLTDPSKLDSGKELKIDIIPNPQERTLTLVDTGIGMTKADLINNLGTIAKSGTKAFME 115

Query: 121 ALQAGADISMIGQFGVGFYSAYLVAEKVTVITKHNDDEQYAWESSAGGSFTVRTDTGEPM 180
           ALQAGADISMIGQFGVGFYSAYLVAEKV VITKHNDDEQYAWESSAGGSFTVR D GEP+
Sbjct: 116 ALQAGADISMIGQFGVGFYSAYLVAEKVVVITKHNDDEQYAWESSAGGSFTVRADHGEPI 175

Query: 181 GRGTKVILHLKEDQTEYLEERRIKEIVKKHSQFIGYPITLFVEKERXXXXXXXXXXXXXX 240
           GRGTKVILHLKEDQTEYLEERR+KE+VKKHSQFIGYPITL++EKER
Sbjct: 176 GRGTKVILHLKEDQTEYLEERRVKEVVKKHSQFIGYPITLYLEKEREKEISDDEAEEEKG 235

Query: 241 XXXXXXXXXXXXXXXXXXXXXXXXXXXXXXXXXXXXXXXXXXXXXXXXXXLNKTKPIWTR 300
                                                             LNKTKPIWTR
Sbjct: 236 EKEEEDKEDEEKPKIEDVGSDEEDDSGKDKKKKTKKIKEKYIDQEE----LNKTKPIWTR 291

Query: 301 NPDDITNEEYGEFYKSLTNDWEEHLAVKHFSVEGQLEFRALLFVPRRAPFDLFENRKKKN 360
           NPDDIT EEYGEFYKSLTNDWE+HLAVKHFSVEGQLEFRALLF+PRRAPFDLFEN+KKKN
Sbjct: 292 NPDDITQEEYGEFYKSLTNDWEDHLAVKHFSVEGQLEFRALLFIPRRAPFDLFENKKKKN 351

Query: 361 NIKLYVRRVFIMDNCEELIPEYLNFIRGVVDSEDLPLNISREMLQQSKILKVIRKNLVKK 420
```

FIG. 16B

```
            NIKLYVRRVFIMD+C+EL   +LNFIRGVVDSEDLPLNISREMLQQSKILKVI    +VKK
Sbjct: 352  NIKLYVRRVFIMDSCDELIHEYLNFIRGVVDSEDLPLNISREMLQQSKILKVIRKNIVKK 411

Query: 421  CLELFTELAEDKENYKKFYEQFSKNIKLGIHEDSQNRKKLSELLRYYTSASGDEMVSLKD 480
            CLELF+ELAEDKENYKKFYE FSKN+KLGIHEDS NR++LSELLRY+TS SGDEM SL +
Sbjct: 412  CLELFSELAEDKENYKKFYEAFSKNLKLGIHEDSTNRRRLSELLRYHTSQSGDEMTSLSE 471

Query: 481  YCTRMKENQKHIYFITGETKDQVANSAFVERLRKHGLEVIYMIEPIDEYCVQQLKEFEGK 540
            Y +RMKE QK IY+ITGE+K+QVANSAFVER+RK G EV+YM EPIDEYCVQQLKEF+GK
Sbjct: 472  YVSRMKETQKSIYYITGESKEQVANSAFVERVRKRGFEVVYMTEPIDEYCVQQLKEFDGK 531

Query: 541  TLVSVTKXXXXXXXXXXXXXXXXXXXXXXXXXNLCKIMKDILEKKVEKVVVSNRLVTSPCCI 600
            +LVSVT                           NLCK+MK+IL+KKVEKV +SNRLV+SPCCI
Sbjct: 532  SLVSVTKEGLELPEDEEEKKKMEESKAKFENLCKLMKEILDKKVEKVTISNRLVSSPCCI 591

Query: 601  VTSTYGWTANMERIMKAQALRDNSTMGYMAAKKHLEINPDHSIIETLRQKAEADKNDKSV 660
            VTSTYGWTANMERIMKAQALRDNSTMGYM AKKHLEINPDH I+ETLRQKAEADKNDK+V
Sbjct: 592  VTSTYGWTANMERIMKAQALRDNSTMGYMMAKKHLEINPDHPIVETLRQKAEADKNDKAV 651

Query: 661  KDLVILLYETALLSSGFSLEDPQTHANRIYRMIKLGLGIDEDDPTVDDTSAAVTEEMPPL 720
            KDLV+LL+ETALLSSGFSLEDPQTH+NRIYRMIKLGLGIDED+ T ++ SAAV +E+PPL
Sbjct: 652  KDLVVLLFETALLSSGFSLEDPQTHSNRIYRMIKLGLGIDEDEVTAEEPSAAVPDEIPPL 711

Query: 721  EGDDDTSRMEEVD 733
            EGD+D SRMEEVD
Sbjct: 712  EGDEDASRMEEVD 724

CPU time:     0.17 user secs.      0.01 sys. secs        0.18 total secs.

Lambda     K      H
   0.316    0.134    0.372

Gapped
Lambda     K      H
   0.267    0.0410    0.140

Matrix: BLOSUM62
Gap Penalties: Existence: 11, Extension: 1
Number of Hits to DB: 5349
Number of Sequences: 0
Number of extensions: 384
Number of successful extensions: 3
Number of sequences better than 10.0: 1
Number of HSP's better than 10.0 without gapping: 1
Number of HSP's successfully gapped in prelim test: 0
Number of HSP's that attempted gapping in prelim test: 0
Number of HSP's gapped (non-prelim): 1
length of query: 733
length of database: 405,742,523
effective HSP length: 134
effective length of query: 599
effective length of database: 405,742,389
effective search space: 243039691011
effective search space used: 243039691011
T: 9
A: 40
X1: 16 ( 7.3 bits)
X2: 129 (49.7 bits)
X3: 129 (49.7 bits)

S1: 41 (21.6 bits)
S2: 78 (34.7 bits)
```

FUGETACTIC PROTEINS, COMPOSITIONS AND METHODS OF USE

RELATED APPLICATIONS/PATENTS & INCORPORTAION BY REFERENCE

This application is filed under 35 U.S.C. §371 as the U.S. national phase application of International Application PCT/US04/21725, having and international filing date of Jul. 7, 2004 and designating the U.S. and claiming priority from U.S. application Ser. No. 60/485,550 filed Jul. 7, 2003, the contents of which are incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

GOVERNMENT SUPPORT

Aspects of the invention may have been made using funding from National Institutes of Health grants MGH 2238: RO1 A149757-02 and R21 A14589801. Accordingly, the Government has rights in the invention.

FIELD OF THE INVENTION

This invention relates to compositions and methods that modulate the movement of cells with migratory capacity. More specifically, the invention relates to compositions and methods for promoting migratory movement of cells away from a specific site in a subject (i.e., fugetaxis) or alternatively inhibiting such movement. The foregoing are useful, inter alia, in the treatment of conditions that would benefit from such migratory cell movement.

BACKGROUND OF THE INVENTION

Cell movement in response to specific stimuli is known to occur in prokaryotes and eukaryotes (Doetsch R N and Seymour W F., 1970; Bailey G B et al., 1985). The cell movements seen in these organisms has traditionally been classified into three types; chemotaxis or the movement of cells along a gradient towards an increasing concentration of a chemical; negative chemotaxis (or "fugetaxis") which has been described as the movement down a gradient of a chemical stimulus and chemokinesis or the increased random movement of cells induced by a chemical agent. The receptors and signal transduction pathways for the actions of specific chemotactically active compounds have been extensively defined in prokaryotic cells. Study of *E. coli* chemotaxis has revealed that a chemical which attracts the bacteria at some concentrations and conditions may also induce negative chemotaxis or "fugetaxis" at others (Tsang N et al., 1973; Repaske D and Adler J. 1981; Tisa L S and Adler J., 1995; Taylor B L and Johnson M S., 1998).

Identification and characterization of eukaryotic fugetactic polypeptides, and inhibitors thereof, could lead to the development of therapeutic agents having a specialized activity that is useful for regulating migratory cell movement.

SUMMARY OF THE INVENTION

As demonstrated herein fugetactic agents have been discovered that function to repel migratory cells away from a specific site. In certain aspects of the invention these fugetactic agents and compositions thereof are provided. In some embodiments the compositions provided herein are in effective amounts to promote fugetaxis. In other aspects of the invention anti-fugetactic agents are provided, and the compositions which comprise these anti-fugetactic agents can also be in effective amounts to inhibit fugetaxis. In other aspects of the invention methods of use of the compositions provided herein are given.

In some instances the fugetactic agents provided are heat shock proteins (HSPs). In other instances these fugetactic agents are heat shock protein-like proteins (HSPLPs). In some aspects of the invention the HSPs or HSPLPs are combined with a pharmaceutically acceptable carrier. In some aspects the HSP or HSPLP is in an effective amount to promote fugetactic activity. In some embodiments the HSP or HSPLP has a molecular weight of about 84 kDa. In other embodiments the HSP or HSPLP has a molecular weight of about 86 kDa. In still other embodiments the HSP or HSPLP has a molecular weight of about 94 kDa.

In yet other embodiments the HSPs or HSPLPs provided are members of an HSP family such as HSP60 (chaperoning, HSP70, or HSP90 families. In specific embodiments the HSP or HSPLP is a member of the hsp90 family. In some embodiments the HSP or HSPLP is HSP 90α or is HSP 90β, or variants thereof. The HSP or HSPLP proteins provided herein therefore encompass proteins encoded by amino acid sequences as set forth as SEQ ID NOs: 1-8, as well as fragments and variants thereof (FIG. 1)

HSP or HSPLP proteins provided herein also include proteins which contain any of the amino acid sequences provided herein or combinations thereof. In some embodiments the amino acid sequences are given in FIGS. 12 and 13 (Table 1). In some embodiments the amino acid sequences are those represented in FIGS. 12 and 13 (Table 1), but without either or both of the amino acid residue(s) located in each end position.

In still other embodiments the HSPs or HSPLPs are in a secreted form. In these embodiments the HSPs or HSPLPs in secreted form can contain a signal sequence or a secretory sequence. In still other embodiments the HSPs or HSPLPs are not in a secreted form. In still further embodiments the HSPs or HSPLPs contain a retention signal.

The HSPs or HSPLPs can be obtained from any cell that produces, or can be manufactured to produce, the HSPs or HSPLPs described herein. For instance, in some embodiments the HSPs or HSPLPs are from stressed or non-stressed cells. In other embodiments the cells are stromal cells. In yet other embodiments the cells are thymic stromal cells. In still other embodiments the HSPs or HSPLPs are from a tumor cell or a tumor cell line. The tumor or tumor cell line can be derived from any kind of tumor. In some embodiments the tumor or tumor cell line is a hematological tumor or a hematological tumor cell line. In yet other embodiments the hematological tumor or hematological tumor cell line is a leukemia or a lymphoma. In other embodiments the hematological tumor or hematological tumor cell line is a thymoma cell or thymoma cell line. In certain of these embodiments the thymoma cell line is EL4.

In addition to HSPs and HSPLPs, which are now found to have fugetactic activity, L-plastin has also been found to exhibit similar function. Therefore, in some aspects of the invention compositions of L-plastin which have fugetactic activity are provided. In still other aspects of the invention L-plastin-like proteins (LPLPs) with fugetactic activity are provided. Therefore, in one aspect, a pharmaceutical composition that contains an isolated L-plastin or L-plastin-like protein in an effective amount to promote fugetactic activity and a pharmaceutically acceptable carrier is provided. In some embodiments the L-plastin or LPLP has a molecular weight of about 65 kDa. In still other embodiments the L-plastin or LPLP comprises an amino acid sequence such as SEQ ID NO: 8 (FIG. 1). The L-plastin or LPLP proteins provided herein also include proteins which contain any of the amino acid sequences provided herein or combinations thereof. In some embodiments the amino acid sequences are given in FIG. 14 (Table 1). In some embodiments the amino acid sequences are those represented in FIG. 14, but without either or both of the amino acid residue(s) located in each end position.

In some embodiments the L-plastin or LPLP, provided herein, is in a secreted form. In some embodiments the secreted form of the L-plastin or LPLP comprises a signal sequence or a secretory sequence. In still other embodiments the L-plastin or LPLP can be in phosphorylated or unphosphorylated form L-plastin or LPLP can also be obtained from any cell that produces or is made to produce the protein. These cells include in some embodiments stromal cells such as thymic stromal cells. These cells in other embodiments include tumor cells or tumor cell lines. In other embodiments the tumor or tumor cell line is a hematological tumor or a hematological tumor cell line. In still other embodiments the hematological tumor or hematological tumor cell line is a leukemia or a lymphoma. In some of these embodiments the lymphoma is a thymoma. In yet other embodiments the tumor cell line is EL4.

The fugetactic agents provided herein also include cell isolates. Therefore, in one aspect of the invention a pharmaceutical composition containing an isolate as described herein in an effective amount to stimulate fugetaxis of a cell, and a pharmaceutically acceptable carrier is provided. The cell isolates can be from any cell such as a thymic stromal, tumor or tumor cell line. In some embodiments the tumor cell line can be a thymoma cell line. In some of these embodiments the thymoma cell line is EL4. Cell isolates as provided herein include any material obtained from or including a cell, which can exhibit fugetactic activity. Cell isolates therefore include supernatants, fractions, diluted supernatants and fractions and molecules (e.g. polypeptides). In some embodiments the isolate is a substantially pure polypeptide. In still other embodiments the isolate is a supernatant of the EL4 thymoma cells. In yet other embodiments the isolate is a diluted supernatant. In some of these embodiments the supernatant is diluted ten-fold.

In one aspects the cell isolate is an isolate from a thymoma cell line, wherein the isolate has fugetactic activity that is pertussis toxin inhibitable, protease degradable, and has a molecular weight of greater than about 5 kDa and is heat inactivatable. In some embodiments the fugetactic activity of the isolate can be inhibited by heat inactivation at 56° C. for one hour. In other embodiments the fugetactic activity of isolate can be inhibited by proteinase K digestion at 37° C. for one hour. In still other embodiments the isolate does not bind significantly to heparin. In yet other embodiments the isolate binds significantly to a DEAE column in the presence of 20 mM triethanolamine buffer and NaCl in a concentration lower than 0.25-0.5M. In still further embodiments the isolate is negatively charged at pH 7.5. In yet other embodiments the fugetactic activity of the isolate can be inhibited by radicicol. In yet other embodiments the fugetactic activity of the isolate is inhibited by Geldanamycin. In still other embodiments the production of the isolate by the thymoma cells can be inhibited by Brefeldin A. In still further embodiments the activity of the isolate is not significantly upregulated by heat shock at 42° C. for one hour. In certain embodiments the isolates are obtained from cells that are not undergoing significant apoptosis or necrosis. In some embodiments the isolates are obtained from a cell (e.g. a thymoma cell line such as EL4) that is greater than 95% viable.

The isolate in some embodiments has a molecular weight that is greater than about 65 kDa. In other embodiments the isolate has a molecular weight that is greater than about 80 kDa. In still other embodiments the cell isolate has a molecular weight that is greater than about 90 kDa.

In another aspect of the invention a method of promoting fugetaxis of migratory cells in a subject is provided. This method includes administering to a subject in need of such treatment a HSP, HSPLP, L-plastin or LPLP provided herein, in an amount effective to promote fugetaxis of migratory cells away from a specific site in a subject. In some embodiments the method further includes co-administering a non-fugetactic therapeutic agent. In some embodiments the non-fugetactic agent is an anti-inflammatory or an anti-allergic agent.

The migratory cells as taught herein can be any cell with migratory capacity. In some embodiments the migratory cells are hematopoietic cells. In some of these embodiments the hematopoietic cells are immune cells. In still other embodiments the immune cells are T cells. In yet other embodiments the migratory cells are cytotoxic T lymphocytes (CTLs).

The specific site of this method can be any site where the movement of migratory cells is needed. For instance, in some embodiments the specific site is a site of an inflammation. In some embodiments the specific site is a site of an autoimmune reaction. In some of these embodiments the site of an autoimmune reaction is a site at or near a joint. In yet other embodiments the specific site is a site of an allergic reaction. In still other embodiments the specific site is a medical device, prosthetic device or a transplanted organ or tissue. In some of these embodiments the medical device, prosthetic device or a transplanted organ or tissue is xenogeneic, stem-cell derived, synthetic or an allograft. In other embodiments the medical device, prosthetic device or a transplanted organ or tissue is a stent.

The compositions provided herein can be administered in any way that is effective. In some embodiments the composition is administered locally. In other embodiments the composition is administered systemically. The compositions provided herein can be administered therefore to treat local or systemic conditions. In still other embodiments the compositions can be targeted to a specific site. For instance, in some embodiments the HSP, HSPLP, L-plastin or LPLP provided herein is conjugated to a targeting molecule.

In addition to fugetactic agents, anti-fugetactic agents are also provided. In one aspect of the invention a pharmaceutical composition that contains an anti-fugetactic agent that selectively binds to any of the HSPs, HSPLPs, L-plastins or LPLPs as provided herein in an effective amount to inhibit fugetactic activity and a pharmaceutically acceptable carrier is provided. The anti-fugetactic agent can bind to any of the amino acid sequences provided herein or a portion thereof; and therefore, can bind in some aspects to proteins which comprise these amino acid sequences.

The anti-fugetactic agents provided can be any of a number of molecules that are able to selectively bind to the fugetactic agents provided and/or inhibit fugetaxis. In some embodiments the anti-fugetactic agent is an isolated peptide. In still other embodiments the anti-fugetactic agent is an antibody or an antigen-binding fragment thereof. In yet other embodiments the anti-fugetactic agent is a small molecule.

Included herein in one aspect is a method of eliciting or enhancing an immune response in a subject. This method includes administering to a subject in need of such treatment an anti-fugetactic agent provided herein in an amount effective to inhibit immune cell-specific fugetactic activity at a specific site in the subject. The method covers any site for which the inhibition of fugetaxis would be beneficial. In some embodiments the specific site is a site of an infection. In other embodiments specific site is a tumor.

The methods provided herein further cover the use of any anti-fugetactic agent. In some embodiments the anti-fugetactic agent is Geldanamycin, 17-A-GA, herbimycin A, PU3, novobiocin or radicicol. In other embodiments the anti-fugetactic agent is an agent other than a benzoquinoid ansamycin. In still other embodiments the anti-fugetactic agent is an agent other than Geldanamycin, 17-A-GA, herbimycin A, PU3, novobiocin or radicicol.

In another aspect of the invention a method of screening for an anti-fugetactic agent that modulates fugetaxis is provided. This method contains the steps of determining a control level of fugetactic activity by combining a migratory cell with an HSP, HSPLP, L-plastin or LPLP, determining a test level of fugetactic activity by combining a migratory cell with the HSP, HSPLP, L-plastin or LPLP and a candidate compound, and comparing the control and test levels of the fugetactic activity, wherein a test level that is less than a control level indicates that the candidate compound is an anti-fugetactic agent. The fugetactic agent used in the screening method can be any of the fugetactic agents described herein.

In another aspect of the invention a method of producing a polypeptide having fugetactic activity from cells (e.g. thymoma cell such as EL4 tumor cells) by culturing the cells at a density of $10^5$-$10^6$ cells/mL in hybridoma serum free medium, harvesting a supernatant from the cells filtering the harvested supernatant with a 0.2 micron filter, fractionating the filtered supernatant, and analyzing the fractions for fugetactic activity are provided. In some embodiments the cultured cells are greater than 95% viable.

In other aspects the polypeptide having fugetactic activity produced according to the method is also provided. In some embodiments the polypeptide has a molecular weight of about 84 kDa. In still other embodiments the polypeptide has a molecular weight of about 86 kDa. In yet other embodiments the polypeptide has a molecular weight of about 94 kDa. In still further embodiments the polypeptide has a molecular weight of about 65 kDa.

In still other aspects of the invention a pharmaceutical composition that contains the polypeptide produced in an effective amount to stimulate fugetaxis of cells, and a pharmaceutically acceptable carrier is provided.

In still a further aspect of the invention a method of screening for an anti-fugetactic agent that modulates fugetaxis, which includes the steps of determining a control level of fugetactic activity by combining a migratory cell with any isolate or polypeptide provided herein; determining a test level of fugetactic activity by combining a migratory cell with the isolate or the polypeptide, and a candidate compound; and comparing the control and test levels of the fugetactic activity, wherein a test level that is less than a control level indicates that the candidate compound is an anti-fugetactic agent is provided.

Another aspect of the invention is a method of promoting fugetaxis of cells in a subject, which includes the steps of administering to a subject in need of such treatment an isolate or the polypeptide provided herein, in an amount effective to promote fugetaxis of cells away from the specific site in the subject. In some embodiments the specific site is a site of inflammation. In still other embodiments the specific site is a medical device, prosthetic device or transplanted organ or tissue. In yet other embodiments the specific site is a site of an autoimmune reaction. In still other embodiments the specific site is a site of an allergic reaction.

The methods provided herein can further include in some embodiments co-administering a non-fugetactic therapeutic agent. In some embodiments the non-fugetactic therapeutic agent is an anti-inflammatory or an anti-allergic agent. Other non-fugetactic therapeutic agents are anti-cancer agents. In some other embodiments methods are provided which can further include the administration of a second fugetactic or anti-fugetactic agent.

Each of the limitations of the invention can encompass various embodiments of the invention. It is, therefore, anticipated that each of the limitations of the invention involving any one element or combinations of elements can be included in each aspect of the invention.

These and other aspects of the invention, as well as various advantages and utilities, will be more apparent with reference to the detailed description of the preferred embodiments.

BRIEF DESCRIPTION OF THE DRAWINGS

FIG. 1 describes the amino acid sequences of HSP 90 (SEQ ID NOS 1-3), HSP 84 (SEQ ID NOS 4-5), HSP 86 (SEQ ID NO: 6), HSP 60 (SEQ ID NO: 7) and L-plastin (SEQ ID NO: 8).

FIGS. 12 A to C provides the MS-Fit and MS-Tag search results of a component protein of about 84 and 86 kDa (SEQ ID NOS 9-45, 121, and 46-51, respectively in order of appearance).

FIGS. 13 A and B provides the MS-Fit search results of a component protein of about 94 kDa (SEQ ID NOS 52-72 respectively in order of appearance).

FIGS. 14 A to C provides the MS-Fit and MS-Tag search results of a component protein of about 65 kDa (SEQ ID NOS 74-106, 121 and 107-118, respectively in order of appearance).

FIGS. 15 A and B provides the sequence alignment of human HSP 90-β (SEQ ID NOS 119) and mouse HSP protein 84 (SEQ ID NOS:4).

FIGS. 16 A and B provides the sequence alignment of HSP 84 (SEQ ID NOS 4) and HSP 86 (SEQ ID NOS 120), both from the mouse.

DETAILED DESCRIPTION OF THE INVENTION

Figure 2:
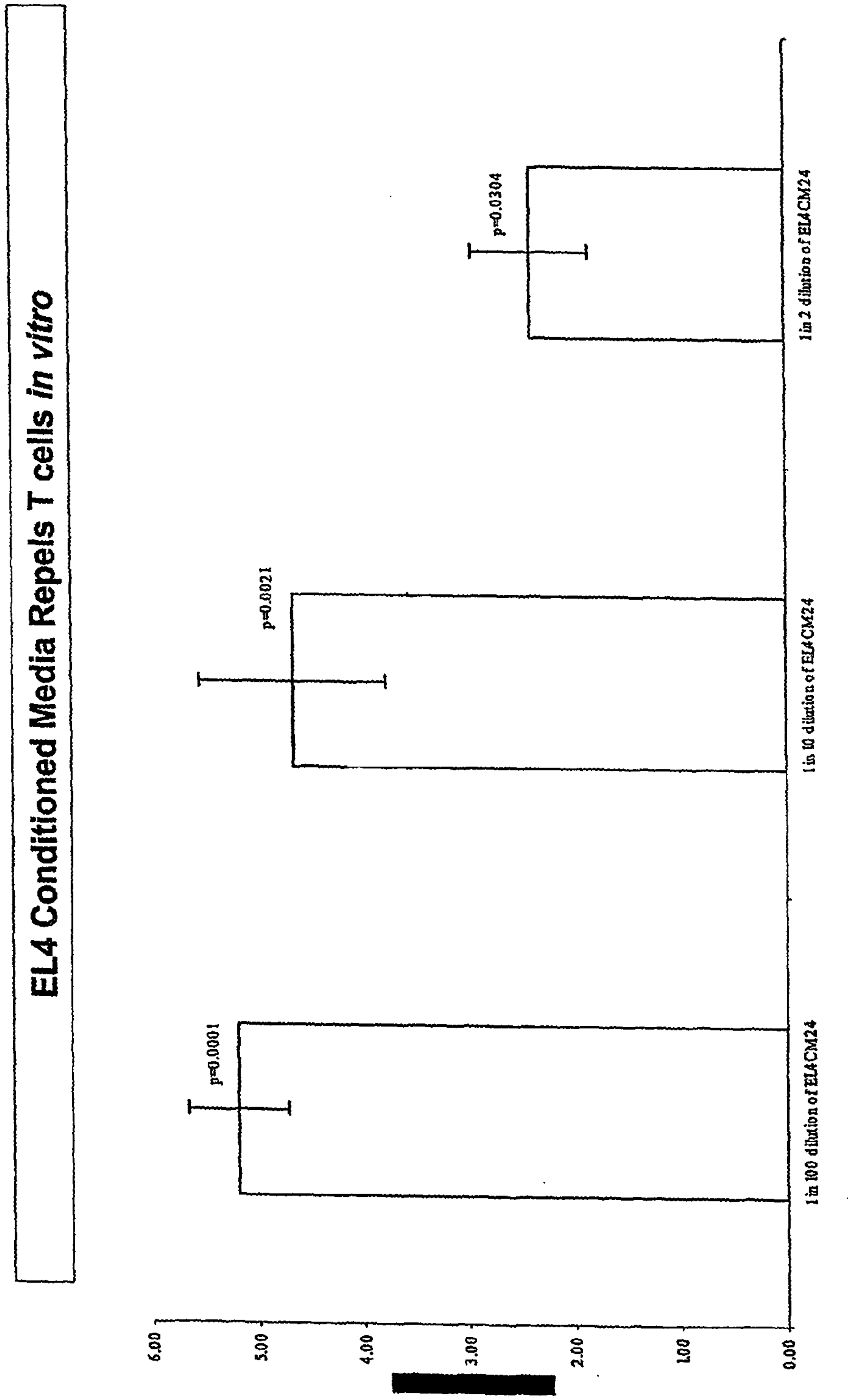
FIG. 2 provides the results of a transmigration assay using 1 in 2, 1 in 10 and 1 in 100 dilutions of EL4 24-hour conditioned media (EL4CM24).

It has now been discovered, according to the invention, that tumor cells elaborate both chemokines and other chemokinetically active substances which evoke a fugetactic or chemorepellent response from immune cells, thereby allowing the neoplastic cells to evade recognition and destruction by the host immune system. Using in vitro and in vivo assays it has now been demonstrated that culture supernatant (i.e., conditioned media) from the EL4 cell line has the ability to repel lymphocytes (i.e., to induce fugetaxis). It has been further shown that migration of lymphocytes away from EL4 24-hour conditioned media (EL4CM24) was diminished by heat inactivation and proteinase digestion of the conditioned media as well as with the use of the specific inhibitors (pertussis toxin and radicicol). Fractionation and subsequent tests on the conditioned media fractions resulted in the identification of agents which induce fugetaxis. Some of these agents show homology to heat shock proteins (HSPs) as well as L-plastin.

The present disclosure therefore provides, in part, agents with migratory cell repellent activity (hereinafter "fugetactic agents" and "fugetactic activity" or "fugetaxis"). Such agents include tumor cell isolates, heat shock proteins and L-plastin, which have now been discovered to possess fugetactic activity.

HSPs are proteins that have been found to be monoallelic and virtually intracellular (Srivastava, P., Interaction of heat shock proteins with peptides and antigen presenting cells: chaperoning of the innate and adaptive immune responses. *Annu. Rev. Immunol.* 2002. 20:395-425.) Surprisingly, this is the first demonstration that HSPs exist extracellularly and more importantly that they possess fugetactic activity. Prior to the present disclosure, HSPs were thought to be found extracellularly only as a result of necrosis. HSPs are involved in stress response, protein folding, protein degradation, control of mutant expression, regulation of transcription, differentiation, cell death, and chaperoning a wide array of peptides, such as antigenic peptides. HSPs are further thought to be involved in immune responses through the stimulation of inflammatory cytokine secretion, involvement in the MHC I and II pathways and the mediation of immune cell maturation (Srivastava, P., et al., Heat shock proteins: the 'Swiss Army Knife' vaccines against cancers and infectious agents. *Vaccine.* 19 (2001). 2590-2597.) Fugetactic activity of HSPs has not yet been described. Not bound by any particular theory, it is thought that the fugetactic activity of HSPs could be through the direct fugetactic activity of these proteins or their indirect action through the presentment or sequestration of fugetactic cytokines or chemokines.

Although, HSPs were originally recognized in cells that were heat-shocked, HSPs are also expressed in cells under normal conditions. However, it is commonly observed that under stressed conditions (e.g., heat exposure, toxin exposure, glucose deprivation, etc.), HSPs levels can be highly induced (Srivastava, P., Interaction of heat shock proteins with peptides and antigen presenting cells: chaperoning of the innate and adaptive immune responses. *Annu. Rev. Immunol* 2002. 20:395-425.) Examples of these proteins, just to name a few, include HSP 27 kDa protein (Accession No. NP_001532), HSP 70 kDa protein (Accession No. P08107), HSP 60 kDa protein (chaperonin) (Accession No. NP_002147), cardiovascular HSP (Accession No. CAB86671), HSP apg-1 (Accession No. AAp44471) and HSP (110 family) (Accession No. NP_055093). Other heat shock proteins are well known in the art or can be easily discovered. Not only are HSP members within HSP families quite homologous, but HSPs between species have also been found to exhibit significant homology. For instance, rat ischemia-responsive protein 94 kDa (irp94), which is a member of the HSP110 family, was found to be greater than 90% identical to mouse heat shock protein 4, apg-2 (Accession No. AAH03770) and human HSP70RY (Accession No. NP_705893) (Yagita, Y., et al., Molecular cloning of a novel member of the HSP110 family of genes, ischemia-responsive protein 94 kDa (irp94), expressed in rat brain after transient forebrain ischemia. *J. Neurochem.* 1999. 72(4): 1544-51.) Additionally, it was found that irp94 was greater than 60% identical to other HSP110 family members. A homology study presented in FIG. 15 shows that human HSP90β and mouse HSP84 are approximately 85% identical. Mouse HSPs 84 and 86 have also shown significant homology (FIG. 16). An analysis of these sequences showed that they are approximately 76% identical.

HSPs are intended to encompass proteins that belong to any of the HSP families. Examples of HSP families include, but are not limited to, the HSP60 (chaperonin), HSP70, and HSP90 families. In specific embodiments, HSPs of the invention include SEQ ID NOs: 1-7 (FIG. 1). HSPs may also simply be variants of HSPs that contain a secretory or signal sequence that facilitates their secretion outside a cell. In a specific embodiment, the HSP is a secreted variant of HSP 90β. HSPs also encompass HSPs that have a retention signal.

The fugetactic agents provided herein may also be heat shock protein-like proteins (HSPLPs). HSPLPs are proteins with homology to heat shock proteins (HSPs) or that exhibit similar structural characteristics and functions as heat shock proteins. These functions include functions traditionally associated with HSPs but also include functions, such as fugetactic activity, as provided herein. These proteins may be secreted from tumor or other cells.

The fugetactic agents, provided herein, also include L-plastin proteins. One of the proteins that has now been identified to exhibit fugetactic activity is a protein that is approximately 65 kDa and exhibits homology to L-plastin. L-plastin is a polypeptide found in cells of the hematopoietic system (Shinomiya, H., et al., Complete primary structure and phosphorylation site of the 65-kDa macrophage protein phosphorylated by stimulation with bacterial lipopolysaccharide. *The Journal of Immunology.* 1995. 154: 3471-3478.) Because the function of L-plastin can be modulated by phosphorylation, the L-plastins described herein can be in phosphorylated or unphosphorylated form. L-plastin proteins, like HSPs, are quite homologous. The murine and human forms of L-plastin have been found to be greater than 95% identical (Shinomiya, H., et al., Complete primary structure and phosphorylation site of the 65-kDa macrophage protein phosphorylated by stimulation with bacterial lipopolysaccharide. *The Journal of Immunology*. 1995. 154: 3471-3478. Also L-plastin has been found to have Ca2+ binding sites as well as an actin binding domain. In fact, L-plastin has also been found to act on β-actin in a $Ca^{2+}$-dependent fashion. L-plastin is also thought to have a calmodulin binding site.

Fugetactic agents also include L-plastin like proteins (LPLPs). Such proteins are proteins that exhibit homology to L-plastin (FIG. 1, SEQ ID NO:8) or proteins that exhibit structural and functional characteristics similar to L-plastin.

Homology between proteins can be determined in terms of the amino acid sequence or nucleic acid sequence of the protein. In certain embodiments, the amino acid sequences of homologous proteins are greater than about 30% identical. In other embodiments, the homologous proteins have amino acid sequences that are greater than about 40%, 50%, 60%, 70%, 80%, 90% or 95% identical. In yet other embodiments, the homologous proteins are encoded by nucleic acid molecules that are at least about 10% identical. In still other embodiments the nucleic acid molecules are at least about 20%, 30%, 40%, 50%, 60%, 70%, 80%, 90% or 95% identical. In still other embodiments the nucleic acid molecules are at least about 95% or 99% identical. Homology can be calculated using various, publicly available software tools well known to one of ordinary skill in the art. Exemplary tools include the BLAST system available from the website of the National Center for Biotechnology Information (NCBI) at the National Institutes of Health.

Another method of identifying homologous nucleotide sequences is via nucleic acid hybridization. In some embodiments, the nucleic acid hybridization is carried out under high stringency conditions. Identification of related sequences can also be achieved using polymerase chain reaction (PCR) and other amplification techniques suitable for cloning related nucleic acid sequences.

The term "high stringency conditions" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

The fugetactic agents provided also include tumor cell isolates, which may be derived from tumor cells or cell lines or from the culture supernatant in which such cells are grown. The fugetaxis-promoting tumor cell isolates can be derived from any tumor cell or cell line. A "tumor cell isolate" is any material that contains or originates from a tumor cell or cell line. The tumor cell isolate, therefore, includes supernatants, fractions of the supernatants, diluted supernatants and fractions as well as isolated molecules (e.g. polypeptides) from the tumor cell or cell line. The tumor cell isolates can be derived from thymoma cells, such as EL4 thymoma cells, but they are not so limited. Tumor cell isolates can be derived from any thymoma cell line. Such thymoma cell lines include BW5147.3 (ATCC No. TIB-47), BW5147.G.1.4 (ATCC No. TIB-48), WEHI 7.1 (ATCC No. TIB-53), WEHI 22.1 (ATCC No. TIB-54). Tumor cell isolates can also be derived from any tumor cell or tumor cell line. For example, these include cells of a melanoma, lymphoma, T cell lymphoma, B cell lymphoma, hepatoma, sarcoma, fibrosarcoma or mastocytoma. Other examples of tumor cells are provided herein below. In some embodiments, these tumors or tumor cell lines have been found to express HSPs and L-plastin. In other instances, the tumor cells are non-stressed or stressed cells. In still other instances, the cells from which the fugetactic agents are obtained are not undergoing significant apoptosis or necrosis. In still further, embodiments these cells are greater than 95% viable.

The fugetactic agents provided also include stromal-cell or stromal cell line isolate. Stromal cells are found in loose connective tissue. Stromal-cells may readily be derived from organs, that include, but are not limited to, skin, liver, pancreas, bone marrow, lymph node, thymus, kidney, CNS, brain, etc., using methods known in the art such as those discussed above. Such cells include, but are not limited to, endothelial cells, pericytes, macrophages, monocytes, plasma cells, mast cells, adipocytes, etc. In one example, stromal cells of hematopoietic tissue, including but not limited to, fibroblasts, endothelial cells, macrophages/monocytes, adipocytes and reticular cells, could be used to inoculate a tissue culture dish and/or a three-dimensional matrix. In some embodiments the isolates are thymic stromal cell isolates derived from thymic stromal cells or thymic stromal cell lines.

Thus, the invention provides fugetactic agents from tumor cells or cell lines. Preferably, these fugetactic agents are secreted from the tumor cells or cell lines, and thus can be obtained from the culture supernatant of these cells. Alternatively, the fugetactic agents may also be obtained from the cells themselves, presumably in a membrane bound form or an intracellular form.

The invention further provides pharmaceutical compositions and methods of use for these fugetactic agents (e.g., the tumor cell isolates, HSPs, HSPLPs, L-plastin and LPLPs). Pharmaceutical compositions and methods of use for inhibitors of these fugetactic agents are also provided by the invention. The foregoing can be used, inter alia, in the treatment of conditions characterized by inappropriate migratory cell movement from specific sites in a subject.

"Fugetactic activity" or "fugetaxis" refers to the ability of an agent to repel (or chemorepel) a eukaryotic cell with migratory capacity (i.e., a cell that can move away from or towards a stimulus). Accordingly, an agent with fugetactic activity is a "fugetactic agent." Such activity can be detected and measured using any of the transmigration systems described herein (see Examples), or a variety of other systems known in the art (see, e.g., U.S. Pat. No. 5,514,555, entitled: "Assays and Therapeutic Methods Based on Lymphocyte Chemoattractants" issued May 7, 1996, to Springer, T A, et al.).

The fugetactic agents of the invention are capable of repelling cells with migratory capacity and in particular hematopoietic cells, such as immune cells. Even more particularly the migratory cells are T cells. The fugetactic agents of the invention are useful in conditions where inhibition of migration of immune cells to a specific site is desirable. Many of these conditions are associated with an inflammatory response. Inhibitors of the fugetactic agents of the invention are conversely useful in conditions where promotion of migration of immune cells to a specific site is desirable. These latter conditions include but are not limited to tumors and infections. Preferably, the fugetactic agents of the invention are peptides or proteins.

The fugetactic agents of the invention can have a molecular weight of about 50 kDa, 55 kDa, 60 kDa, 65 kDa, 70 kDa, 75 kDa, 80 kDa, 85 kDa, 90 kDa, 95 kDa, 100 kDa, 105 kDa, 110 kDa, 115 kDa, 120 kDa, 125 kDa, 130 kDa, 135 kDa, 140 kDa, 145 kDa or 150 kDa, etc. In some instances the fugetactic agent has a molecular weight of about 65 kDa, 84 kDa, or about 86 kDa or about 94 kDa.

Proteins or polypeptides of the invention, are optionally recombinant, including whole proteins, partial proteins (e.g., domains) and peptide fragments. Fragments of a polypeptide preferably are those fragments that retain the distinct functional capability of the particular protein, which in this case is fugetactic activity. Such polypeptides can also comprise, for example, fusion proteins and chimeric proteins. Short polypeptides can be synthesized chemically using well-established methods of peptide synthesis.

The invention also contemplates the use of HSP, HSPLP, L-plastin and LPLP variants. As used herein, a "variant" of a polypeptide is a polypeptide which contains one or more modifications to the primary amino acid sequence, including truncations and deletions. Variants would include allelic variants and polymorphic variants having conserved function. Modifications which create a polypeptide variant can also be made to 1) enhance a property of a polypeptide, such as protein stability in an expression system or the stability of protein-protein binding; or 2) to provide a novel activity or property to a polypeptide, such as addition of a detectable moiety. Modifications to a polypeptide can be introduced by way of the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence.

The skilled artisan will also realize that conservative amino acid substitutions may be made in the neuronal differentiation factors described above to provide functionally equivalent variants of the foregoing polypeptides, i.e., the variants retaining functional capabilities. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York.

Conservative amino-acid substitutions in amino acid sequences typically are made by alteration of the coding nucleic acid encoding. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a coding gene. Where amino acid substitutions are made to a small peptide fragment, the substitutions can be made by directly synthesizing the peptide. The activity of functionally equivalent fragments of polypeptides can be tested by cloning the gene encoding the altered polypeptide into a bacterial or mammalian expression vector, introducing the vector into an appropriate host cell, expressing the altered polypeptide, and testing for a functional capability. Peptides which are chemically synthesized can be tested directly for function.

As stated above, fugetactic agents include tumor cell isolates, e.g. a thymoma cell isolate, with fugetactic activity. The tumor cell isolate may be derived from any tumor type. In one embodiment, the isolate is derived from the culture supernatant of a thymoma cell, such as the EL4 thymoma cell line. The tumor cell isolate preferably is protease sensitive and heat inactivatable. In other embodiments the fugetactic activity of the isolate can be inhibited by heat inactivation at 56° C. for one hour. In yet other embodiments, the fugetactic activity of the isolate can be inhibited by proteinase K digestion at 37° C. for one hour. In still other embodiments, the fugetactic activity of the isolate can be inhibited by pertussis toxin treatment. In still other embodiments, the fugetactic activity of the isolate can be inhibited by radicicol. In yet other embodiments, the fugetactic activity of the isolate can be inhibited by Geldanamycin. Further in some instances, the isolate does not bind significantly to heparin. In yet other instances, the isolate binds significantly to a DEAE column in the presence of 20 mM triethanolamine buffer and NaCl in a concentration lower than 0.25-0.5 M. In still further embodiments, the isolate is negatively charged at pH 7.5. In other embodiments, the production of the isolate by the thymoma cells can be inhibited by Brefeldin A. In still further embodiments, inhibition by Brefeldin A is produced by Brefeldin A treatment at 10 μg/mL final concentration. In another embodiment the activity of the isolate is not significantly upregulated by heat shock at 42° C. for one hour. In further particular embodiments, the cell isolate from the EL4 cell line has a molecular weight greater than about 5 kDa. The cell isolate can also have a molecular weight greater than about 20 kDa, 30 kDa, 40 kDa, 50 kDa, 60 kDa, 70 kDa, 80 kDa, 90 kDa, 100 kDa, 110 kDa, 120 kDa, 130 kDa, etc. More specifically, the cell isolate can have a molecular weight of about 60 kDa, 65 kDa, 70 kDa, 75 kDa, 80 kDa, 85 kDa, 90 kDa, 95 kDa, 100 is kDa, 105 kDa, 110 kDa, 115 kDa, 120 kDa, 125 kDa, 130 kDa, 135 kDa, 140 kDa, 145 kDa or 150 kDa, etc. Even more specifically, the cell isolate has a molecular weight of about 65 kDa, 84 kDa, 86 kDa or 94 kDa. In preferred embodiments, the cell isolate comprises a polypeptide, and it is this polypeptide that repels immune cells. In some instances, this polypeptide is an HSP, HSPLP, L-plastin or LPLP, and it is this HSP, HSPLP, L-plastin or LPLP that repels immune cells.

As used herein with respect to tumor cell isolates, "isolate (i.e. isolated)" means separated from its native environment and present in sufficient quantity to permit its identification or use. Isolated, when referring to a protein or polypeptide, means, for example: (i) selectively produced by expression cloning or (ii) partially purified as by chromatography or electrophoresis. Isolated proteins or polypeptides may, but need not be, substantially pure. In certain embodiments of the present invention the thymoma cell isolate is a substantially pure polypeptide. The term "substantially pure" means that the protein(s) or polypeptide(s) is essentially free of other substances with which it (they) may be found in nature or in vitro systems, to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from many of the substances with which it may be associated in living systems, i.e. isolated from certain other proteins.

As stated above, the fugetactic agents include HSPs and L-plastin. These proteins have been discovered to possess fugetactic activity, according to the invention. It has been discovered that eluted fractions of an EL4 24-hour conditioned medium (EL4CM24) comprise proteins having amino acid sequences in common with HSPs and L-plastin. These amino acid sequences are provided in FIGS. 12-14. Therefore, the fugetactic agents provided herein include proteins, which include the amino acid sequences depicted in FIGS. 12-14 (set forth as SEQ ID NOs:9-118, which may or may not include both end residues). Fugetactic agents also include proteins which comprise a portion of these sequences. The fugetactic agents of the invention, therefore, can comprise an amino acid sequence that is any one of SEQ ID NOs:1-8. The fugetactic agents of the invention can be HSP90α (FIG. 1, SEQ ID NO:3), HSP90β (FIG. 1, SEQ ID NOs:1 and 2) or L-plastin (FIG. 1, SEQ ID NO:8).

TABLE 1

| Peptide Sequence | Fig. No. |
|---|---|
| (K)VTISNR(L)<br>SEQ ID NO: 9 | 12 |
| (R)ALLFIPR(R)<br>SEQ ID NO: 10 | 12 |
| (K)FYEAFSK(N)<br>SEQ ID NO: 11 | 12 |
| (K)IDIIPNPQER(T)<br>SEQ ID NO: 12 | 12 |
| (K) HFSVEGQLEFR(A)<br>SEQ ID NO: 13 | 12 |
| (R)GVVDSEDLPLNISR(E)<br>SEQ ID NO: 14 | 12 |
| (R)YHTSQSGDEMTSLSEYVSR(M)<br>SEQ ID NO: 15 | 12 |
| (K)SIYYITGESKEQVANSAFVER(V)<br>SEQ ID NO: 16 | 12 |
| (K)VTISNR(L)<br>SEQ ID NO: 17 | 12 |
| (R)ALLFIPR(R)<br>SEQ ID NO: 18 | 12 |
| (K)FYEAFSK(N)<br>SEQ ID NO: 19 | 12 |
| (K)IDIIPNPQER(T)<br>SEQ ID NO: 20 | 12 |
| (K)HFSVEGQLEFR(A)<br>SEQ ID NO: 21 | 12 |
| (R)GVVDSEDLPLNISR(E)<br>SEQ ID NO: 22 | 12 |
| (R)YHTSQS-DEMTSLSEYVSR(M)<br>SEQ ID NO: 23 | 12 |
| (K)SIYYITGESEQVANSAFVERV<br>SEQ ID NO: 24 | 12 |

TABLE 1-continued

| Peptide Sequence | Fig. No. |
|---|---|
| (K)VTISNR(L)<br>SEQ ID NO: 25 | 12 |
| (R)ALLFVPR(R)<br>SEQ ID NO: 26 | 12 |
| (K)FYEAFSK(N)<br>SEQ ID NO: 27 | 12 |
| (K)IDILPNPQER(T)<br>SEQ ID NO: 28 | 12 |
| (K)HESVEGQLEFR(A)<br>SEQ ID NO: 29 | 12 |
| (R)GVVDSEDLPLNISR(E)<br>SEQ ID NO: 30 | 12 |
| (R)YHTSQSGDEMTSLSEYVSR(M)<br>SEQ ID NO: 31 | 12 |
| (K)SIYYITGESKEQVANSAFVER(V)<br>SEQ ID NO: 32 | 12 |
| (K)VTISNR(L)<br>SEQ ID NO: 33 | 12 |
| (R)ALLFIPR(R)<br>SEQ ID NO: 34 | 12 |
| (K)FYEAFSK(N)<br>SEQ ID NO: 35 | 12 |
| (K)HFSVEGQLEFR(A)<br>SEQ ID NO: 36 | 12 |
| (R)GVVDSEDLPLNISR(E)<br>SEQ ID NO: 37 | 12 |
| (R)YMTSQSGDEMTSLSEYVSR(M)<br>SEQ ID NO: 38 | 12 |
| (K)SIYYITGESKEQVANSAPVER(V)<br>SEQ ID NO: 39 | 12 |
| (K)IDILPNPQER(T)<br>SEQ ID NO: 40 | 12 |
| (K)IDILPNPQER(T)<br>SEQ ID NO: 41 | 12 |
| (K)IDIIPNPQER(T)<br>SEQ ID NO: 42 | 12 |
| (K)IDILPNPQER(T)<br>SEQ ID NO: 43 | 12 |
| (K)IDILPNPQER(T)<br>SEQ ID NO: 44 | 12 |
| (K)IDIIPNPQER(T)<br>SEQ ID NO: 45 | 12 |
| (R)ALLFVPR(R)<br>SEQ ID NO: 46 | 12 |
| (R)ALLFYPR(R)<br>SEQ ID NO: 47 | 12 |
| (K)AILFVPR(R)<br>SEQ ID NO: 48 | 12 |
| (R)ALLFVPR(R)<br>SEQ ID NO: 49 | 12 |

TABLE 1-continued

| Peptide Sequence | Fig. No. |
|---|---|
| (R)ALLFVPR(R) SEQ ID NO: 50 | 12 |
| (K)AILFVPR(R) SEQ ID NO: 51 | 12 |
| (K)VLTFYR(K) SEQ ID NO: 52 | 13 |
| (K)NTVQGFKR(F) SEQ ID NO: 53 | 13 |
| (K)VLATAFDTTLGGR(K) SEQ ID NO: 54 | 13 |
| (K)NAVEEYVYEMR(D) SEQ ID NO: 55 | 13 |
| (R)AGGIETIANEYSDR(C) SEQ ID NO: 56 | 13 |
| (R)EFSITDVVPYYISLR(W) SEQ ID NO: 57 | 13 |
| (R)WNSPAEEGSSDCEVFPK(N) SEQ ID NO: 58 | 13 |
| (K)VLTFYR(K) SEQ ID NO: 59 | 13 |
| (K)NTVQGFKR(F) SEQ ID NO: 60 | 13 |
| (K)QVYVDKLAELK(S) SEQ ID NO: 61 | 13 |
| (K)VLATAFDTTLGGR(K) SEQ ID NO: 62 | 13 |
| (K)NAVEEYVYEMR(D) SEQ ID NO: 63 | 13 |
| (R)AGGIETIANEYSDR(C) SEQ ID NO: 64 | 13 |
| (R)EFSITDVVPYPISLR(W) SEQ ID NO: 65 | 13 |
| (K)VLTFYR(K) SEQ ID NO: 66 | 13 |
| (K)NTVQGFKR(F) SEQ ID NO: 67 | 13 |
| (K)QVYVDKLAELK(S) SEQ ID NO: 68 | 13 |
| (K)VLATAFDTTIGGR(K) SEQ ID NO: 69 | 13 |
| (K)NAVEEYVYEMR(D) SEQ ID NO: 70 | 13 |
| (R)AGGIETIANEYSDR(C) SEQ ID NO: 71 | 13 |
| (R)EFSITDVVPYPISLR(W) SEQ ID NO: 72 | 13 |
| (K)VFHGLK(S) SEQ ID NO: 74 | 14 |
| (K)YAISMAR(K) SEQ ID NO: 75 | 14 |

TABLE 1-continued

| Peptide Sequence | Fig. No. |
|---|---|
| (R)VNKPPVPK(L) SEQ ID NO: 76 | 14 |
| (K)LSPEELLLR(W) SEQ ID NO: 77 | 14 |
| (K)IKVPVDWNR(V) SEQ ID NO: 78 | 14 |
| (R)QFVTATDVVR(G) SEQ ID NO: 79 | 14 |
| (R)NWMSLGVNPR(V) SEQ ID NO: 80 | 14 |
| (K)MINLSVPDTIDER(T) SEQ ID NO: 81 | 14 |
| (R)VYALPEDLVEVNPK(M) SEQ ID NO: 82 | 14 |
| (K)FSLVGIAGQDLNEGNR(T) SEQ ID NO: 83 | 14 |
| (K)GDEEGIPAVVIDMSGLR(E) SEQ ID NO: 84 | 14 |
| (K)VFHGLK(S) SEQ ID NO: 85 | 14 |
| (K)YAISMAR(K) SEQ ID NO: 86 | 14 |
| (R)VNKPPYPK(L) SEQ ID NO: 87 | 14 |
| (K)LSPEELLLR(W) SEQ ID NO: 88 | 14 |
| (K)IKVPVDWMR(V) SEQ ID NO: 89 | 14 |
| (R)QFVTATDVVR(G) SEQ ID NO: 90 | 14 |
| (R)NWMNSLGVNPR(V) SEQ ID NO: 91 | 14 |
| (K)MINLSVPDTIDER(T) SEQ ID NO: 93 | 14 |
| (R)VYALPEDLVEVNPK(M) SEQ ID NO: 94 | 14 |
| (K)ESLVGIAGQDLNEGNR(T) SEQ ID NO: 95 | 14 |
| (K)GDEEGIPAVVIDMSGLR(E) SEQ ID NO: 96 | 14 |
| (K)VFHGLK(T) SEQ ID NO: 97 | 14 |
| (K)YAISMAR(K) SEQ ID NO: 98 | 14 |
| (R)VNKPPYPK(L) SEQ ID NO: 99 | 14 |
| (K)LSPEELLLR(W) SEQ ID NO: 100 | 14 |
| (K)IKVPVDWNR(V) SEQ ID NO: 101 | 14 |

TABLE 1-continued

| Peptide Sequence | Fig. No. |
|---|---|
| (R)QFVTATDVVR(G) SEQ ID NO: 102 | 14 |
| (R)NWMNSLGVNPR(V) SEQ ID NO: 103 | 14 |
| (K)MINLSVPDTIDER(T) SEQ ID NO: 104 | 14 |
| (R)VYALPEDLVEVNPK(M) SEQ ID NO: 105 | 14 |
| (K)GDEEGIPAVVIDMSGLR(E) SEQ ID NO: 106 | 14 |
| (R)NWMNSLGVNPR(V) SEQ ID NO: 107 | 14 |
| (R)NWMNSLGVNPR(V) SEQ ID NO: 108 | 14 |
| (R)NWMWSLGVNPR(V) SEQ ID NO: 109 | 14 |
| (R)NWMNSLGVNPR(V) SEQ ID NO: 110 | 14 |
| (R)NWMNSLGVNPR(V) SEQ ID NO: 111 | 14 |
| (R)NWMNSLGVNPR(V) SEQ ID NO: 112 | 14 |
| (R)NWMNSLGVNPR(V) SEQ ID NO: 113 | 14 |
| (R)NWMNSLGVNPR(V) SEQ ID NO: 114 | 14 |
| (R)NWMNSLGVNPR(V) SEQ ID NO: 115 | 14 |
| (R)NWMNSLGVNPR(V) SEQ ID NO: 116 | 14 |
| (R)NWMNSLGVNPR(V) SEQ ID NO: 117 | 14 |
| (R)NWMNSLGVNPR(V) SEQ ID NO: 118 | 14 |

Fugetactic proteins can be in secreted or non-secreted form. That is, in the in vitro or in vivo methods provided herein, either the non-secreted or secreted forms of the proteins can be used. Secreted proteins can contain a signal or secretory sequence. These sequences are known in the art. Secreted proteins can be actively or passively secreted. Accordingly, one of ordinary skill in the art is able to construct a secreted protein by altering the sequence of a non-secreted form of the protein. For example, the endoplasmic reticulum retention signal of a non-secreted heat shock protein can be removed or altered to promote secretion of the HSP (see Strbo, et al., Heat shock fusion protein gp96-Ig mediates strong CD8 CTL expansion in vivo, Am. J. of Reproductive Immunol. 2002, 48: 220-225). The sequence of a non-secreted HSP can also be altered by providing a signal or secretory sequence. Unaltered proteins with retention signals, however, can also be used and do not necessarily have to be altered.

Methods of producing a substantially pure fugetactic agent, such as a fugetactic polypeptide are provided. The fugetactic agent, e.g. a fugetactic polypeptide, can be isolated from a non-homogenous proteinaceous solution such as a cell culture supernatant or cell homogenate. Tumor cells, such as thymoma cells, can be isolated from a subject by the disaggregation of a piece of tumor tissue, and forming cell suspensions. Alternatively, tumor cells may be tumor cell lines. Disaggregation of a tissue or a population of cells can be readily accomplished using techniques known to those skilled in the art. For example, the tissue or organ can be disaggregated mechanically and/or treated with digestive enzymes and/or chelating agents that weaken the connections between neighboring cells, making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase, etc. Mechanical disruption can also be accomplished by a number of methods including, but not limited to, the use of grinders, blenders, sieves, homogenizers, pressure cells, or insonators to name but a few. For a review of tissue disaggregation techniques, see Freshney, *Culture of Animal Cells*, A Manual of Basic Techniques, 2d Ed., A. R. Liss, Inc., New York, 1987, Ch. 9, pp. 107-126.

Once the tissue has been reduced to a suspension of individual cells, the suspension optionally can be fractionated into subpopulations from which the desired cell and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, *Culture of Animal Cells*, A Manual of Basic Techniques, 2d Ed., A. R. Liss, Inc., New York, 1987, Ch. 11 and 12, pp. 137-168.

The cells can also be cultured in order to prepare a culture supernatant that contains the fugetactic agent. Cells can be cultured in an appropriate nutrient medium under conditions that are metabolically favorable for the growth of the cells. As used herein, the phrase 'metabolically favorable conditions" refers to conditions that maintain cell viability and promote secretion of factors into the culture media. Such conditions include growth in nutrient medium at 37° C. in a 5% $CO_2$ incubator with greater than 90% humidity. Many commercially available media, such as RPMI 1640, Fisher's, Iscove's, McCoy's, Dulbecco's Modified Eagle's Medium, etc., and the like, which may or may not be supplemented with serum, may be suitable for use as nutrient medium. Antibiotics such as penicillin and streptomycin may also be included. In preferred embodiments, the tumor cells are cultured first, for a brief period of time in the presence of 10% serum. The medium is then changed to a serum-free medium in order to minimize the number of extraneous (e.g. non-tumor cell derived) agents that would be present in the medium under continuous culture. The serum-free cell medium becomes a cell conditioned medium (supernatant) upon the growth of the cells. In general, these cell suspensions can be cultured according to standard cell culture techniques. In small scale, the cultures can be contained in culture plates, flasks, and dishes. In larger scale, the cultures can be contained in roller bottles, spinner flasks and other large scale culture vessels such as fermenters. Culturing in a three-dimensional, porous, solid matrix may also be used. Preferably, the cells are grown to confluency (for example, at a concentration of $10^6$ cells/mL medium in suspension).

The supernatant from the cell culture is then isolated. The supernatant may be harvested by aspiration, or by centrifugation of the cell culture to remove cells. The cultures can also be filtered to remove cells and cell debris. The supernatant is then fractionated and each fraction is contacted with a cell with migratory capacity. A "cell with migratory capacity" or a "migratory cell" is a cell that is capable of either moving towards or away from a stimulus. They can respond to a variety of chemotactic signals, including chemoattractive and chemorepulsive (fugetactic) signals.

A "cell with migratory capacity" is an eukaryotic cell that includes, but is not limited to, a cell of hematopoietic origin, a cell of neural origin, a cell of epithelial origin, a cell involved in angiogenesis, a cell of mesenchymal origin, an embryonic stem cell, or a germ cell. Such cells with migratory capacity can respond to a variety of chemotactic signals, including chemoattractive and chemorepulsive (fugetactic) signals. The response typically involves changes in the actin cytoskeleton.

Cells of "hematopoietic origin" include, but are not limited to, pluripotent stem cells, multipotent progenitor cells and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage. The hematopoietic cells may be derived from a tissue such as bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue includes the thymus, spleen, liver, lymph node, skin, tonsil and Peyer's patches. In other embodiments, the "hematopoietic origin" cells may be derived from in vitro cultures of any of the foregoing cells, and in particular in vitro cultures of progenitor cells.

"Immune cells" as used herein are cells of hematopoietic origin that are involved in the specific recognition of antigens. Immune cells include antigen presenting cells (APCs), such as dendritic cells or macrophages, B cells, T cells, etc. "T cells" as used herein include T cells of a $CD4^{lo}CD8^{hi}CD69^{+}TCR^{+}$, $CD4^{hi}CD8^{lo}CD69^{+}TCR^{+}$, $CD4^{+}CD3^{+}RO^{+}$ and/or $CD8^{+}CD3^{+}RO^{+}$ phenotype. T cells include cytotoxic T lymphocytes (CTLs).

Cells of neural origin, include neurons and glia, and/or cells of both central and peripheral nervous tissue that express RR/B (see, U.S. Pat. No. 5,863,744, entitled: "Neural cell protein marker RR/B and DNA encoding same," issued Jan. 26, 1999, to Avraham, et al.).

Cells of epithelial origin, include cells of a tissue that covers and lines the free surfaces of the body. Such epithelial tissue includes cells of the skin and sensory organs, as well as the specialized cells lining the blood vessels, gastrointestinal tract, air passages, ducts of the kidneys and endocrine organs.

Cells of mesenchymal origin include cells that express typical fibroblast markers such as collagen, vimentin and fibronectin.

Cells involved in angiogenesis are cells that are involved in blood vessel formation and include cells of epithelial origin and cells of mesenchymal origin.

An embryonic stem cell is a cell that can give rise to cells of all lineages; it also has the capacity to self-renew.

A germ cell is a cell specialized to produce haploid gametes. It is a cell further differentiated than a stem cell, that can still give rise to more differentiated germ-line cells.

The tumor cell may be of a cancer or tumor type demonstrated to escape immune recognition. Such cancers or tumors include cancer of the thymus, as well as biliary tract cancer; brain cancer, including glioblastomas and medulloblastomas; breast cancer; cervical cancer; choriocarcinoma; colon cancer; colorectal cancer; endometrial cancer; esophageal cancer; gastric cancer; glioma; hematological neoplasms, including acute lymphocytic, lymphoid cell-derived leukemia and myelogenous leukemia; multiple myeloma; AIDS associated leukemias and adult T cell leukemia and lymphoma; intraepithelial neoplasms, including Bowen's disease and Paget's disease; liver cancer (hepatocarcinoma); lung cancer (e.g. Lewis lung carcinoma); lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreatic cancer; prostate cancer, rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma and non-seminoma (e.g., teratomas or choriocarcinomas)), stromal tumors and germ cell tumors; thyroid cancer, including thyroid adenocarcinoma and medullar carcinoma; and renal cancer including adenocarcinoma and Wilms tumor.

The tumor cell isolate can be isolated from the supernatants of the above-described cell cultures. The entire culture may be homogenized and subjected to the steps described herein for isolation of a fugetactic agent, such as a fugetactic polypeptide. In still other embodiments, the fugetactic agent takes the form of a diluted supernatant from these tumor cells. The supernatant can be diluted about 2-, 3-, 4-, 5-, 6-, 7-, 8-, 9-, 10-, 15-, 20-, 25-, 30-, 40-, 50-, 60-, 70-, 80-, 90-, 100-, 125-, 150- or 200-fold, etc.

The fugetactic agent containing tumor cell supernatant can be fractionated according to standard chromatographic procedures to facilitate isolation of the fugetactic agent. One of ordinary skill in the art will be familiar with such procedures that include, but are not limited to, size-exclusion chromatography, FPLC, HPLC, gel filtration chromatography, ion-exchange chromatography, hydrophobic chromatography, immune-affinity chromatography, etc.

The fugetactic response of the T cells to the fugetactic agent can be measured as described herein, or according to the transmigration assays described in greater detail in the Examples. Other suitable methods will be known to one of ordinary skill in the art and can be employed using only routine experimentation.

The fractions which are positive for fugetactic activity can be subjected to additional rounds of screening using the foregoing methodology. The purity of the fraction can be assessed after each round of culture stimulation by subjecting an aliquot of the fraction to SDS-PAGE or other analytical method for visualizing the mixture of constituents in the fraction. The nature of the fugetactic agent (e.g., protein, nucleic acid, lipid, carbohydrate etc.), can be confirmed at any time by treating an aliquot of a positive fraction with non-specific degradative enzymes for the foregoing classes of molecules and testing the treated fraction in the same assays detailed above.

The fugetactic agent can then be further isolated if desired using immunological and molecular biological methods (see, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York). For example, a fraction positive for the tumor cell isolate which is sufficiently purified can be subjected to protein sequencing according to standard methods. For example, the fraction can be subjected to SDS-PAGE, transferred to a membrane such as polyvinylidene fluoride by electroblotting, and N-terminal amino sequence determined by Edman degradation. Any sequence information can be used to screen databases for homology to existing proteins and also to generate degenerate nucleic acids useful for screening a cDNA library by standard methods such as colony hybridization or polymerase chain reaction.

Alternatively, the positive fraction can be used to generate antibodies specific for the fugetactic agent. Such antibodies can then be used in expression cloning protocols, Western blots, and other techniques useful in isolation of the fugetactic agent. In the foregoing methods, any cDNA libraries, expression libraries, etc., are created from tumor cells, preferably thymoma cells, and even more preferably EL4 thymoma cells.

The invention also provides agents that selectively bind to and preferably inhibit the activity of the fugetactic agents provided herein (i.e., "anti-fugetactic agents"). Anti-fugetactic agents can be isolated peptides, antibodies or antigen-binding fragments thereof or other inhibitors, e.g. small molecules. These agents include HSP inhibitors, such as radicicol, Geldanamycin, 17-A-GA, herbimycin A, PU3, novobiocin and G-coupled pertussis toxin. Other HSP inhibitors are known in the art. In some embodiments the anti-fugetactic agent is not a benzoquinoid ansamycin. In still other embodiments the anti-fugetactic agent is not radicicol. In yet other embodiments the anti-fugetactic agent is not geldanamycin or 17-A-GA. In still other embodiments the anti-fugetactic agent is not herbimycin A. In yet other embodiments the anti-fugetactic agent is not PU3. In still other instances the anti-fugetactic agent is not novobiocin. In other instances the anti-fugetactic agent is not pertussis toxin. Anti-fugetactic agents can also be molecules that competitively or non-competitively bind to the receptors of the fugetactic proteins provided herein. For instance receptors have been postulated for HSPs, which are, for example, CD91, CD36 and tlr4.

The anti-fugetactic agents of the invention can be discovered with routine screening methods. The invention therefore provides a method of screening for an anti-fugetactic agent. Screening for an anti-fugetactic agent includes combining a migratory cell, such as an immune cell, with a fugetactic agent and determining a control level of fugetactic activity. Combining the fugetactic agent, migratory cell and a candidate anti-fugetactic agent provides a test level of activity, which can then be compared with the control level to determine whether or not the candidate anti-fugetactic agent exhibits the desired activity.

Further, it is possible to isolate proteins which bind to the fugetactic agents disclosed herein, including antibodies and other binding partners of the fugetactic agents such as receptors. The proteins which bind to the fugetactic agents can be used, for example, in screening assays to detect the presence or absence of fugetactic agents as well as in purification protocols to isolate fugetactic agents. The binding proteins also can be used to block the effects of the fugetactic agents. Such assays can be used to confirm the specificity of binding.

The invention, therefore, embraces binding agents which, for example, can be antibodies or fragments of antibodies having the ability to selectively bind to fugetactic agents. These antibodies can also inhibit the fugetactic properties of the agents described above. In important embodiments, the binding agents bind selectively to a fugetactic agent. In further important embodiments, the binding agents bind selectively to a HSP, HSPLP, L-plastin or LPLP. These binding agents can inhibit repulsion of immune cells. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention provides other peptides or polypeptides of numerous size and type that bind specifically to the fugetactic agents provided herein or complexes of fugetactic agents and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

As detailed herein, the foregoing antibodies and other binding molecules may be used for example to identify tissues expressing protein or to purify protein. Antibodies also may be coupled to specific diagnostic labeling agents for imaging of cells and tissues that express a fugetactic agent as provided herein.

Anti-fugetactic agents also include molecules which reduce the expression level and/or function level of the fugetactic agents of the invention. Such molecules include antisense molecules and RNAi molecules. The use of RNA interference or "RNAi" involves the use of double-stranded RNA (dsRNA) to block gene expression. (see: Sui, G, et al, Proc Natl. Acad. Sci U.S.A. 99:5515-5520,2002). Methods of applying antisense and RNAi strategies in embodiments of the invention would be understood by one of ordinary skill in the art.

The fugetactic agents of the invention are useful for modulating cell migration away from specific sites in a subject. Thus, in one aspect, the invention involves a method of promoting fugetaxis at a specific site by administrating a fugetactic agent provided herein in an effective amount to promote fugetaxis at the site.

As used herein, a subject is a human subject, a non-human primate, a horse, a cow, a pig, a sheep, a bird such as a chicken, a dog, a cat, a fish, etc. In preferred embodiments, the subject is a human.

A "site" can be any place in a subject where the promotion or inhibition of fugetaxis is needed. For example, such sites include a site of inflammation, infection, an autoimmune reaction, an allergic reaction, transplantation (e.g. a transplanted organ or tissue), implant (e.g. a medical or prosthetic device or a stent) and a tumor. One of ordinary skill in the art would be able to easily determine at which site the promotion or inhibition of fugetaxis would be beneficial. These sites include, but are not limited to, a site of inflammation, a site of an autoimmune reaction and a site of a transplanted organ or tissue. "Inflammation" as used herein, is a localised protective response elicited by a foreign (non-self) antigen, and/or by an injury or destruction of tissue(s), which serves to destroy, dilute or sequester the foreign antigen, the injurious agent, and/or the injured tissue. Inflammation occurs when tissues are injured by viruses, bacteria, trauma, chemicals, heat, cold, or any other harmful stimuli. In such instances, the classic weapons of the immune system (T cells, B cells, macrophages) interface with cells and soluble products that are mediators of inflammatory responses (neutrophils, eosinophils, basophils, kinin and coagulation systems, and complement cascade).

A typical inflammatory response is characterized by (i) migration of leukocytes at the site of antigen (injury) localization; (ii) specific and nonspecific recognition of "foreign" and other (necrotic/injured tissue) antigens mediated by B and T lymphocytes, macrophages and the alternative complement pathway; (iii) amplification of the inflammatory response with the recruitment of specific and nonspecific effector cells by complement components, lymphokines and monokines, kinins, arachidonic acid metabolites, and mast cell/basophil products; and (iv) macrophage, neutrophil and lymphocyte participation in antigen destruction with ultimate removal of antigen particles (injured tissue) by phagocytosis. The ability of the immune system to discriminate between "self" and "non-self" (foreign) antigens is therefore vital to the functioning of the immune system as a specific defense against "non-self" antigens.

"Non-self" antigens are those antigens on substances entering a subject, or exist in a subject but are detectably different or foreign from the subject's own constituents, whereas "self" antigens are those which, in the healthy subject, are not detectably different or foreign from its own constituents. However, under certain conditions, including in certain disease states, an individual's immune system will identify its own constituents as "non-self," and initiate an immune response against "self-antigens," at times causing more damage or discomfort as from, for example, an invading microbe or foreign material, and often producing serious illness in a subject.

In another important embodiment, the inflammation is caused by an immune response against "self-antigen," and the subject in need of treatment according to the invention has an autoimmune disease. "Autoimmune disease" as used herein, results when a subject's immune system attacks its own organs or tissues, producing a clinical condition associated with the destruction of that tissue, as exemplified by diseases such as rheumatoid arthritis, uveitis, insulin-dependent diabetes mellitus, hemolytic anemias, rheumatic fever, Crohn's disease, Guillain-Barre syndrome, psoriasis, thyroiditis, Graves' disease, myasthenia gravis, glomerulonephritis, autoimmune hepatitis, multiple sclerosis, systemic lupus erythematosus, etc.

Autoimmune disease may be caused by a genetic predisposition alone, by certain exogenous agents (e.g., viruses, bacteria, chemical agents, etc.), or both. Some forms of autoimmunity arise as the result of trauma to an area usually not exposed to lymphocytes, such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of a subject to antigens which are antigenicly similar to, that is cross-reactive with, the subject's own tissue. In rheumatic fever, for example, an antigen of the streptococcal bacterium, which causes rheumatic fever, is cross-reactive with parts of the human heart. The antibodies cannot differentiate between the bacterial antigens and the heart muscle antigens, consequently cells with either of those antigens can be destroyed.

Other autoimmune diseases, for example, insulin-dependent diabetes mellitus (involving the destruction of the insulin producing beta cells of the islets of Langerhans), multiple sclerosis (involving the destruction of the conducting fibers of the nervous system) and rheumatoid arthritis (involving the destruction of the joint-lining tissue), are characterized as being the result of a mostly cell-mediated autoimmune response and appear to be due primarily to the action of T cells (See, Sinha et al., *Science,* 1990, 248:1380). Yet others, such as myesthenia gravis and systemic lupus erythematosus, are characterized as being the result of primarily a humoral autoimmune response. Nevertheless, inhibition of migration of immune cells to a specific site of inflammation involved in any of the foregoing conditions according to the invention, is beneficial to the subject since it inhibits escalation of the inflammatory response, protecting the specific site (e.g., tissue) involved, from "self-damage."

In a further important embodiments, the inflammation is caused by an immune response against "non-self-antigens" (including antigens of necrotic self-material), and the subject in need of treatment according to the invention is a transplant recipient, has atherosclerosis, has suffered a myocardial infarction and/or an ischemic stroke, has an abscess, and/or has myocarditis. This is because after cell is (or organ) transplantation, or after myocardial infarction or ischemic stroke, certain antigens from the transplanted cells (organs), or necrotic cells from the heart or the brain, can stimulate the production of immune lymphocytes and/or autoantibodies, which later participate in inflammation/rejection (in the case of a transplant), or attack cardiac or brain target cells causing inflammation and aggravating the condition (Johnson et al., *Sem. Nuc. Med.* 1989, 19:238; Leinonen et al., *Microbiol. Path.,* 1990, 9:67; Montalban et al., *Stroke,* 1991, 22:750).

As used herein a "site of an allergic reaction" is any location, local or systemic, where there is an allergic response to an allergen. Allergic reactions in man and animals has been extensively studied and the basic immune mechanisms involved are well known. Allergic conditions or diseases in humans include but are not limited to eczema, allergic rhinitis or coryza, hay fever, conjunctivitis, bronchial or allergic asthma, urticaria (hives) and food allergies; atopic dermatitis; anaphylaxis; drug allergy; angioedema; and allergic conjunctivitis. An allergic reaction may be local or systemic anaphylaxis.

The generic name for molecules that cause an allergic reaction is allergen. There are numerous species of allergens. The allergic reaction occurs when tissue-sensitizing immunoglobulin of the IgE type reacts with foreign allergen. The IgE antibody is bound to mast cells and/or basophils, and these specialized cells release chemical mediators (vasoactive amines) of the allergic reaction when stimulated to do so by allergens bridging the ends of the antibody molecule. Histamine, platelet activating factor, arachidonic acid metabolites, and serotonin are among the best known mediators of allergic reactions in man. Histamine and the other vasoactive amines are normally stored in mast cells and basophil leukocytes. The mast cells are dispersed throughout animal tissue and the basophils circulate within the vascular system. These cells manufacture and store histamine within the cell unless the specialized sequence of events involving IgE binding occurs to trigger its release.

A method of repelling immune cells from a material surface is also provided. "Material surfaces" as used herein, include, but are not limited to, medical devices, dental and orthopedic prosthetic implants, artificial valves, and organic implantable tissue such as a stent, allogeneic and/or xenogeneic tissue, organ and/or vasculature. Material surfaces also encompass tissues that are produced through tissue engineering technology.

Implantable prosthetic devices have been used in the surgical repair or replacement of internal tissue for many years. Orthopedic implants include a wide variety of devices, each suited to fulfill particular medical needs. Examples of such devices are hip joint replacement devices, knee joint replacement devices, shoulder joint replacement devices, and pins, braces and plates used to set fractured bones. Some contemporary orthopedic and dental implants, use high performance metals such as cobalt-chrome and titanium alloy to achieve high strength. These materials are readily fabricated into the complex shapes typical of these devices using mature metal working techniques including casting and machining.

The material surface is coated with an amount of a fugetactic agent of the invention effective to repel immune cells. In important embodiments, the material surface is part of an implant. In important embodiments, in addition to a fugetactic agent, the material surface may also be coated with a cell-growth potentiating agent, an anti-infective agent, and/or an anti-inflammatory agent.

According to another aspect of the invention, a method of treating infertility and premature labor, including premature delivery and impending miscarriage, is provided. The method involves administering to a subject in need of such treatment a fugetactic agent in an amount effective to inhibit immune cells from migrating close to a germ cell (including an egg, a sperm, a fertilized egg, or an implanted embryo) in the subject. In further embodiments, the administration is local to a germ cell-containing site of the subject.

According to a further aspect of the invention, a method of contraception in a subject, is provided. The method involves administering to a subject in need of such treatment, an anti-fugetactic agent in an amount effective to inhibit migration of germ cells in the subject. In further embodiments, the administration is local to a germ cell-containing site of the subject.

According to another aspect of the invention, a method of inhibiting tumor cell metastasis in a subject is provided. The method involves locally administering to a tumor site in a subject in need of such treatment an anti-fugetactic agent in an amount effective to inhibit metastasis of tumor cells from the tumor site in the subject.

According to another aspect of the invention, a method of inhibiting endothelial cell migration to a tumor site in a subject, is provided. The method involves locally administering to an area surrounding a tumor site in a subject in need of such treatment a fugetactic agent in an amount effective to inhibit endothelial cell migration to the tumor site in the subject. In certain embodiments, the area surrounding the tumor site is not immediate to the tumor site. Important fugetactic agents are as described herein.

The methods of the invention also include a method of eliciting or enhancing a local immune response by administering an anti-fugetactic agent of the invention in an amount effective to inhibit immune cell specific fugetactic activity at a specific site in a subject thereby enhancing a local immune response. In some embodiments, the specific site is a site of an infection. Efficient recruitment of immune cells to help eliminate the infection is beneficial.

In further embodiments, the specific site is a tumor. It is beneficial to enhance the migration of immune cells to the tumor site, as well as to maintain such cells at this site. A tumor site can be any site where cancer cells are present in a subject. In further embodiments, co-administration of anti-cancer agents other than anti-fugetactic agents is also provided.

In another embodiment the specific site is a germ cell site where the recruitment of immune cells to the specific sites will help eliminate unwanted germ cells, and/or implanted and non-implanted embryos. In further embodiments, co-administration of contraceptive agents other than anti-fugetactic agents is also provided. Non-anti-fugetactic contraceptive agents are well known in the art.

The foregoing methods of therapy may include co-administration of a non-fugetactic therapeutic agent together with a fugetactic agent or anti-fugetactic agent of the invention that can act cooperatively, additively, or synergistically with the fugetactic agent or anti-fugetactic agent of the invention to promote or inhibit the migration of cells from a specific site in a subject. According to some embodiments, a fugetactic agent or anti-fugetactic agent is administered substantially simultaneously with a non-fugetactic therapeutic agent. By "substantially simultaneously," it is meant that the fugetactic agent is administered to the subject close enough in time with the administration of the non-fugetactic therapeutic agent, whereby the non-fugetactic therapeutic agent may exert a potentiating effect on migration activity of the fugetactic agent or anti-fugetactic agent. Thus, by substantially simultaneously it is meant that the fugetactic agent or anti-fugetactic agent is administered before, at the same time, and/or after the administration of the non-fugetactic therapeutic agent. In some embodiments the fugetactic agents or anti-fugetactic agents can be administered as a polypeptide or as a nucleic acid, which expresses the fugetactic agent or anti-fugetactic agent.

An anti-infectious agent as used herein is an agent which reduces the activity of or kills a microorganism and includes: Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berytbromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalornicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride.

In other embodiments, the non-fugetactic therapeutic agents are anti-inflammatory agents. Such anti-inflammatory agents include: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Anti-allergic agents include, but are not limited to, antihistamines, steroids, and prostaglandin inducers. Anti-histamines are compounds which counteract histamine released by mast cells or basophils. These compounds are well known in the art and commonly used for the treatment of allergy. Anti-histamines include, but are not limited to, loratidine, cetirizine, buclizine, ceterizine analogues, fexofenadine, terfenadine, desloratadine, norastemizole, epinastine, ebastine, ebastine, astemizole, levocabastine, azelastine, tranilast, terfenadine, mizolastine, betatastine, CS 560, and HSR 609. Prostaglandin inducers are compounds which induce prostaglandin activity. Prostaglandins function by regulating smooth muscle relaxation. Prostaglandin inducers include, but are not limited to, S-5751.

Steroids include, but are not limited to, beclornethasone, fluticasone, tramcinolone, budesonide, corticosteroids and budesonide.

Corticosteroids include, but are not limited to, beclomethasome dipropionate, budesonide, flunisolide, fluticaosone, propionate, and triamcinoone acetonide.

Systemic corticosteroids include, but are not limited to, methylprednisolone, prednisolone and prednisone.

Commonly used allergy drugs which are currently in development or on the market are shown in Table 2.

TABLE 2

Allergy Drugs in Development or on the Market

| MARKETER | BRAND NAME (GENERIC NAME) | MECHANISM |
|---|---|---|
| Schering-Plough | Claritin + Claritin D (loratidine) | Anti-histamine |
| | Vancenase (beclomethasone) | Steroid |
| UCB | Reactine (cetirizine) (US) | Anti-histamine |
| | Zyrtec (cetirizine)(ex US) | |
| | Longifene (buclizine) | Anti-histamine |
| | UCB 28754 (ceterizine alalogue) | Anti-histamine |
| Glaxo | Beconase (beclomethasone) | Steroid |
| | Flonase (fluticasone) | Steroid |
| Aventis | Allegra (fexofenadine) | Anti-histamine |
| | Seldane (terfenadine) | Anti-histamine |
| Pfizer | Reactine (cetirizine) (US) | Anti-histamine |
| | Zyrtec/Reactine (cetirizine)(ex US) (both licensed from UCB) | |
| Sepracor | Allegra (fexofenadine) | Anti-histamine |
| | Desloratadine (lic to Schering-Plough) | Anti-histamine |
| | Cetirizine (—) (lic to UCB) | Anti-histamine |
| | Norastemizole (option to J&J not exercised, Oct. 17, 1999) | Anti-histamine |
| B. Ingelheim | Alesion (epinastine) | Anti-histamine |
| Aventis | Kestin (ebastine) (US) | Anti-histamine |
| | Bastel (ebastine) (Eu/Ger) | |
| | Nasacort (tramcinolone) | Steroid |
| Johnson & Johnson | Hismanol (astemizole) | Anti-histamine |
| | Livostin/Livocarb (levocabastine) | Anti-histamine |
| AstraZeneca | Rhinocort (budesonide) (Astra) | Steroid |
| Merck | Rhinocort (budesonide) | Steroid |
| Eisai | Azeptin (azelastine) | Anti-histamine |
| Kissei | Rizaben (tranilast) | Anti-histamine |
| Shionogi | Triludan (terfenadine) | Anti-histamine |
| | S-5751 | Prostaglandin inducer |
| Schwarz | Zolim (mizolastine) | Anti-histamine |
| Daiichi | Zyrtec (cetirizine) | Anti-histamine |
| Tanabe Seiyaku | Talion/TAU-284 (betatastine) | Anti-histamine |
| Sankyo** | CS 560 (Hypersensitizaion therapy for cedar pollen allergy) | Other |
| Asta Medica | Azelastine-MDPI (azelastine) | Anti-histamine |
| BASF | HSR 609 | Anti-histamine |
| SR Pharma | SRL 172 | Immunomodulation |
| Peptide Therapeutics | Allergy vaccine (allergy (hayfever, anaphylaxis, atopic asthma) | Downregulates specific IgE |
| | Tolerizing peptide vaccine (rye grass peptide (T cell epitope)) | Immunosuppressant |
| Coley Pharmaceutical Group | CpG DNA | Immunomodulation |

TABLE 2-continued

| Allergy Drugs in Development or on the Market | | |
|---|---|---|
| MARKETER | BRAND NAME (GENERIC NAME) | MECHANISM |
| Genetech | Anti-IgE | Down-regulator of IgE |
| SR Pharma | SRL 172 | Immunomodulation |

Anti-allergic agents also include asthma medicaments. Asthma medicaments include, but are not limited, PDE-4 inhibitors, bronchodilator/beta-2 agonists, K+ channel openers, VLA-4 antagonists, neurokin antagonists, TXA2 synthesis inhibitors, xanthanines, arachidonic acid antagonists, 5 lipoxygenase inhibitors, thromboxin A2 receptor antagonists, thromboxane A2 antagonists, inhibitor of 5-lipox activation proteins, and protease inhibitors.

In certain embodiments, the non-fugetactic therapeutic agents are immunosuppressants. Such immunosuppressants include: Azathioprine; Azathioprine Sodium; Cyclosporine; Daltroban; Gusperimus Trihydrochloride; Sirolimus; Tacrolimus.

Non-anti-fugetactic agents are also anti-cancer agents. Anti-cancer agents include: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Podofilox; Porfimer Sodium; Porfiromycin; Prednimustine; Procarbazine Hydrochloride, Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Non-fugetactic therapeutic agents also include cell-growth potentiating agents which stimulate growth of a cell and includes growth factors such as PDGF, EGF, FGF, TGF, NGF, CNTF, and GDNF.

The methods provided can also include the adminiistration of a second agent that influences cell migration. These agents may be either chemoattracting or chemorepelling depending on the embodiment. In a preferred embodiment, such agents include cytokines. "Cytokine" is a generic term for non-antibody soluble proteins which are released from one cell subpopulation and which act as intercellular mediators, for example, in the generation or regulation of an immune response. See *Human Cytokines: Handbook for Basic & Clinical Research* (Aggrawal, et al. eds., Blackwell Scientific, Boston, Mass. 1991) (which is hereby incorporated by reference in its entirety for all purposes). Cytokines include, e.g., interleukins IL-1 through IL-15, tumor necrosis factors $\alpha$ & $\beta$, interferons $\alpha$, $\beta$, and $\gamma$, tumor growth factor beta (TGF-$\beta$), colony stimulating factor (CSF) and granulocyte monocyte colony stimulating factor (GM-CSF). The action of each cytokine on its target cell is mediated through binding to a cell surface receptor. Cytokines share many properties of hormones, but are distinct from classical hormones in that in vivo, they generally act locally on neighboring cells within a tissue. The activities of cytokines range from promoting cell growth (e.g., IL-2, IL-4, and IL-7), and arresting growth (IL-10, tumor necrosis factor and TGF-$\beta$), to inducing viral resistance (IFN $\alpha$, $\beta$, and $\gamma$). See Fundamental Immunology (Paul ed., Raven Press, 2nd ed. 1989); Encyclopedia of Immunology, (Roitt ed., Academic Press 1992) (which are hereby incorporated by reference in their entirety for all purposes). In certain embodiments, the cytokine is a cytokine with chemoattractant and/or chemokinetic properties. Examples of such cytokines include: PAF, N-formylated peptides, C5a, $LTB_4$, $LXA_4$, chemokines: CXC, IL-8, GCP-2, GRO$\alpha$, is GRO$\beta$, GRO$\gamma$, ENA-78, NAP-2, IP-10, MIG, I-TAC, SDF-1$\alpha$, BCA-1, PF4, Bolekine, MIP-1$\alpha$, MIP-1$\beta$, RANTES, HCC-1, MCP-1, MCP-2, MCP-3, MCP-4, MCP-5 (mouse only), Leukotactin-1 (HCC-2, MIP-5), Eotaxin, Eotaxin-2 (MPIF2), Eotaxin-3 (TSC), MDC, TARC, SLC (Exodus-2, 6CKine), MIP-3$\alpha$ (LARC, Exodus-1), ELC (MIP-3$\beta$), I-309, DC-CK1 (PARC, AMAC-1), TECK, CTAK, MPIF1 (MIP-3), MIP-5 (HCC-2), HCC-4 (NCC-4), MIP-1$\gamma$ (mouse only), C-10 (mouse only); C: Lymphotactin; $CX_3C$: Fracktelkine (Neurotactin). Most preferably, the cytokine is a member of the Cys-X-Cys family of chemokines (chemokines that bind to the CXCR-4 receptor). Preferred such agents of the invention include SDF-1$\alpha$, SDF-1$\beta$, and met-SDF-1$\beta$. In further preferred embodiments, such agents include other CXCR-4 receptor ligands. CXCR-4 ligands include, but are not limited to, HIV-$1_{IIIB}$ gp120, small molecules T134 and MD3100, and/or T22 ([Tyr5,12,Lys7]-polyphemusin II) (Heveker et al., Curr Biol, 1998, 8:369-76).

The compositions, as described above, are administered in effective amounts. The effective amount will depend upon the mode of administration, the particular condition being treated and the desired outcome. It will also depend upon the stage of the condition, the age and physical condition of the subject, the nature of concurrent therapy, if any, and like factors well known to the medical practitioner. For therapeutic applications, it is that amount sufficient to achieve a medically desirable result. In some cases this is a local (site-specific) reduction of inflammation. In other cases, it is inhibition of tumor growth and/or metastasis. In some instances, an effective amount of a fugetactic agent is the amount that promotes the migration of cells away from a specific site in a subject. In other instances an effective amount of an anti-fugetactic agent is an amount that inhibits the migration of cells away from a specific site in a subject.

Generally, doses of active compounds of the present invention would be from about 0.01 mg/kg per day to 1000 mg/kg per day. It is expected that doses ranging from 50-500 mg/kg will be suitable.

A variety of administration routes are available. The methods of the invention, generally speaking, may be practiced using any mode of administration that is medically acceptable, meaning any mode that produces effective levels of the active compounds without causing clinically unacceptable adverse effects. The compositions of the invention can be administered systemically or locally. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694-1712; incorporated by reference). Those of skill in the art can readily determine the various parameters and conditions for producing antibody or peptide aerosols without resort to undue experimentation.

In some embodiments the fugetactic agents or anti-fugetactic agents can be targeted to a specific site. Targeting methods are known by those of ordinary skill in the art. For example, the agents of the invention can be conjugated to a targeting molecule. As another example, a HSP can be conjugated to a targeting molecule. Targeting molecules include, but are not limited to, molecules such as an antibody specific for a surface membrane protein on the target cell or a ligand for a receptor on the target cell. Targeting molecules, therefore include antibodies specific for tumor antigens.

Tumor-antigens include Melan-A/MART-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-9, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp$100^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, and c-erbB-2.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In certain embodiments, the fugetactic agents or anti-fugetactic agents of the invention are delivered directly to the site where the fugetactic agent is needed (e.g. at a site of inflammation; the joints in the case of a subject with rheumatoid arthritis, the blood vessels of an atherosclerotic organ, etc.). For example, this can be accomplished by attaching an isolated fugetactic molecule (nucleic acid or polypeptide) to the surface of a balloon catheter; inserting the catheter into the subject until the balloon portion is located at the site of inflammation, e.g. an atherosclerotic vessel, and inflating the balloon to contact the balloon surface with the vessel wall at the site of the occlusion. In this manner, the compositions can be targeted locally to particular inflammatory sites to modulate immune cell migration to these sites. In another example the local administration involves an implantable pump to the site in need of such treatment. Preferred pumps are as described above. In a further example, when the treatment of an abscess is involved, the fugetactic agent may be delivered topically, e.g., in an ointment/dermal formulation. Optionally, the fugetactic molecules of the invention are delivered in combination with a non-fugetactic molecule (e.g., anti-inflammatory, immunosuppressant, anticancer, etc.).

In a preferred embodiment of the invention, the isolated fugetactic agents of the invention are administered to a subject in combination with a balloon angioplasty procedure. A balloon angioplasty procedure involves inserting a catheter having a deflated balloon into an artery. The deflated balloon is positioned in proximity to the atherosclerotic plaque and the site of inflammation, and is inflated such that the plaque is compressed against the arterial wall. As a result, the layer of endothelial cells on the surface of the artery is disrupted, thereby exposing the underlying vascular smooth muscle cells. The isolated fugetactic molecule is attached to the balloon angioplasty catheter in a manner which permits release of the isolated fugetactic molecule at the site of the atherosclerotic plaque and the site of inflammation. The isolated fugetactic molecule may be attached to the balloon angioplasty catheter in accordance with standard procedures known in the art. For example, the isolated fugetactic molecule may be stored in a compartment of the balloon angioplasty catheter until the balloon is inflated, at which point it is released into the local environment. Alternatively, the isolated fugetactic molecule may be impregnated on the balloon surface, such that it contacts the cells of the arterial wall as the balloon is inflated. The fugetactic molecule also may be delivered in a perforated balloon catheter such as those disclosed in Flugelman, et al., *Circulation, v.* 85, p. 1110-1117 (1992). See, also, e.g., published PCT Patent Application WO 95/23161, for an exemplary procedure for attaching a therapeutic protein to a balloon angioplasty catheter. This procedure can be modified using no more that routine experimentation to attach a therapeutic nucleic acid to the balloon angioplasty catheter.

The invention in other aspects includes pharmaceutical compositions of fugetactic agents and anti-fugetactic agents.

The fugetactic agents, anti-fugetactic agents, or fragments thereof may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Fugetactic agents (nucleic acids or polypeptides) may be produced recombinantly. Recombinantly produced fugetactic agents such as HSPs, include chimeric proteins comprising a fusion of a HSP protein with another polypeptide, e.g., a polypeptide capable of providing or enhancing protein-protein binding, sequence specific nucleic acid binding, enhancing stability of the HSP polypeptide under assay conditions, providing a detectable moiety, such as green fluorescent protein, or providing a targeting moiety. A polypeptide fused to a fugetactic polypeptide or fragment may also provide means of readily detecting the fusion protein, e.g., by immunological recognition or by fluorescent labeling.

Various techniques may be employed for introducing nucleic acids of the invention (sense and anti-sense, dominant negative) into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can also have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the fugetactic agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480.

A preferred delivery system of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 μm can encapsulate large macromolecules. RNA, DNA, and intact virions can be encapsulated within the aqueous interior and be delivered to cells in a biologically active form (Fraley, et al., *Trends Biochem. Sci*., (1981) 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, (1985) 3:235-241.

In one important embodiment, the preferred vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System"). PCT/US/0307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the fugetactic agents described herein are encapsulated or dispersed within the biocompatible, preferably biodegradable polymeric matrix disclosed in PCT/US/03307.

The polymeric matrix preferably is in the form of a microparticle such as a microsphere (wherein a fugetactic agent is dispersed throughout a solid polymeric matrix) or a microcapsule (wherein a fugetactic agent is stored in the core of a polymeric shell). Other forms of the polymeric matrix for containing a fugetactic agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used. Preferably when an aerosol route is used the polymeric matrix and fugetactic agent are encompassed in a surfactant vehicle. The polymeric matrix composition can be selected to have both favorable degradation rates and also to be formed of a material which is bioadhesive, to further increase the effectiveness of transfer. The matrix composition also can be selected not to degrade, but rather, to release by diffusion over an extended period of time.

In another important embodiment the delivery system is a biocompatible microsphere that is suitable for local, site-specific delivery. Such microspheres are disclosed in Chickering et al., *Biotech. And Bioeng*., (1996) 52:96-101 and Mathiowitz et al., *Nature*, (1997) 386:.410-414.

Both non-biodegradable and biodegradable polymeric matrices can be used to deliver the fugetactic agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, fugetactic agents or anti-fugetactic agents are delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly (ortho)esters, poly(butic acid), poly(valeric acid), and poly (lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In addition, important embodiments of the invention include pump-based hardware delivery systems, some of which are adapted for implantation. Such implantable pumps include controlled-release microchips. A preferred controlled-release microchip is described in Santini, J T Jr., et al., *Nature,* 1999, 397:335-338, the contents of which are expressly incorporated herein by reference.

Use of a long-term sustained release implant may be particularly suitable for treatment of chronic conditions. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

The present invention is further illustrated by the following Examples, which in no way should be construed as further limiting. The entire contents of all of the references (including literature references, issued, patents, published patent applications, and co-pending patent applications) cited throughout this application are hereby expressly incorporated by reference.

EXAMPLES

Materials and Methods

Cell Culture and Production of Conditioned Media

The EL4 cell line (ATCC, Manassas, Va.) was maintained in culture in Isocove's modified Dulbecco's medium (IMDM) supplemented with 10% fetal calf serum (I10), 50 units/ml Penicillin and 50 μg/ml Streptomycin and 292 μg/ml L-Glutamine (Mediatech; Herndon, Va.). EL4 24-hour conditioned media (EL4CM24) was produced by sub-culturing the EL4 cells in hybridoma serum-free media (HSF) (Invitrogen; Carlsbad, Calif.) supplemented with 292 μg/ml L-Glutamine (Mediatech; Herndon, Va.) for three days. The cells were then transferred into fresh HSF media and cultured at an initial density of $1\times10^6$ cells/ml for 24 hours at 37° C. in a 5% $CO_2$ humidified incubator. The cell culture supernatant was collected after 24 hours and was filtered through a 0.2 μm pore size filter before use in in vitro and in vivo assays.

Preparation of Enriched Murine T-cells

C57BL/6 mice (4 to 8 weeks old) (Jackson Laboratories; Bar Harbor Me.) were euthanized, and dissection of superficial cervical, axillary, brachial and inguinal lymph nodes was performed under sterile conditions. Dissected lymph nodes were then physically disaggregated and a cell suspension generated. The cell suspension was then enriched for T cells by depletion of non-T cells using MACS Pan T cell isolation kit for mouse leukocytes (Miltenyi Biotec; Auburn, Calif.). This method typically resulted in $CD3^+$ purity greater than 95% as demonstrated by flow cytometry.

Transmigration Assays

Quantitative transmigration assays were carried out as described previously [18]. In brief, ChemoTx chemotaxis 30 μl well plates with 3 μm pore size filters (Neuro Probe; Gaithersburg, Md.) were used. 20,000 murine T-cells were loaded in the upper chamber of the ChemoTx system and subjected to positive, negative and uniform gradients of EL4CM24 in a standard checkerboard analysis of cell migration. The peak concentrations used in each gradient were 1 in 2, 1 in 10, and 1 in 100 dilutions of EL4CM24 with 10.5 media; Isocove's supplemented with 0.5% fetal calf serum, 50 units/ml Penicillin, 50 μg/ml Streptomycin and 292 μg/ml L-Glutamine (Mediatech; Herndon, Va.). The number of cells migrating in response to the given gradient was judged to be the total number of cells in the lower chamber of the ChemoTx system after a 90 minute incubation at 37° C., in a humidified 5% $CO_2$ incubator. The chemotactic index was calculated as the quotient of the average number of cells migrating in response to EL4CM24 and the average number of cells migrating in response to media alone. All experiments were performed in triplicate with duplicate wells for each gradient condition.

Heat Inactivation, Proteinase K Digestion, Heat Shock and Use of Specific Inhibitors EL4CM24 was heat inactivated at 42° C. for 1 hour prior to being used in the transmigration assays described above. Viability of the cells was observed to be greater than 90%. EL4CM24 was incubated with hydrated proteinase K agarose (Sigma-Aldrich; St. Louis, Mo.) at 1 mg/ml for 1 hour at 37° C. in a 5% $CO_2$ humidified incubator then filtered through a 0.2 μm pore-size filter prior to being used in the transmigration and intraperitoneal assays. Murine T-cells were incubated with pertussis toxin (Sigma-Aldrich; St. Louis, Mo.) at 100 ng/ml for 1 hour at 37° C. in a 5% $CO_2$ humidified incubator, prior to being used in the transmigration assays. EL4CM24 was incubated with radiciol (Sigma-Aldrich; St. Louis, Mo.) for two hours at room temperature at concentrations 0.1 μg/ml and 7.3 μg/ml. The transmigration was then carried out using the EL4CM24 mixture. As a control, transmigration assays were also carried out using gradients of HSF media supplemented with 7.3 μg/ml of radicol or using EL4CM24-radicicol mixtures from which excess radiciol had been removed using 5 kDa size exclusion Centricon Ultrafree filters (Millipore; Billerica, Mass.). EL4 cells in HSF were also exposed to Geldanamycin at 1.2 μM or 200 nM prior to use of the CM in transmigration assays. EL4 cells in HSF were also exposed to Brefeldin A at 10 μg/ml overnight for a full 24 hours prior to use of the EL4CM24 in transmigration assays. Greater than 65% viability was observed after the Brefeldin A treatment.

Ion Exchange Chromatography

Fractions of EL4CM24 were eluted from DEAE columns (Amersham Biosciences; Piscataway, N.J.) using 20 mM triethanolamine (Sigma-Aldrich; St. Louis, Mo.) 0.25 M NaCl buffer at pH 7.5. Eluted fractions were desalted using PD-10 desalting columns (Amersham Biosciences; Piscataway, N.J.), then concentrated using 5 kDa size exclusion Centricon Ultrafree filters (Millipore; Billerica, Mass.) prior to being used in the transmigration assays. Fractions of EL4CM24 were eluted at NaCl concentrations of 0.25 M, 0.5 M, 0.75 M, 1.0 M and 2.0 M. Eluted fractions were desalted prior to use in transmigration assays.

SDS PAGE 7.5% acrylamide gels were run according to the method of Laemmli, under denaturing conditions. EL4CM24 and fractions eluted by ion exchange chromatography were prepared for SDS PAGE by boiling with Laemmli buffer and 5% β-mercaptoethanol for three minutes. Silver staining of gels was achieved using the Silver Stain Plus kit (Bio-Rad; Hercules, Calif.). Sequencing of protein bands from silver stained gels was completed at the Proteomics Mass Spectrometry Lab at University of Massachusetts Medical Center using standard technologies. Further information is readily available regarding mass spectrometry analysis, including MS-Fit and MS-Tag searching on the following website: prospector.ucsf.edu/. Briefly, MS-Fit is a "peptide mass fingerprinting tool" that analyzes mass spectrometry data and attempts to "fit" the data to a protein sequence. These protein sequences can be from any known sequence and commonly are from existing databases. MS-Tag searching follows a similar methodology but attempts to match the ionic nature of the protein sequences.

Intraperitoneal Injection of Conditioned Media and Analysis of Lymphocyte Infiltration BALB/c-DO11 mice (kindly provided by Dr. Iacomini, Massachusetts General Hospital) were primed by subcutaneous injection with 100 μl of ovalbumin (ICN Biomedicals; Costa Mesa, Calif.) dissolved in Freund's complete adjuvant (Pierce Biotechnology; Rockford, Ill.) at a concentration 1 mg/ml. Three days later, mice were injected intraperitoneally with 250 μl of ovalbumin dissolved in sterile water at concentration a 0.4 mg/ml. 24 hours later, experimental mice were injected intraperitoneally with 250 μl of EL4CM24, while control mice were injected intraperitoneally with 250 μl of HSF media or protease treated EL4CM24. 24 hours later, cells were extracted from the intraperitoneal space by lavage with 5 ml of cold phosphate buffered saline (Mediatech; Herndon, Va.) and aspiration with a 10 ml syringe and 21-gauge needle. Peritoneal lavage cells were counted on a hemocytometer and then immuno-stained for anti-CD3, CD4, CD8 and TCR-kj-OVA lymphocyte expression (BD BioSciences; San Jose, Calif.) and anti-CD4 (Caltag Laboratories; Burlingame, Calif.) with antibodies labelled with Percp and PE (phytoerythrin) known fluorophor labels. T-cells expressing CD3+, CD3+ CD4+, CD3+ CD8+, CD3+ TCR-kj-OVA were then determined by FACS analysis.

Results

EL4 Conditioned Media Repels Murine Lymphocytes In Vitro

EL4CM24 was generated from EL4 cells cultured in HSF as described above. The viability of cells in culture for 24 hours in HSF was always >95%. This is significant in that it demonstrates that there was no significant apoptosis or necrosis of the cells in culture. In transmigration assays using negative gradients of 1 in 2, 1 in 10, and 1 in 100 dilutions of EL4 24-hour conditioned media (EL4CM24) migration away from conditioned media was significant compared to migration away from media alone, and decreased with increasing concentration of EL4CM24.

The mean migratory index of cells migrating in response to the 1 in 100, 1 in 10, and 1 in 2 dilutions of EL4CM24 was 382.50±50.55, 325.50±60.96, 163.83±35.42, respectively, representing chemotactic indices of 5.20±0.47, 4.67±0.89, 2.39±0.55. The average numbers of cells migrating in each gradient of EL4CM24 compared to the average number of cells migrating in media alone was statistically significant in each of the three concentrations of EL4CM24 tested (FIG. 2). Thus, factors in ELCM24, when presented in a negative gradient, repel T cells in vitro.

Figure 3:
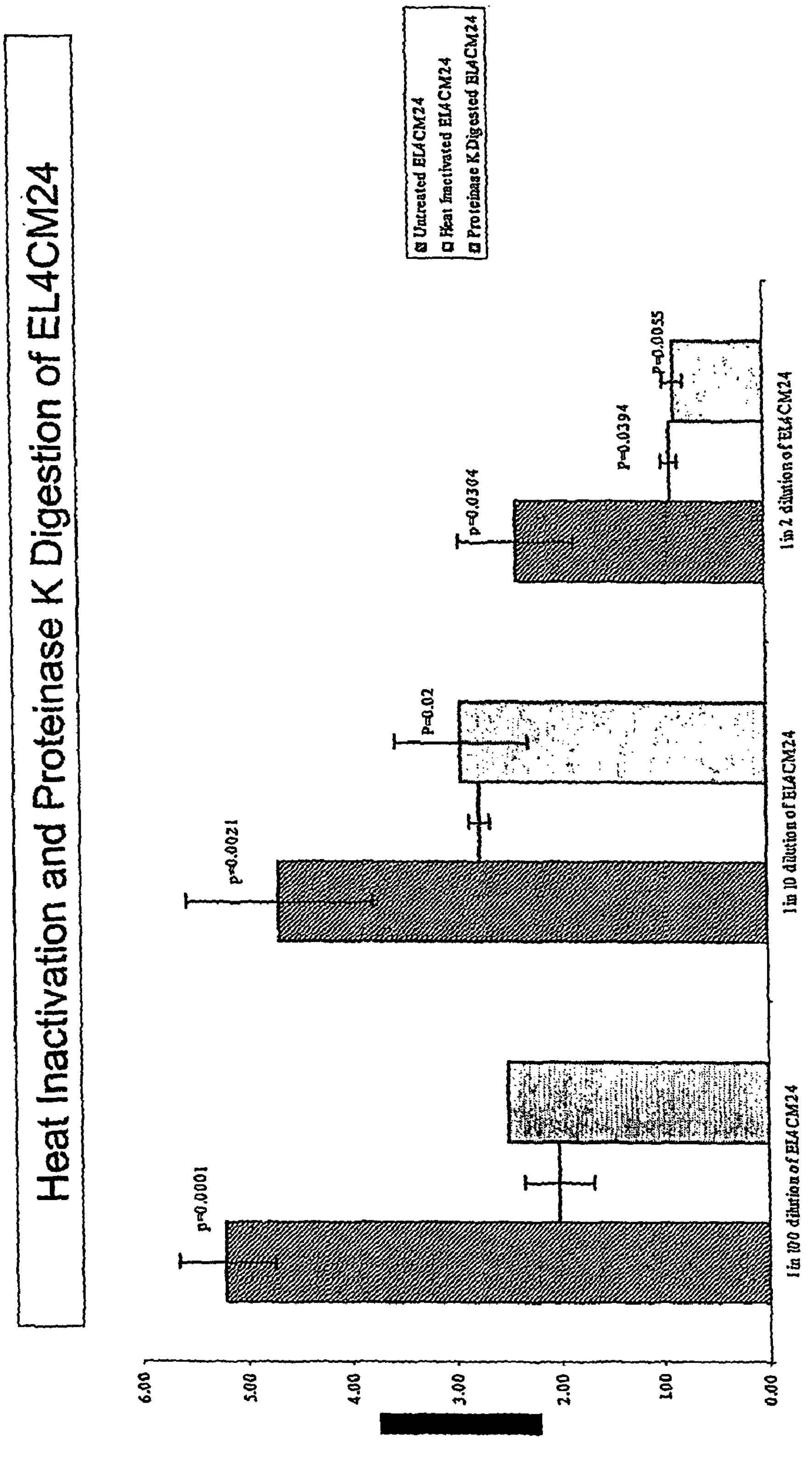
FIG. 3 provides the results of a transmigration assay using negative gradients of heat inactivated or proteinase K digested EL4 24-hour conditioned media (EL4CM24) (1 in 2, 1 in 10 and 1 in 100 dilutions).

Repulsion of Murine Lymphocytes by EL4 Conditioned Media is Reduced by Heat Inactivation and Proteinase K Digestion In transmigration assays using negative gradients of heat inactivated or proteinase K digested EL4 24-hour conditioned media, the level of migration of lymphocytes was significantly reduced by proteinase K digestion but not by heat inactivation. The mean number of cells migrating in response to the 1 in 100, 1 in 10, and 1 in 2 dilutions of heat inactivated EL4CM24 was 161.00±28.10, 230.50±41.50, 76.50±19.50, respectively, representing chemotactic indices of 2.01±0.34, 2.76±0.10, 0.91±0.07. The average numbers of cells migrating in each gradient of heat inactivated EL4CM24 compared to the average number of cells migrating in untreated EL4CM24 was only statistically significant in the highest of the three concentrations of EL4CM24 tested (FIG. 3).

The mean number of cells migrating in response to the 1 in 100, 1 in 10, and 1 in 2 dilutions of proteinase K digested EL4CM24 was 110.00±25.00, 118.00±18.10, 36.50±1.50, respectively, representing chemotactic indices of 2.50±0.00, 2.93±0.63, 0.87±0.09. The average numbers of cells migrating in each gradient of proteinase K digested EL4CM24 compared to the average number of cells migrating in untreated EL4CM24 was statistically significant in two of the three concentrations of EL4CM24 tested (FIG. 3). These results confirmed that the factors having activity in EL4CM24 are proteins.

Figure 4:
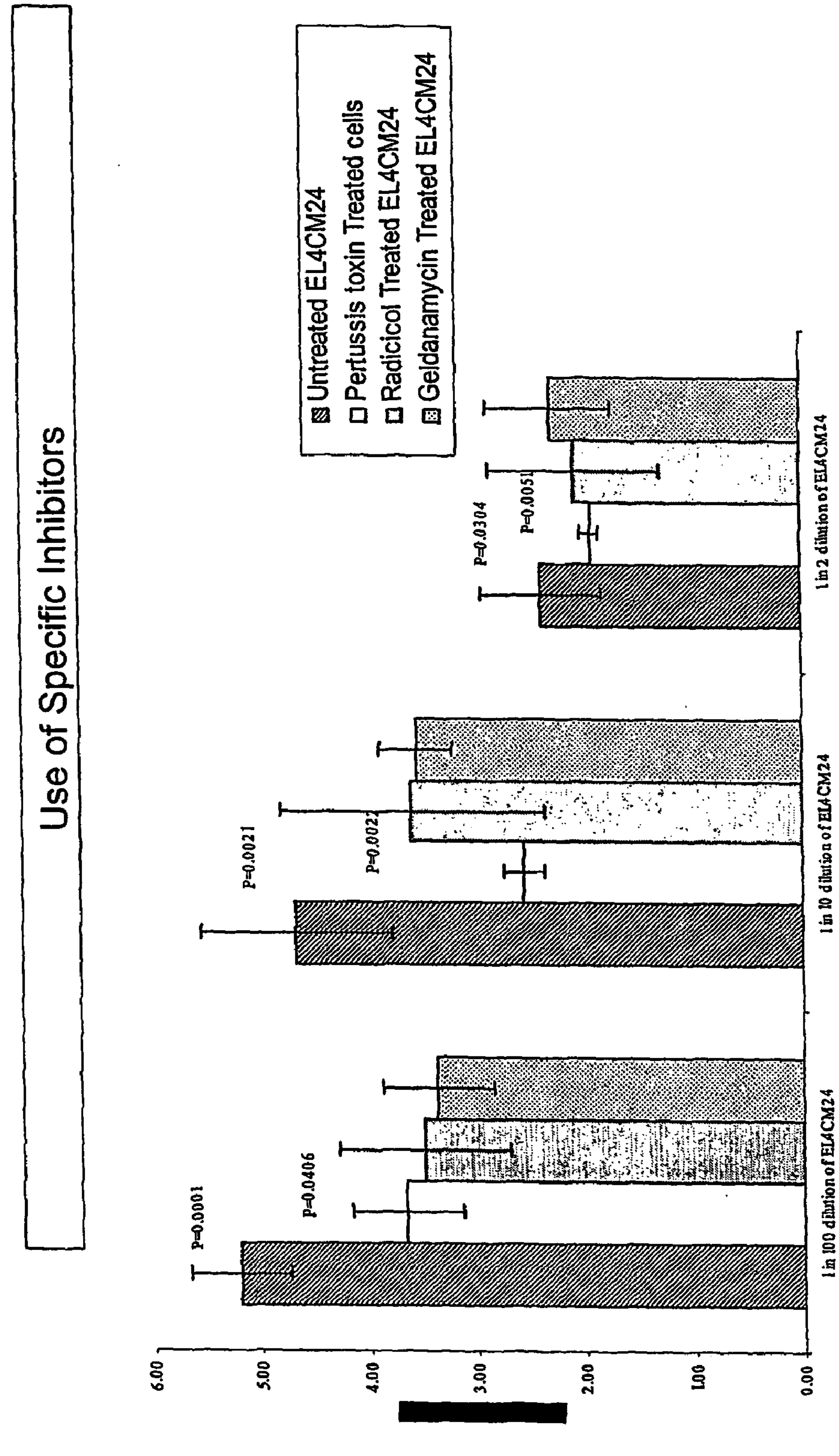
FIG. 4 provides the results of a transmigration assay using negative gradients of EL4 24-hour conditioned media (EL4CM24) with pertussis toxin treated murine lymphocytes and radicicol and Geldanamycin treated EL4CM24 (1 in 2, 1 in 10 and 1 in 100 dilutions).

Repulsion of Murine Lymphocytes by EL4 Conditioned Media is Reduced by Specific Inhibitors In transmigration assays using negative gradients of EL4 24-hour conditioned media with pertussis toxin treated murine lymphocytes, the level of migration of lymphocytes was significantly reduced. The mean number of pertussis toxin treated cells migrating in response to the 1 in 100, 1 in 10, and 1 in 2 dilutions of EL4CM24 was 37.00±4.00, 26.50±0.50, 20.50±4.50, respectively, representing chemotactic indices of 3.65±0.52, 2.57±0.18, 1.93±0.09. The average numbers of pertussis toxin treated cells migrating in each gradient of EL4CM24 compared to the average number of untreated cells migrating in EL4CM24 was statistically significant in all of the three concentrations of EL4CM24 tested (FIG. 4). The use of pertussis toxin, which inhibits G-protein coupled migration by preventing the release of GDP from the $G_{\alpha i}$ subunit, indicated that the migration induced by EL4CM24 is coupled to signaling via a G-protein pathway and implies the receptors for the active proteins in the EL4CM24 are G-protein coupled.

In transmigration assays using negative gradients of radicicol treated EL4 24-hour conditioned media, the level of migration of lymphocytes was not significantly reduced. The mean number of cells migrating in response to the 1 in 100, 1 in 10, and 1 in 2 dilutions of radicicol treated EL4CM24 was 191.83±32.38, 172.83±33.12, 84.67±18.55, respectively, representing chemotactic indices of 3.49±0.78, 3.60±1.21, 2.0810.79. The average numbers of cells migrating in each gradient of radicicol treated EL4CM24 compared to the average number of cells migrating in untreated EL4CM24 was statistically not significant in any of the three concentrations of EL4CM24 tested (FIG. 4). This in combination with the sequencing of a prominent doublet of protein bands from EL4 conditioned media, points to the presence of copious amounts of HSP90α/β as radicicol is a known inhibitor of HSP90. Although the overall level of migration of lymphocytes was reduced by the use of radicicol, the highest level of migration seen with radicicol treated EL4 conditioned media was still significant compared to media alone. This low level of inhibition may be a function of the concentration of radiciol used, or may indicate that HSP90 works in concert with some other fugetactic protein or proteins in the conditioned media to augment their effect.

The results using Geldanamycin treated EI4 24-hour conditioned media in the transmigration assays in response to the 1 in 100, 1 in 10, and 1 in 2 dilutions is also provided in FIG. 4.

Fractionation of EL4 Conditioned Media Reveals Candidate Proteins which Elicit Repulsion of Murine Lymphocytes Elution of fractions of 24-hour EL4 conditioned media from DEAE columns using 0.25M NaCl resulted in two fractions associated with the repulsion of murine lymphocytes when tested in transmigration assays. Sequencing of component proteins from the fractions with the highest activity identified demonstrated that the fugetactic activity was associated with the presence of a 65 kDa, 84 kDa, 86 kDa, 94 kDa and 110 kDa proteins in the EL4CM24. Results from the MS-Fit and MS-Tag searches are provided in FIGS. 12-14. Specifically, the results depicted in these figures provide the identity of the proteins (i.e., HSPs and L-plastin) that contained peptide sequences that are homologous to the component proteins from the EL4CM24 fractions.

EL4 CM Repels Immune Cells In Vivo

Figure 5:
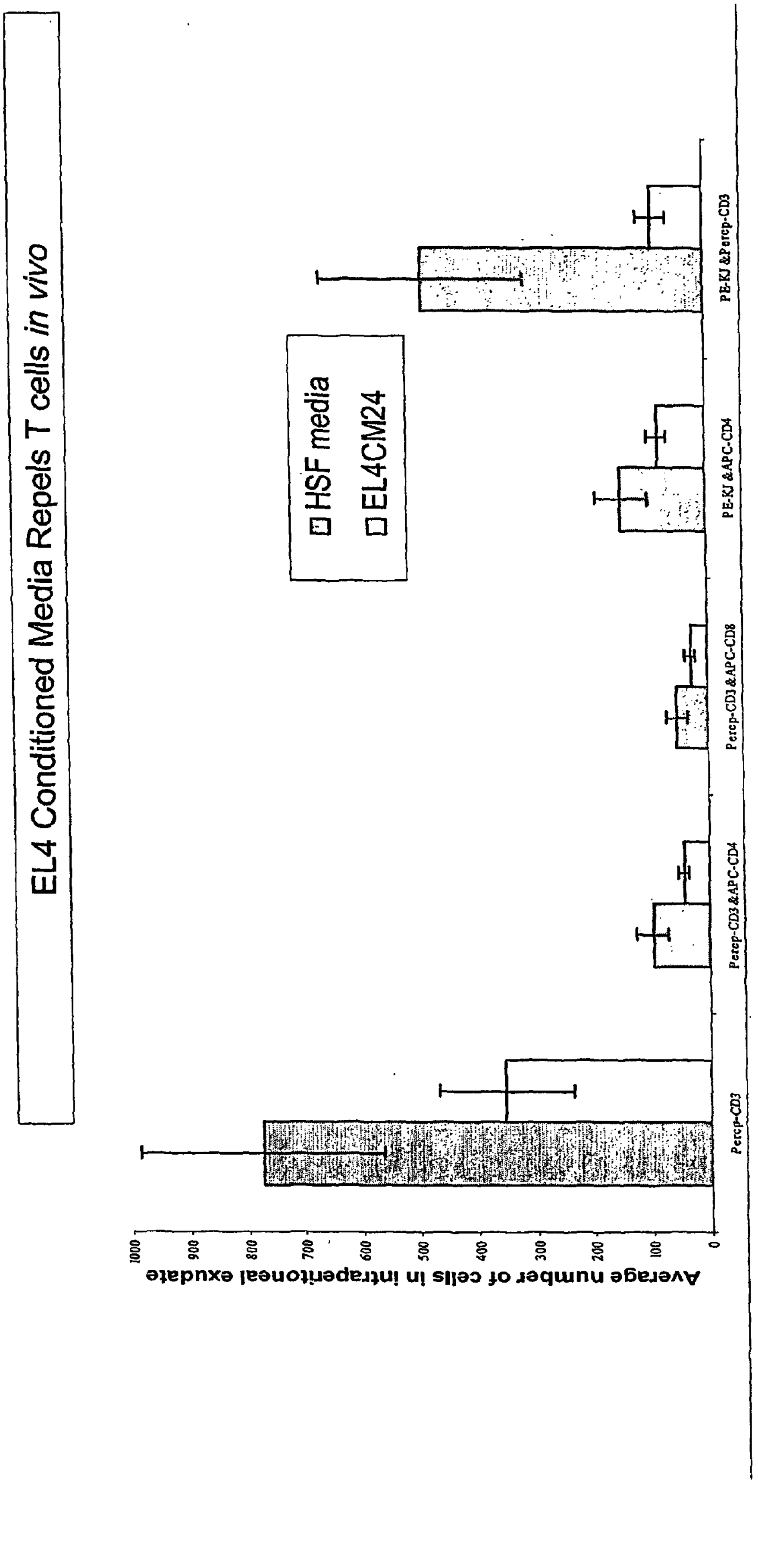
FIG. 5 provides the results of an in vivo study of the migration of immune cells using EL4 24-hour conditioned media (EL4CM24).
Figure 6:
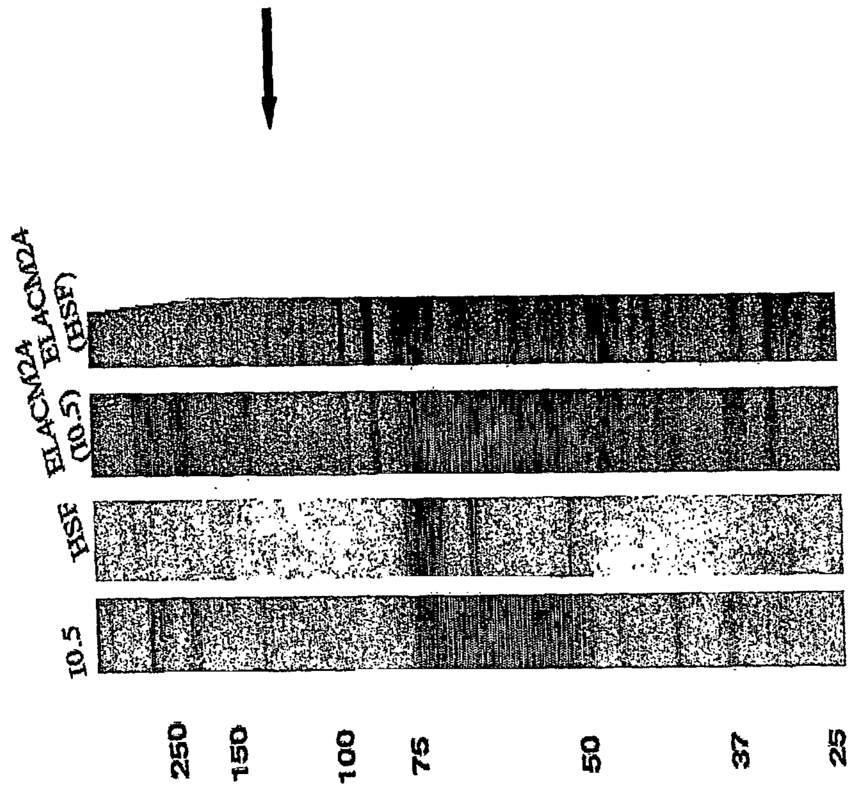
FIG. 6 provides the results of EL4 24-hour conditioned media (EL4CM24) (I0.5 and HSF) run on SDS PAGE.
Figure 7:
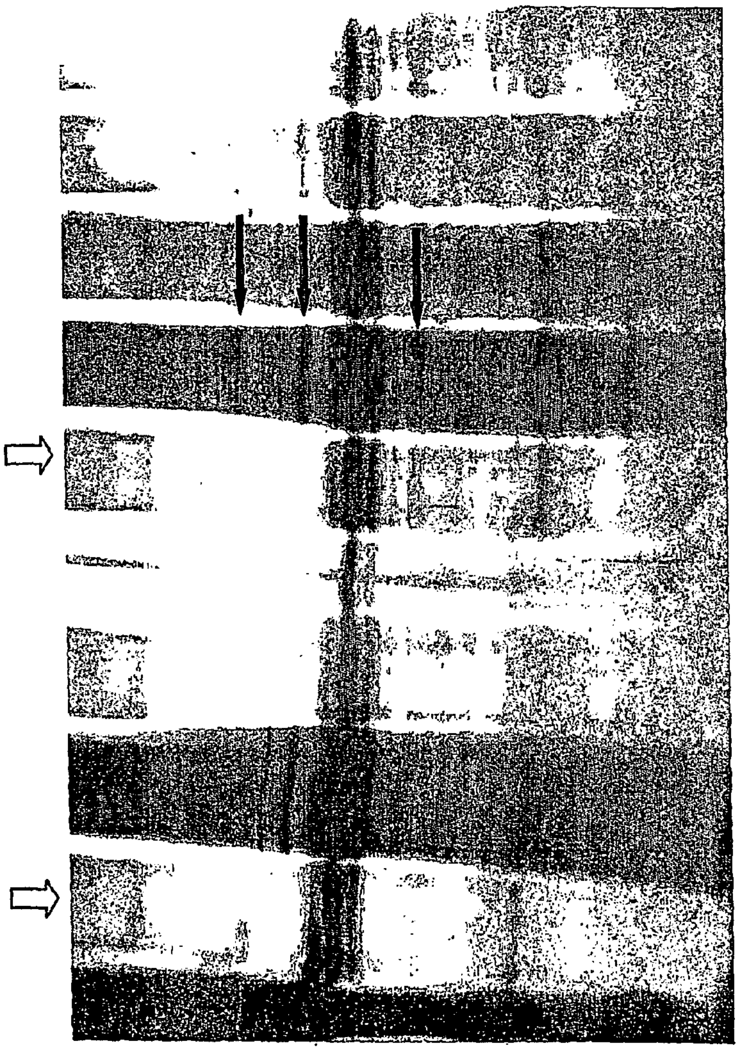
FIG. 7 provides the results of the ion exchange chromatography of the EL4 24-hour conditioned media (EL4CM24).

A T-cell infiltrate and subsequent allergic immune reaction was established in the intraperitoneal cavity of BALB/C DO11 mice using established techniques (3). EL4CM24, HSF or protease treated EL4CM24 was instilled into the inflamed peritoneal cavity to establish how these agents would affect T-cell infiltration into the anatomic space. EL4CM24 alone significantly reduced ($p<0.05$) the infiltration of all T-cell subtypes into the peritoneal cavity and in particular those T-cells bearing the OVA specific TCR (FIG. 5). Protease treated EL4CM24 and HSF alone did not have a significant effect on T-cell infiltration into the peritoneal cavity.

Immunoprecipitation of HSP90α from CM with a monoclonal antibody against the protein in conditioned medium from EL-4 cells led to a four-fold reduction in the fugetactic effect of the CM on T-cells infiltrating the peritoneal cavity following immune challenge in vivo.

EL4 CM Repels Immune Cells In Vivo

Although the fugetactic protein is likely a secreted protein, heat shock did not lead to its overexpression. In transmigration assays using negative gradients of heat shocked (at 42° C.) EL4 24-hour conditioned media, the level of migration of lymphocytes was not significantly increased by heat shock (FIG. 8).

Figure 8:
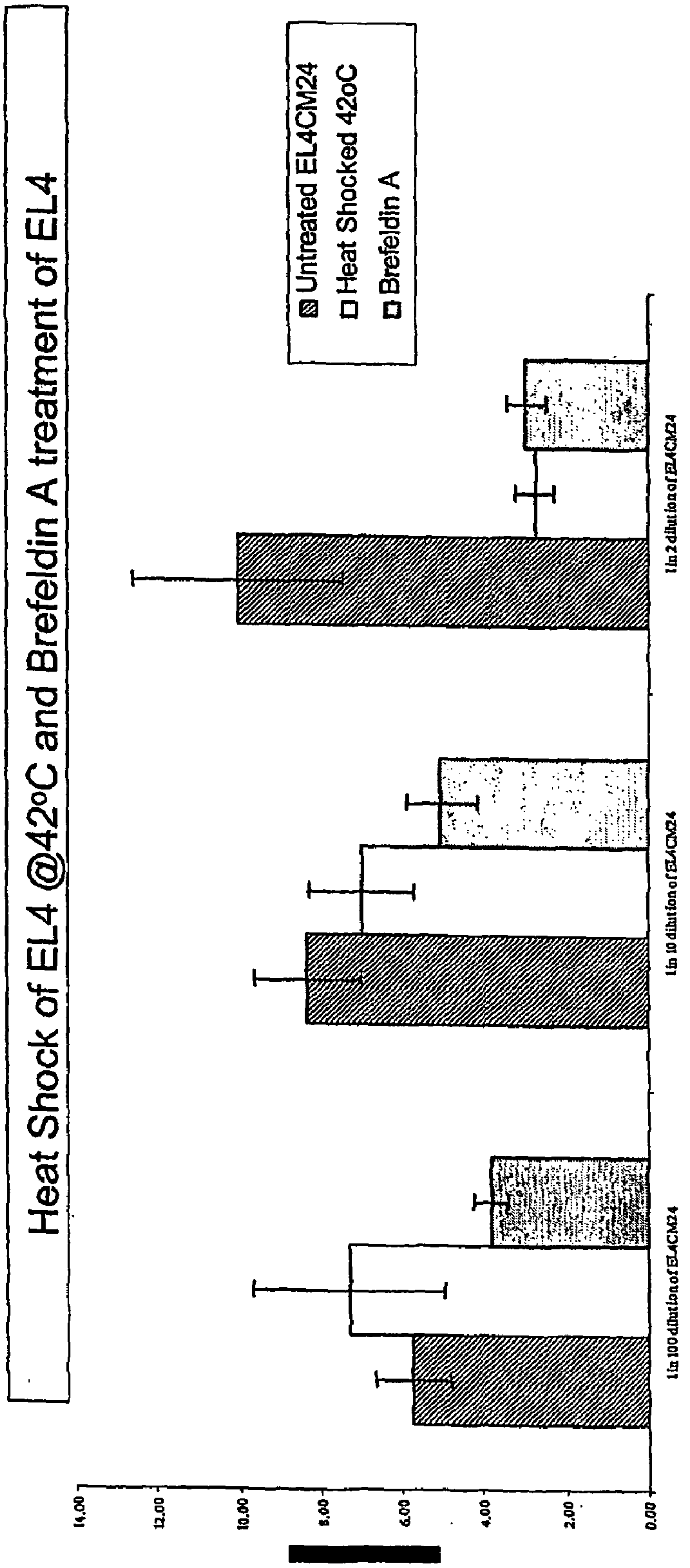
FIG. 8 provides the results of a transmigration assay using EL4 24-hour conditioned media (EL4CM24) heat shocked at 42° C. and treated with Brefeldin A.
Figure 9:
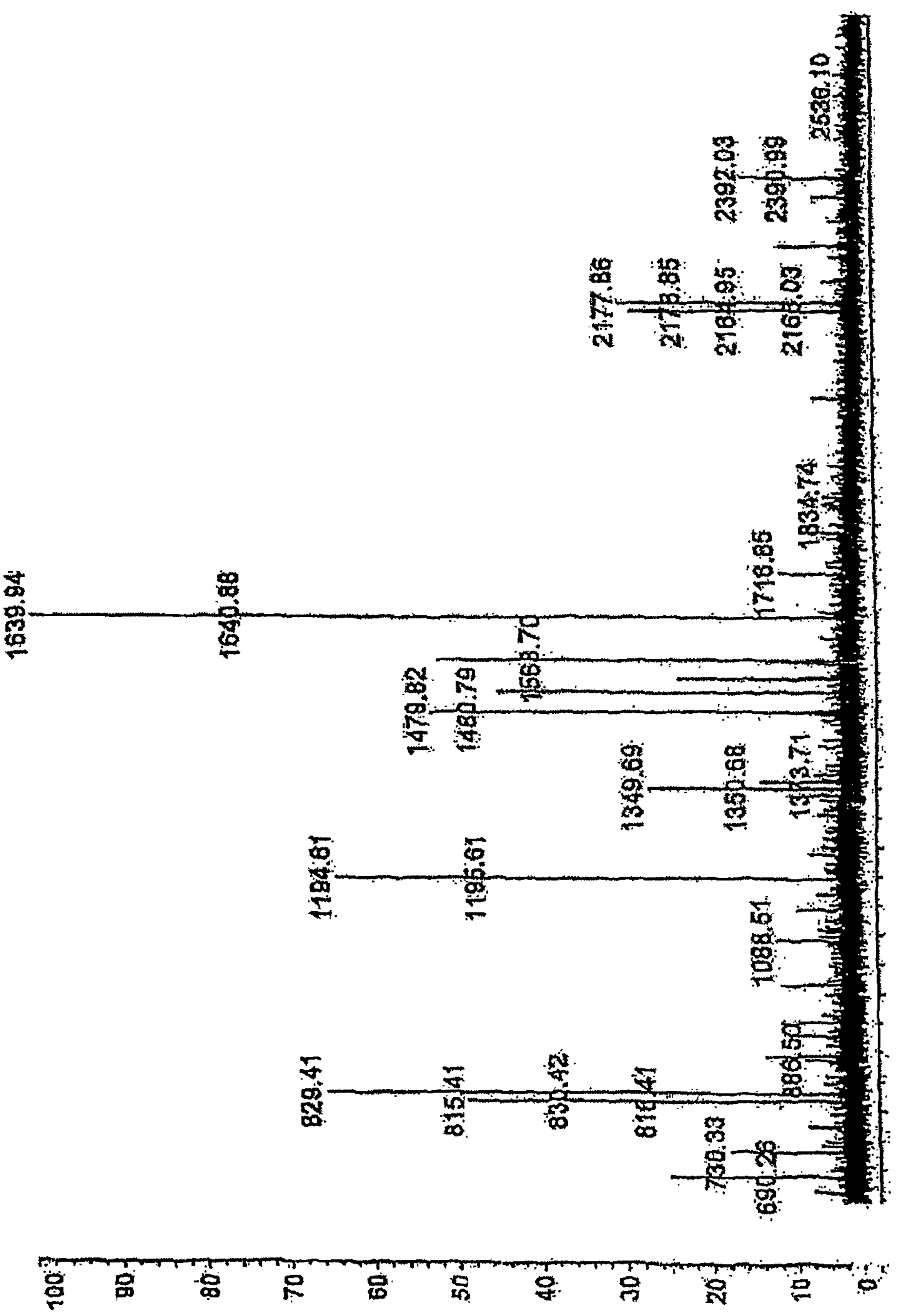
FIG. 9 provides the mass peaks from the mass spectrometry analysis of a fraction of EL4 24-hour conditioned media (EL4CM24) that contained a protein of about 84/86 kDa.
Figure 10:
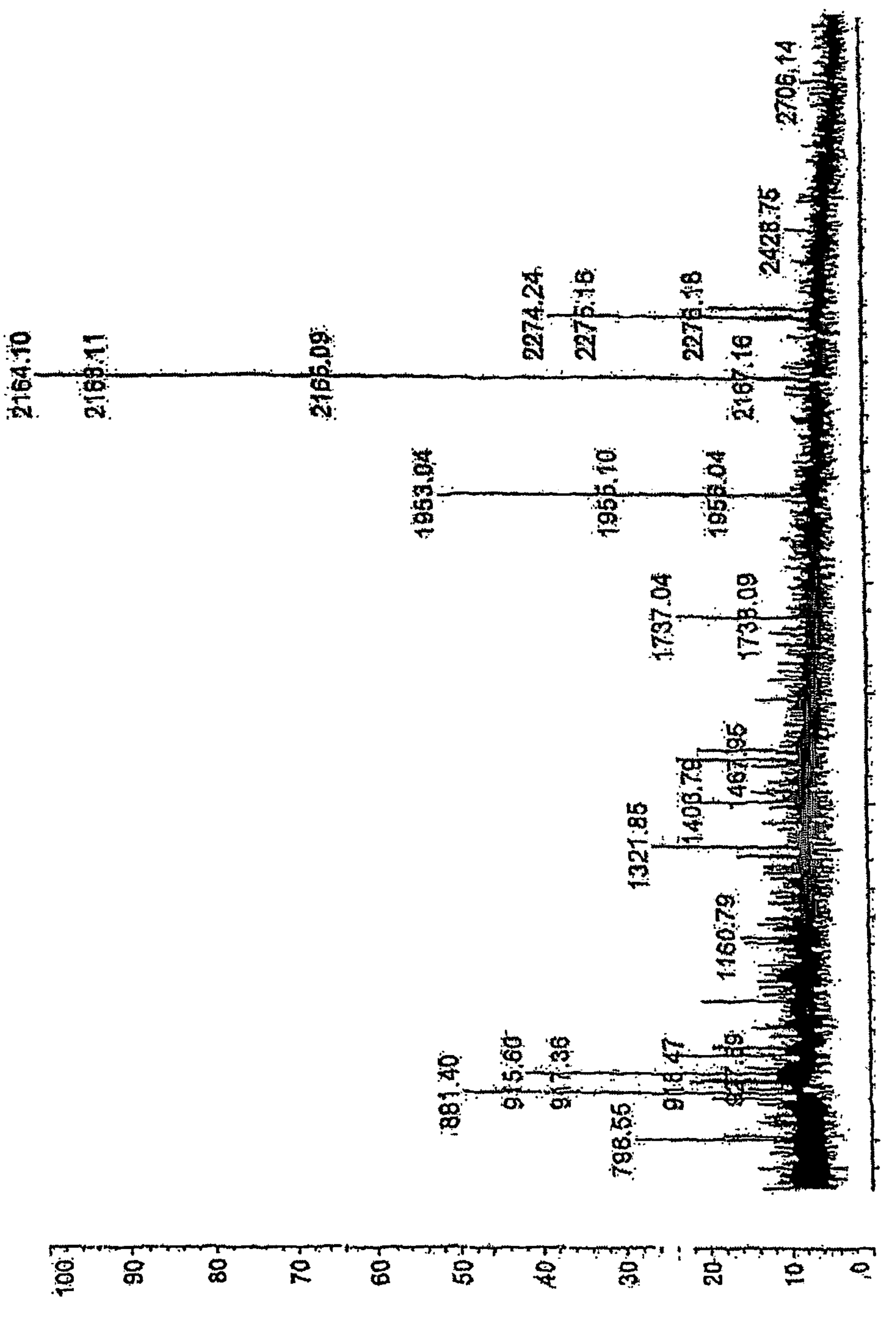
FIG. 10 provides the mass peaks from the mass spectrometry analysis of a fraction of EL4 24-hour conditioned media (EL4CM24) that contained a protein of about 94 kDa.
Figure 11:
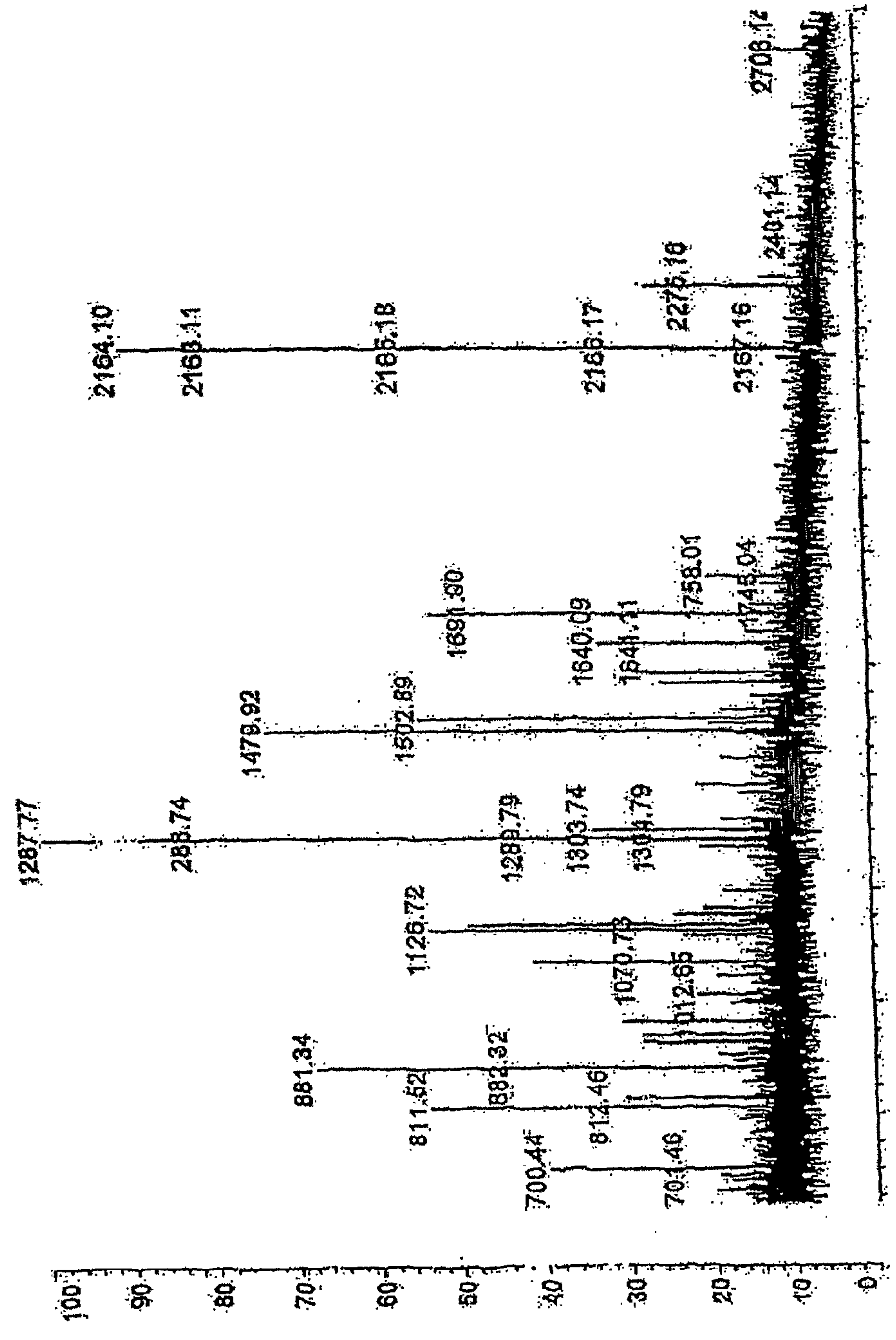
FIG. 11 provides the mass peaks from the mass spectrometry analysis of a fraction of EL4 24-hour conditioned media (EL4CM24) that contained a protein of about 65 kDa.

FIG. 8 also provides the results from the treatment of the EL4 24-hour conditioned media with Brefeldin A.

REFERENCES

1. Baggiolini, M., Chemokines and leukocyte traffic. Nature, 1998. 392(6676): p. 565-8.
2. Ward, S. G. and J. Westwick, Chemokines: understanding their role in T-lymphocyte biology. Biochem J, 1998. 333 (Pt 3): p. 457-70.
3. Poznansky, M. C., et al., Active movement of T cells away from a chemokine. Nat Med, 2000. 6(5): p. 543-8.
4. Poznansky, M. C., et al., Thymocyte emigration is mediated by active movement away from stroma-derived factors. J Clin Invest, 2002. 109(8): p. 1101-10.
5. Muller, A., et al., Involvement of chemokine receptors in breast cancer metastasis. Nature, 2001. 410(6824): p. 50-6.
6. Hasegawa, H., et al., Increased chemokine receptor CCR7/EBI1 expression enhances the infiltration of lymphoid organs by adult T-cell leukemia cells. Blood, 2000. 95(1): p. 30-8.
7. Nomura, T., et al., Enhancement of anti-tumor immunity by tumor cells transfected with the secondary lymphoid tissue chemokine EBI-1-ligand chemokine and stromal cell-derived factor-1alpha chemokine genes. Int J Cancer, 2001. 91(5): p. 597-606.
8. Guo, J., et al., Macrophage-derived chemokine gene transfer results in tumor regression in murine lung carcinoma model through efficient induction of antitumor immunity. Gene Ther, 2002. 9(12): p. 793-803.
9. Srivastava, P. K. and R. J. Amato, Heat shock proteins: the 'Swiss Army Knife' vaccines against cancers and infectious agents. Vaccine, 2001. 19(17-19): p. 2590-7.
10. Basu, S. and P. K. Srivastava, Heat shock proteins: the fountainhead of innate and adaptive immune responses. Cell Stress Chaperones, 2000. 5(5): p. 443-51.
11. Basu, S., et al., Necrotic but not apoptotic cell death releases heat shock proteins, which deliver a partial maturation signal to dendritic cells and activate the NF-kappa B pathway. Int Immunol, 2000. 12(11): p. 1539-46.
12. Basu, S., et al., CD91 is a common receptor for heat shock proteins gp96, hsp90, hsp70, and calreticulin. Immunity, 2001. 14(3): p. 303-13.
13. Weiss, Y. G., et al., Adenoviral transfer of HSP-70 into pulmonary epithelium ameliorates experimental acute respiratory distress syndrome. J Clin Invest, 2002. 110(6): p. 801-6.
14. Maccubbin, D. L., et al., Modification of host antitumor defense mechanisms in mice by progressively growing tumor. Cancer Res, 1989. 49(15): p. 4216-24.
15. Shrikant, P. and M. F. Mescher, Opposing effects of IL-2 in tumor immunotherapy: promoting CD8 T cell growth and inducing apoptosis. J Immunol, 2002. 169(4): p. 1753-9.
16. Shrikant, P. and M. F. Mescher, Control of syngeneic tumor growth by activation of CD8+ T cells: efficacy is limited by migration away from the site and induction of nonresponsiveness. J Immunol, 1999. 162(5): p. 2858-66.
17. Shrikant, P., A. Khoruts, and M. F. Mescher, CTLA-4 blockade reverses CD8+ T cell tolerance to tumor by a CD4+ T cell- and IL-2-dependent mechanism. Immunity, 1999. 11(4): p. 483-93.
18. Frevert, C. W., et al., Rapid fluorescence-based measurement of neutrophil migration in vitro. J Immunol Methods, 1998. 213(1): p. 41-52.

We claim:

1. A pharmaceutical composition comprising an isolated heat shock protein (HSP) consisting of SEQ ID NO: 47 in an effective amount to promote fugetactic activity and a pharmaceutically acceptable carrier.

2. A method of promoting fugetaxis of migratory cells in a subject, comprising: administering to a subject in need of such treatment the Heat Shock Protein (HSP) of SEQ ID NO:3 or a fragment thereof consisting of SEQ ID NO: 47, in an amount effective to promote fugetaxis of migratory cells away from a stent in a subject.

* * * * *

SEQUENCE LISTING

```
<160> NUMBER OF SEQ ID NOS: 121

<210> SEQ ID NO 1
<211> LENGTH: 724
<212> TYPE: PRT
<213> ORGANISM: Mus sp.

<400> SEQUENCE: 1

Met Pro Glu Glu Val His His Gly Glu Glu Glu Val Glu Thr Phe Ala
  1               5                  10                  15

Phe Gln Ala Glu Ile Ala Gln Leu Met Ser Leu Ile Ile Asn Thr Phe
             20                  25                  30
```

-continued

```
Tyr Ser Asn Lys Glu Ile Phe Leu Arg Glu Leu Ile Ser Asn Ala Ser
        35                  40                  45

Asp Ala Leu Asp Lys Ile Arg Tyr Glu Ser Leu Thr Asp Pro Ser Lys
    50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Glu Arg Glu Lys Glu
    210                 215                 220

Ile Ser Asp Asp Glu Ala Glu Glu Glu Lys Gly Glu Lys Glu Glu Glu
225                 230                 235                 240

Asp Lys Asp Asp Glu Glu Lys Pro Lys Ile Glu Asp Val Gly Ser Asp
                245                 250                 255

Glu Glu Asp Asp Ser Gly Lys Asp Lys Lys Lys Lys Thr Lys Lys Ile
            260                 265                 270

Lys Glu Lys Tyr Ile Asp Gln Glu Glu Leu Asn Lys Thr Lys Pro Ile
        275                 280                 285

Trp Thr Arg Asn Pro Asp Asp Ile Thr Gln Glu Glu Tyr Gly Glu Phe
    290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Lys Asn Asn
            340                 345                 350

Ile Lys Leu Tyr Val Arg Arg Val Phe Ile Met Asp Ser Cys Asp Glu
        355                 360                 365

Leu Ile Pro Glu Tyr Leu Asn Phe Ile Arg Gly Val Val Asp Ser Glu
    370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
                405                 410                 415

Ser Glu Leu Ala Glu Asp Lys Glu Asn Tyr Lys Lys Phe Tyr Glu Ala
            420                 425                 430

Phe Ser Lys Asn Leu Lys Leu Gly Ile His Glu Asp Ser Thr Asn Arg
        435                 440                 445

Arg Arg Leu Ser Glu Leu Leu Arg Tyr His Thr Ser Gln Ser Gly Asp
```

-continued

```
    450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
            500                 505                 510

Met Thr Glu Pro Ile Asp Glu Tyr Cys Val Gln Gln Leu Lys Glu Phe
        515                 520                 525

Asp Gly Lys Ser Leu Val Ser Val Thr Lys Glu Gly Leu Glu Leu Pro
    530                 535                 540

Glu Asp Glu Glu Glu Lys Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
            580                 585                 590

Thr Ser Thr Tyr Gly Trp Thr Ala Asn Met Glu Arg Ile Met Lys Ala
        595                 600                 605

Gln Ala Leu Arg Asp Asn Ser Thr Met Gly Tyr Met Met Ala Lys Lys
    610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
        675                 680                 685

Gly Ile Asp Glu Asp Glu Val Ala Ala Glu Glu Pro Asn Ala Ala Val
    690                 695                 700

Pro Asp Glu Ile Pro Pro Leu Glu Gly Asp Glu Asp Ala Ser Arg Met
705                 710                 715                 720

Glu Glu Val Asp


<210> SEQ ID NO 2
<211> LENGTH: 724
<212> TYPE: PRT
<213> ORGANISM: Homo sapiens

<400> SEQUENCE: 2

Met Pro Glu Glu Val His His Gly Glu Glu Glu Val Glu Thr Phe Ala
  1               5                  10                  15

Phe Gln Ala Glu Ile Ala Gln Leu Met Ser Leu Ile Ile Asn Thr Phe
             20                  25                  30

Tyr Ser Asn Lys Glu Ile Phe Leu Arg Glu Leu Ile Ser Asn Ala Ser
         35                  40                  45

Asp Ala Leu Asp Lys Ile Arg Tyr Glu Ser Leu Thr Asp Pro Ser Lys
     50                  55                  60

Leu Asp Ser Gly Lys Glu Leu Lys Ile Asp Ile Ile Pro Asn Pro Gln
 65                  70                  75                  80

Glu Arg Thr Leu Thr Leu Val Asp Thr Gly Ile Gly Met Thr Lys Ala
                 85                  90                  95

Asp Leu Ile Asn Asn Leu Gly Thr Ile Ala Lys Ser Gly Thr Lys Ala
```

-continued

```
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Glu Arg Glu Lys Glu
    210                 215                 220

Ile Ser Asp Asp Glu Ala Glu Glu Glu Lys Gly Glu Lys Glu Glu Glu
225                 230                 235                 240

Asp Lys Asp Asp Glu Glu Lys Pro Lys Ile Glu Asp Val Gly Ser Asp
                245                 250                 255

Glu Glu Asp Asp Ser Gly Lys Asp Lys Lys Lys Lys Thr Lys Lys Ile
            260                 265                 270

Lys Glu Lys Tyr Ile Asp Gln Glu Glu Leu Asn Lys Thr Lys Pro Ile
        275                 280                 285

Trp Thr Arg Asn Pro Asp Asp Ile Thr Gln Glu Glu Tyr Gly Glu Phe
    290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Lys Asn Asn
            340                 345                 350

Ile Lys Leu Tyr Val Arg Arg Val Phe Ile Met Asp Ser Cys Asp Glu
        355                 360                 365

Leu Ile Pro Glu Tyr Leu Asn Phe Ile Arg Gly Val Val Asp Ser Glu
    370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
                405                 410                 415

Ser Glu Leu Ala Glu Asp Lys Glu Asn Tyr Lys Lys Phe Tyr Glu Ala
            420                 425                 430

Phe Ser Lys Asn Leu Lys Leu Gly Ile His Glu Asp Ser Thr Asn Arg
        435                 440                 445

Arg Arg Leu Ser Glu Leu Leu Arg Tyr His Thr Ser Gln Ser Gly Asp
    450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
            500                 505                 510

Met Thr Glu Pro Ile Asp Glu Tyr Cys Val Gln Gln Leu Lys Glu Phe
        515                 520                 525
```

-continued

```
Asp Gly Lys Ser Leu Val Ser Val Thr Lys Glu Gly Leu Glu Leu Pro
    530                 535                 540

Glu Asp Glu Glu Glu Lys Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
            580                 585                 590

Thr Ser Thr Tyr Gly Trp Thr Ala Asn Met Glu Arg Ile Met Lys Ala
        595                 600                 605

Gln Ala Leu Arg Asp Asn Ser Thr Met Gly Tyr Met Met Ala Lys Lys
    610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
        675                 680                 685

Gly Ile Asp Glu Asp Glu Val Ala Ala Glu Glu Pro Asn Ala Ala Val
    690                 695                 700

Pro Asp Glu Ile Pro Pro Leu Glu Gly Asp Glu Asp Ala Ser Arg Met
705                 710                 715                 720

Glu Glu Val Asp


<210> SEQ ID NO 3
<211> LENGTH: 732
<212> TYPE: PRT
<213> ORGANISM: Homo sapiens

<400> SEQUENCE: 3

Met Pro Glu Glu Thr Gln Thr Gln Asp Gln Pro Met Glu Glu Glu Glu
  1               5                  10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Ser Leu
     50                  55                  60

Thr Asp Pro Ser Lys Leu Asp Ser Gly Lys Glu Leu His Ile Asn Leu
 65                  70                  75                  80

Ile Pro Asn Lys Gln Asp Arg Thr Leu Thr Ile Val Asp Thr Gly Ile
                 85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175
```

-continued

```
Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Glu Lys Lys Asp Gly
            260                 265                 270

Asp Lys Lys Lys Lys Lys Lys Ile Lys Glu Lys Tyr Ile Asp Gln Glu
        275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
            340                 345                 350

Glu Asn Arg Lys Lys Lys Asn Asn Ile Lys Leu Tyr Val Arg Arg Val
        355                 360                 365

Phe Ile Met Asp Asn Cys Glu Glu Leu Ile Pro Glu Tyr Leu Asn Phe
    370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
            420                 425                 430

Asn Tyr Lys Lys Phe Tyr Glu Gln Phe Ser Lys Asn Ile Lys Leu Gly
        435                 440                 445

Ile His Glu Asp Ser Gln Asn Arg Lys Lys Leu Ser Glu Leu Leu Arg
    450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
            500                 505                 510

Lys His Gly Leu Glu Val Ile Tyr Met Ile Glu Pro Ile Asp Glu Tyr
        515                 520                 525

Cys Val Gln Gln Leu Lys Glu Phe Glu Gly Lys Thr Leu Val Ser Val
    530                 535                 540

Thr Lys Glu Gly Leu Glu Leu Pro Glu Asp Glu Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Val Ser Asn Arg Leu
            580                 585                 590
```

-continued

```
Val Thr Ser Pro Cys Cys Ile Val Thr Ser Thr Tyr Gly Trp Thr Ala
        595                 600                 605

Asn Met Glu Arg Ile Met Lys Ala Gln Ala Leu Arg Asp Asn Ser Thr
    610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
        675                 680                 685

Tyr Arg Met Ile Lys Leu Gly Leu Gly Ile Asp Glu Asp Asp Pro Thr
    690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730


<210> SEQ ID NO 4
<211> LENGTH: 724
<212> TYPE: PRT
<213> ORGANISM: Mus sp.

<400> SEQUENCE: 4

Met Pro Glu Glu Val His His Gly Glu Glu Glu Val Glu Thr Phe Ala
  1               5                  10                  15

Phe Gln Ala Glu Ile Ala Gln Leu Met Ser Leu Ile Ile Asn Thr Phe
            20                  25                  30

Tyr Ser Asn Lys Glu Ile Phe Leu Arg Glu Leu Ile Ser Asn Ala Ser
        35                  40                  45

Asp Ala Leu Asp Lys Ile Arg Tyr Glu Ser Leu Thr Asp Pro Ser Lys
     50                  55                  60

Leu Asp Ser Gly Lys Glu Leu Lys Ile Asp Ile Ile Pro Asn Pro Gln
 65                  70                  75                  80

Glu Arg Thr Leu Thr Leu Val Asp Thr Gly Ile Gly Met Thr Lys Ala
                 85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Glu Arg Glu Lys Glu
    210                 215                 220

Ile Ser Asp Asp Glu Ala Glu Glu Glu Lys Gly Glu Lys Glu Glu Glu
225                 230                 235                 240
```

-continued

```
Asp Lys Glu Asp Glu Glu Lys Pro Lys Ile Glu Asp Val Gly Ser Asp
                245                 250                 255

Glu Glu Asp Asp Ser Gly Lys Asp Lys Lys Lys Lys Thr Lys Lys Ile
            260                 265                 270

Lys Glu Lys Tyr Ile Asp Gln Glu Glu Leu Asn Lys Thr Lys Pro Ile
        275                 280                 285

Trp Thr Arg Asn Pro Asp Asp Ile Thr Gln Glu Glu Tyr Gly Glu Phe
    290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Lys Asn Asn
            340                 345                 350

Ile Lys Leu Tyr Val Arg Arg Val Phe Ile Met Asp Ser Cys Asp Glu
        355                 360                 365

Leu Ile Pro Glu Tyr Leu Asn Phe Ile Arg Gly Val Val Asp Ser Glu
    370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
                405                 410                 415

Ser Glu Leu Ala Glu Asp Lys Glu Asn Tyr Lys Lys Phe Tyr Glu Ala
            420                 425                 430

Phe Ser Lys Asn Leu Lys Leu Gly Ile His Glu Asp Ser Thr Asn Arg
        435                 440                 445

Arg Arg Leu Ser Glu Leu Leu Arg Tyr His Thr Ser Gln Ser Gly Asp
    450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
            500                 505                 510

Met Thr Glu Pro Ile Asp Glu Tyr Cys Val Gln Gln Leu Lys Glu Phe
        515                 520                 525

Asp Gly Lys Ser Leu Val Ser Val Thr Lys Glu Gly Leu Glu Leu Pro
    530                 535                 540

Glu Asp Glu Glu Glu Lys Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
            580                 585                 590

Thr Ser Thr Tyr Gly Trp Thr Ala Asn Met Glu Arg Ile Met Lys Ala
        595                 600                 605

Gln Ala Leu Arg Asp Asn Ser Thr Met Gly Tyr Met Met Ala Lys Lys
    610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655
```

-continued

```
Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
        675                 680                 685

Gly Ile Asp Glu Asp Glu Val Thr Ala Glu Glu Pro Ser Ala Ala Val
    690                 695                 700

Pro Asp Glu Ile Pro Pro Leu Glu Gly Asp Glu Asp Ala Ser Arg Met
705                 710                 715                 720

Glu Glu Val Asp


<210> SEQ ID NO 5
<211> LENGTH: 724
<212> TYPE: PRT
<213> ORGANISM: Homo sapiens

<400> SEQUENCE: 5

Met Pro Glu Glu Val His His Gly Glu Glu Glu Val Glu Thr Phe Ala
  1               5                  10                  15

Phe Gln Ala Glu Ile Ala Gln Leu Met Ser Leu Ile Ile Asn Thr Phe
             20                  25                  30

Tyr Ser Asn Lys Glu Ile Phe Leu Arg Glu Leu Ile Ser Asn Ala Ser
         35                  40                  45

Asp Ala Leu Asp Lys Ile Arg Tyr Glu Ser Leu Thr Asp Pro Ser Lys
     50                  55                  60

Leu Asp Ser Gly Lys Glu Leu Lys Ile Asp Ile Ile Pro Asn Pro Gln
 65                  70                  75                  80

Glu Arg Thr Leu Thr Leu Val Asp Thr Gly Ile Gly Met Thr Lys Ala
                 85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Glu Arg Glu Lys Glu
    210                 215                 220

Ile Ser Asp Asp Glu Ala Glu Glu Glu Lys Gly Glu Lys Glu Glu Glu
225                 230                 235                 240

Asp Lys Asp Asp Glu Glu Lys Pro Lys Ile Glu Asp Val Gly Ser Asp
                245                 250                 255

Glu Glu Asp Asp Ser Gly Lys Asp Lys Lys Lys Lys Thr Lys Lys Ile
            260                 265                 270

Lys Glu Lys Tyr Ile Asp Gln Glu Glu Leu Asn Lys Thr Lys Pro Ile
        275                 280                 285

Trp Thr Arg Asn Pro Asp Asp Ile Thr Gln Glu Glu Tyr Gly Glu Phe
    290                 295                 300
```

-continued

```
Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Lys Asn Asn
            340                 345                 350

Ile Lys Leu Tyr Val Arg Arg Val Phe Ile Met Asp Ser Cys Asp Glu
        355                 360                 365

Leu Ile Pro Glu Tyr Leu Asn Phe Ile Arg Gly Val Val Asp Ser Glu
    370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
                405                 410                 415

Ser Glu Leu Ala Glu Asp Lys Glu Asn Tyr Lys Lys Phe Tyr Glu Ala
            420                 425                 430

Phe Ser Lys Asn Leu Lys Leu Gly Ile His Glu Asp Ser Thr Asn Arg
        435                 440                 445

Arg Arg Leu Ser Glu Leu Leu Arg Tyr His Thr Ser Gln Ser Gly Asp
    450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
            500                 505                 510

Met Thr Glu Pro Ile Asp Glu Tyr Cys Val Gln Gln Leu Lys Glu Phe
        515                 520                 525

Asp Gly Lys Ser Leu Val Ser Val Thr Lys Glu Gly Leu Glu Leu Pro
    530                 535                 540

Glu Asp Glu Glu Glu Lys Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
            580                 585                 590

Thr Ser Thr Tyr Gly Trp Thr Ala Asn Met Glu Arg Ile Met Lys Ala
        595                 600                 605

Gln Ala Leu Arg Asp Asn Ser Thr Met Gly Tyr Met Met Ala Lys Lys
    610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
        675                 680                 685

Gly Ile Asp Glu Asp Glu Val Ala Ala Glu Glu Pro Asn Ala Ala Val
    690                 695                 700

Pro Asp Glu Ile Pro Pro Leu Glu Gly Asp Glu Asp Ala Ser Arg Met
705                 710                 715                 720

Glu Glu Val Asp
```

<210> SEQ ID NO 6
<211> LENGTH: 733
<212> TYPE: PRT
<213> ORGANISM: Mus sp.

<400> SEQUENCE: 6

```
Met Pro Glu Glu Thr Gln Thr Gln Asp Gln Pro Met Glu Glu Glu Glu
  1               5                  10                  15

Val Glu Thr Phe Ala Phe Gln Ala Glu Ile Ala Gln Leu Met Ser Leu
             20                  25                  30

Ile Ile Asn Thr Phe Tyr Ser Asn Lys Glu Ile Phe Leu Arg Glu Leu
         35                  40                  45

Ile Ser Asn Ser Ser Asp Ala Leu Asp Lys Ile Arg Tyr Glu Ser Leu
     50                  55                  60

Thr Asp Pro Ser Lys Leu Asp Ser Gly Lys Glu Leu His Ile Asn Leu
 65                  70                  75                  80

Ile Pro Ser Lys Gln Asp Arg Thr Leu Thr Ile Val Asp Thr Gly Ile
                 85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Glu
225                 230                 235                 240

Lys Glu Glu Glu Lys Glu Lys Glu Glu Lys Glu Ser Asp Asp Lys Pro
                245                 250                 255

Glu Ile Glu Asp Val Gly Ser Asp Glu Glu Glu Glu Glu Lys Lys Asp
            260                 265                 270

Gly Asp Lys Lys Lys Lys Lys Lys Ile Lys Glu Lys Tyr Ile Asp Gln
        275                 280                 285

Glu Glu Leu Asn Lys Thr Lys Pro Ile Trp Thr Arg Asn Pro Asp Asp
    290                 295                 300

Ile Thr Asn Glu Glu Tyr Gly Glu Phe Tyr Lys Ser Leu Thr Asn Asp
305                 310                 315                 320

Trp Glu Glu His Leu Ala Val Lys His Phe Ser Val Glu Gly Gln Leu
                325                 330                 335

Glu Phe Arg Ala Leu Leu Phe Val Pro Arg Arg Ala Pro Phe Asp Leu
            340                 345                 350

Phe Glu Asn Arg Lys Lys Lys Asn Asn Ile Lys Leu Tyr Val Arg Arg
        355                 360                 365

Val Phe Ile Met Asp Asn Cys Glu Glu Leu Ile Pro Glu Tyr Leu Asn
```

-continued

```
    370                 375                 380

Phe Ile Arg Gly Val Val Asp Ser Glu Asp Leu Pro Leu Asn Ile Ser
385                 390                 395                 400

Arg Glu Met Leu Gln Gln Ser Lys Ile Leu Lys Val Ile Arg Lys Asn
                405                 410                 415

Leu Val Lys Lys Cys Leu Glu Leu Phe Thr Glu Leu Ala Glu Asp Lys
            420                 425                 430

Glu Asn Tyr Lys Lys Phe Tyr Glu Gln Phe Ser Lys Asn Ile Lys Leu
        435                 440                 445

Gly Ile His Glu Asp Ser Gln Asn Arg Lys Lys Leu Ser Glu Leu Leu
    450                 455                 460

Arg Tyr Tyr Thr Ser Ala Ser Gly Asp Glu Met Val Ser Leu Lys Asp
465                 470                 475                 480

Tyr Cys Thr Arg Met Lys Glu Asn Gln Lys His Ile Tyr Phe Ile Thr
                485                 490                 495

Gly Glu Thr Lys Asp Gln Val Ala Asn Ser Ala Phe Val Glu Arg Leu
            500                 505                 510

Arg Lys His Gly Leu Glu Val Ile Tyr Met Ile Glu Pro Ile Asp Glu
        515                 520                 525

Tyr Cys Val Gln Gln Leu Lys Glu Phe Glu Gly Lys Thr Leu Val Ser
    530                 535                 540

Val Thr Lys Glu Gly Leu Glu Leu Pro Glu Asp Glu Glu Glu Lys Lys
545                 550                 555                 560

Lys Gln Glu Glu Lys Lys Thr Lys Phe Glu Asn Leu Cys Lys Ile Met
                565                 570                 575

Lys Asp Ile Leu Glu Lys Lys Val Glu Lys Val Val Val Ser Asn Arg
            580                 585                 590

Leu Val Thr Ser Pro Cys Cys Ile Val Thr Ser Thr Tyr Gly Trp Thr
        595                 600                 605

Ala Asn Met Glu Arg Ile Met Lys Ala Gln Ala Leu Arg Asp Asn Ser
    610                 615                 620

Thr Met Gly Tyr Met Ala Ala Lys Lys His Leu Glu Ile Asn Pro Asp
625                 630                 635                 640

His Ser Ile Ile Glu Thr Leu Arg Gln Lys Ala Glu Ala Asp Lys Asn
                645                 650                 655

Asp Lys Ser Val Lys Asp Leu Val Ile Leu Leu Tyr Glu Thr Ala Leu
            660                 665                 670

Leu Ser Ser Gly Phe Ser Leu Glu Asp Pro Gln Thr His Ala Asn Arg
        675                 680                 685

Ile Tyr Arg Met Ile Lys Leu Gly Leu Gly Ile Asp Glu Asp Asp Pro
    690                 695                 700

Thr Val Asp Asp Thr Ser Ala Ala Val Thr Glu Glu Met Pro Pro Leu
705                 710                 715                 720

Glu Gly Asp Asp Asp Thr Ser Arg Met Glu Glu Val Asp
                725                 730


<210> SEQ ID NO 7
<211> LENGTH: 573
<212> TYPE: PRT
<213> ORGANISM: Homo sapiens

<400> SEQUENCE: 7

Met Leu Arg Leu Pro Thr Val Phe Arg Gln Met Arg Pro Val Ser Arg
  1               5                  10                  15
```

-continued

```
Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
```

-continued

```
        435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
        515                 520                 525

Leu Leu Asp Ala Ala Gly Val Ala Ser Leu Leu Thr Thr Ala Glu Val
    530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                565                 570


<210> SEQ ID NO 8
<211> LENGTH: 627
<212> TYPE: PRT
<213> ORGANISM: Homo sapiens

<400> SEQUENCE: 8

Met Ala Arg Gly Ser Val Ser Asp Glu Glu Met Met Glu Leu Arg Glu
  1               5                  10                  15

Ala Phe Ala Lys Val Asp Thr Asp Gly Asn Gly Tyr Ile Ser Phe Asn
            20                  25                  30

Glu Leu Asn Asp Leu Phe Lys Ala Ala Cys Leu Pro Leu Pro Gly Tyr
        35                  40                  45

Arg Val Arg Glu Ile Thr Glu Asn Leu Met Ala Thr Gly Asp Leu Asp
    50                  55                  60

Gln Asp Gly Arg Ile Ser Phe Asp Glu Phe Ile Lys Ile Phe His Gly
 65                  70                  75                  80

Leu Lys Ser Thr Asp Val Ala Lys Thr Phe Arg Lys Ala Ile Asn Lys
                85                  90                  95

Lys Glu Gly Ile Cys Ala Ile Gly Gly Thr Ser Glu Gln Ser Ser Val
            100                 105                 110

Gly Thr Gln His Ser Tyr Ser Glu Glu Glu Lys Tyr Ala Phe Val Asn
        115                 120                 125

Trp Ile Asn Lys Ala Leu Glu Asn Asp Pro Asp Cys Arg His Val Ile
    130                 135                 140

Pro Met Asn Pro Asn Thr Asn Asp Leu Phe Asn Ala Val Gly Asp Gly
145                 150                 155                 160

Ile Val Leu Cys Lys Met Ile Asn Leu Ser Val Pro Asp Thr Ile Asp
                165                 170                 175

Glu Arg Thr Ile Asn Lys Lys Lys Leu Thr Pro Phe Thr Ile Gln Glu
            180                 185                 190

Asn Leu Asn Leu Ala Leu Asn Ser Ala Ser Ala Ile Gly Cys His Val
        195                 200                 205

Val Asn Ile Gly Ala Glu Asp Leu Lys Glu Gly Lys Pro Tyr Leu Val
    210                 215                 220

Leu Gly Leu Leu Trp Gln Val Ile Lys Ile Gly Leu Phe Ala Asp Ile
225                 230                 235                 240
```

-continued

```
Glu Leu Ser Arg Asn Glu Ala Leu Ile Ala Leu Leu Arg Glu Gly Glu
                245                 250                 255

Ser Leu Glu Asp Leu Met Lys Leu Ser Pro Glu Glu Leu Leu Leu Arg
            260                 265                 270

Trp Ala Asn Tyr His Leu Glu Asn Ala Gly Cys Asn Lys Ile Gly Asn
        275                 280                 285

Phe Ser Thr Asp Ile Lys Asp Ser Lys Ala Tyr Tyr His Leu Leu Glu
    290                 295                 300

Gln Val Ala Pro Lys Gly Asp Glu Glu Gly Val Pro Ala Val Val Ile
305                 310                 315                 320

Asp Met Ser Gly Leu Arg Glu Lys Asp Asp Ile Gln Arg Ala Glu Cys
                325                 330                 335

Met Leu Gln Gln Ala Glu Arg Leu Gly Cys Arg Gln Phe Val Thr Ala
            340                 345                 350

Thr Asp Val Val Arg Gly Asn Pro Lys Leu Asn Leu Ala Phe Ile Ala
        355                 360                 365

Asn Leu Phe Asn Arg Tyr Pro Ala Leu His Lys Pro Glu Asn Gln Asp
    370                 375                 380

Ile Asp Trp Gly Ala Leu Glu Gly Glu Thr Arg Glu Glu Arg Thr Phe
385                 390                 395                 400

Arg Asn Trp Met Asn Ser Leu Gly Val Asn Pro Arg Val Asn His Leu
                405                 410                 415

Tyr Ser Asp Leu Ser Asp Ala Leu Val Ile Phe Gln Leu Tyr Glu Lys
            420                 425                 430

Ile Lys Val Pro Val Asp Trp Asn Arg Val Asn Lys Pro Pro Tyr Pro
        435                 440                 445

Lys Leu Gly Gly Asn Met Lys Lys Leu Glu Asn Cys Asn Tyr Ala Val
    450                 455                 460

Glu Leu Gly Lys Asn Gln Ala Lys Phe Ser Leu Val Gly Ile Gly Gly
465                 470                 475                 480

Gln Asp Leu Asn Glu Gly Asn Arg Thr Leu Thr Leu Ala Leu Ile Trp
                485                 490                 495

Gln Leu Met Arg Arg Tyr Thr Leu Asn Ile Leu Glu Glu Ile Gly Gly
            500                 505                 510

Gly Gln Lys Val Asn Asp Asp Ile Ile Val Asn Trp Val Asn Glu Thr
        515                 520                 525

Leu Arg Glu Ala Glu Lys Ser Ser Ser Ile Ser Ser Phe Lys Asp Pro
    530                 535                 540

Lys Ile Ser Thr Ser Leu Pro Val Leu Asp Leu Ile Asp Ala Ile Gln
545                 550                 555                 560

Pro Gly Ser Ile Asn Tyr Asp Leu Leu Lys Thr Glu Asn Leu Asn Asp
                565                 570                 575

Asp Glu Lys Leu Asn Asn Ala Lys Tyr Ala Ile Ser Met Ala Arg Lys
            580                 585                 590

Ile Gly Ala Arg Val Tyr Ala Leu Pro Glu Asp Leu Val Glu Val Asn
        595                 600                 605

Pro Lys Met Val Met Thr Val Phe Ala Cys Leu Met Gly Lys Gly Met
    610                 615                 620

Lys Arg Val
625
```

<210> SEQ ID NO 9
<211> LENGTH: 8
<212> TYPE: PRT

-continued

<213> ORGANISM: Equus caballus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present

<400> SEQUENCE: 9

Lys Val Thr Ile Ser Asn Arg Leu
1 5

<210> SEQ ID NO 10
<211> LENGTH: 9
<212> TYPE: PRT
<213> ORGANISM: Equus caballus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 10

Arg Ala Leu Leu Phe Ile Pro Arg Arg
1 5

<210> SEQ ID NO 11
<211> LENGTH: 9
<212> TYPE: PRT
<213> ORGANISM: Equus caballus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 11

Lys Phe Tyr Glu Ala Phe Ser Lys Asn
1 5

<210> SEQ ID NO 12
<211> LENGTH: 12
<212> TYPE: PRT
<213> ORGANISM: Equus caballus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 12

Lys Ile Asp Ile Ile Pro Asn Pro Gln Glu Arg Thr
1 5 10

<210> SEQ ID NO 13
<211> LENGTH: 13
<212> TYPE: PRT
<213> ORGANISM: Equus caballus
<220> FEATURE:
<221> NAME/KEY: MOD_RES -continued

```
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 13

Lys His Phe Ser Val Glu Gly Gln Leu Glu Phe Arg Ala
  1               5                  10


<210> SEQ ID NO 14
<211> LENGTH: 16
<212> TYPE: PRT
<213> ORGANISM: Equus caballus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 14

Arg Gly Val Val Asp Ser Glu Asp Leu Pro Leu Asn Ile Ser Arg Glu
  1               5                  10                  15


<210> SEQ ID NO 15
<211> LENGTH: 21
<212> TYPE: PRT
<213> ORGANISM: Equus caballus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (21)
<223> OTHER INFORMATION: May or may not be present

<400> SEQUENCE: 15

Arg Tyr His Thr Ser Gln Ser Gly Asp Glu Met Thr Ser Leu Ser Glu
  1               5                  10                  15

Tyr Val Ser Arg Met
             20


<210> SEQ ID NO 16
<211> LENGTH: 23
<212> TYPE: PRT
<213> ORGANISM: Equus caballus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (23)
<223> OTHER INFORMATION: May or may not be present

<400> SEQUENCE: 16

Lys Ser Ile Tyr Tyr Ile Thr Gly Glu Ser Lys Glu Gln Val Ala Asn
  1               5                  10                  15

Ser Ala Phe Val Glu Arg Val
             20


<210> SEQ ID NO 17
<211> LENGTH: 8
<212> TYPE: PRT
```

-continued

<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present

<400> SEQUENCE: 17

Lys Val Thr Ile Ser Asn Arg Leu
1 5

<210> SEQ ID NO 18
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 18

Arg Ala Leu Leu Phe Ile Pro Arg Arg
1 5

<210> SEQ ID NO 19
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 19

Lys Phe Tyr Glu Ala Phe Ser Lys Asn
1 5

<210> SEQ ID NO 20
<211> LENGTH: 12
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 20

Lys Ile Asp Ile Ile Pro Asn Pro Gln Glu Arg Thr
1 5 10

<210> SEQ ID NO 21
<211> LENGTH: 13
<212> TYPE: PRT
<213> ORGANISM: Homo sapiens
<220> FEATURE:
<221> NAME/KEY: MOD_RES -continued
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 21

Lys His Phe Ser Val Glu Gly Gln Leu Glu Phe Arg Ala
1 5 10

<210> SEQ ID NO 22
<211> LENGTH: 16
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 22

Arg Gly Val Val Asp Ser Glu Asp Leu Pro Leu Asn Ile Ser Arg Glu
1 5 10 15

<210> SEQ ID NO 23
<211> LENGTH: 21
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (21)
<223> OTHER INFORMATION: May or may not be present

<400> SEQUENCE: 23

Arg Tyr His Thr Ser Gln Ser Gly Asp Glu Met Thr Ser Leu Ser Glu
1 5 10 15

Tyr Val Ser Arg Met
20

<210> SEQ ID NO 24
<211> LENGTH: 23
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (23)
<223> OTHER INFORMATION: May or may not be present

<400> SEQUENCE: 24

Lys Ser Ile Tyr Tyr Ile Thr Gly Glu Ser Lys Glu Gln Val Ala Asn
1 5 10 15

Ser Ala Phe Val Glu Arg Val
20

<210> SEQ ID NO 25
<211> LENGTH: 8
<212> TYPE: PRT

-continued

<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present

<400> SEQUENCE: 25

Lys Val Thr Ile Ser Asn Arg Leu
1 5

<210> SEQ ID NO 26
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 26

Arg Ala Leu Leu Phe Val Pro Arg Arg
1 5

<210> SEQ ID NO 27
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 27

Lys Phe Tyr Glu Ala Phe Ser Lys Asn
1 5

<210> SEQ ID NO 28
<211> LENGTH: 12
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 28

Lys Ile Asp Ile Leu Pro Asn Pro Gln Glu Arg Thr
1 5 10

<210> SEQ ID NO 29
<211> LENGTH: 13
<212> TYPE: PRT
<213> ORGANISM: Homo sapiens
<220> FEATURE:
<221> NAME/KEY: MOD_RES -continued
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 29

Lys His Glu Ser Val Glu Gly Gln Leu Glu Phe Arg Ala
1 5 10

<210> SEQ ID NO 30
<211> LENGTH: 16
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 30

Arg Gly Val Val Asp Ser Glu Asp Leu Pro Leu Asn Ile Ser Arg Glu
1 5 10 15

<210> SEQ ID NO 31
<211> LENGTH: 21
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (21)
<223> OTHER INFORMATION: May or may not be present

<400> SEQUENCE: 31

Arg Tyr His Thr Ser Gln Ser Gly Asp Glu Met Thr Ser Leu Ser Glu
1 5 10 15

Tyr Val Ser Arg Met
20

<210> SEQ ID NO 32
<211> LENGTH: 23
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (23)
<223> OTHER INFORMATION: May or may not be present

<400> SEQUENCE: 32

Lys Ser Ile Tyr Tyr Ile Thr Gly Glu Ser Lys Glu Gln Val Ala Asn
1 5 10 15

Ser Ala Phe Val Glu Arg Val
20

<210> SEQ ID NO 33
<211> LENGTH: 8
<212> TYPE: PRT

-continued

```
<213> ORGANISM: Rattus sp.
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present

<400> SEQUENCE: 33

Lys Val Thr Ile Ser Asn Arg Leu
  1               5


<210> SEQ ID NO 34
<211> LENGTH: 9
<212> TYPE: PRT
<213> ORGANISM: Rattus sp.
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 34

Arg Ala Leu Leu Phe Ile Pro Arg Arg
  1               5


<210> SEQ ID NO 35
<211> LENGTH: 9
<212> TYPE: PRT
<213> ORGANISM: Rattus sp.
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 35

Lys Phe Tyr Glu Ala Phe Ser Lys Asn
  1               5


<210> SEQ ID NO 36
<211> LENGTH: 13
<212> TYPE: PRT
<213> ORGANISM: Rattus sp.
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 36

Lys His Phe Ser Val Glu Gly Gln Leu Glu Phe Arg Ala
  1               5                  10


<210> SEQ ID NO 37
<211> LENGTH: 16
<212> TYPE: PRT
<213> ORGANISM: Rattus sp.
<220> FEATURE:
<221> NAME/KEY: MOD_RES
```

-continued

<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 37

Arg Gly Val Val Asp Ser Glu Asp Leu Pro Leu Asn Ile Ser Arg Glu
1               5                   10                  15

<210> SEQ ID NO 38
<211> LENGTH: 21
<212> TYPE: PRT
<213> ORGANISM: Rattus sp.
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (21)
<223> OTHER INFORMATION: May or may not be present

<400> SEQUENCE: 38

Arg Tyr Met Thr Ser Gln Ser Gly Asp Glu Met Thr Ser Leu Ser Glu
1               5                   10                  15

Tyr Val Ser Arg Met
            20

<210> SEQ ID NO 39
<211> LENGTH: 23
<212> TYPE: PRT
<213> ORGANISM: Rattus sp.
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (23)
<223> OTHER INFORMATION: May or may not be present

<400> SEQUENCE: 39

Lys Ser Ile Tyr Tyr Ile Thr Gly Glu Ser Lys Glu Gln Val Ala Asn
1               5                   10                  15

Ser Ala Phe Val Glu Arg Val
            20

<210> SEQ ID NO 40
<211> LENGTH: 12
<212> TYPE: PRT
<213> ORGANISM: Mus sp.
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 40

Lys Ile Asp Ile Leu Pro Asn Pro Gln Glu Arg Thr
1               5                   10

<210> SEQ ID NO 41
<211> LENGTH: 12
<212> TYPE: PRT

-continued

<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 41

Lys Ile Asp Ile Leu Pro Asn Pro Gln Glu Arg Thr
1 5 10

<210> SEQ ID NO 42
<211> LENGTH: 12
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 42

Lys Ile Asp Ile Ile Pro Asn Pro Gln Glu Arg Thr
1 5 10

<210> SEQ ID NO 43
<211> LENGTH: 12
<212> TYPE: PRT
<213> ORGANISM: Mus sp.
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 43

Lys Ile Asp Ile Leu Pro Asn Pro Gln Glu Arg Thr
1 5 10

<210> SEQ ID NO 44
<211> LENGTH: 12
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 44

Lys Ile Asp Ile Leu Pro Asn Pro Gln Glu Arg Thr
1 5 10

<210> SEQ ID NO 45
<211> LENGTH: 12
<212> TYPE: PRT
<213> ORGANISM: Homo sapiens
<220> FEATURE:
<221> NAME/KEY: MOD_RES -continued
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 45

Lys Ile Asp Ile Ile Pro Asn Pro Gln Glu Arg Thr
1 5 10

<210> SEQ ID NO 46
<211> LENGTH: 9
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 46

Arg Ala Leu Leu Phe Val Pro Arg Arg
1 5

<210> SEQ ID NO 47
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 47

Arg Ala Leu Leu Phe Tyr Pro Arg Arg
1 5

<210> SEQ ID NO 48
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 48

Lys Ala Ile Leu Phe Val Pro Arg Arg
1 5

<210> SEQ ID NO 49
<211> LENGTH: 9
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:

-continued

```
<221> NAME/KEY: MOD_RES
<222> LOCATION: (9)
<223> OTHER INFORMATION: May or may not be present

<400> SEQUENCE: 49

Arg Ala Leu Leu Phe Val Pro Arg Arg
  1               5


<210> SEQ ID NO 50
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 50

Arg Ala Leu Leu Phe Val Pro Arg Arg
  1               5


<210> SEQ ID NO 51
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 51

Lys Ala Ile Leu Phe Val Pro Arg Arg
  1               5


<210> SEQ ID NO 52
<211> LENGTH: 8
<212> TYPE: PRT
<213> ORGANISM: Rattus norvegicus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present

<400> SEQUENCE: 52

Lys Val Leu Thr Phe Tyr Arg Lys
  1               5


<210> SEQ ID NO 53
<211> LENGTH: 10
<212> TYPE: PRT
<213> ORGANISM: Rattus norvegicus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (10)
<223> OTHER INFORMATION: May or may not be present
```

-continued

<400> SEQUENCE: 53

Lys Asn Thr Val Gln Gly Phe Lys Arg Phe
1 5 10

<210> SEQ ID NO 54
<211> LENGTH: 15
<212> TYPE: PRT
<213> ORGANISM: Rattus norvegicus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (15)
<223> OTHER INFORMATION: May or may not be present

<400> SEQUENCE: 54

Lys Val Leu Ala Thr Ala Phe Asp Thr Thr Leu Gly Gly Arg Lys
1 5 10 15

<210> SEQ ID NO 55
<211> LENGTH: 13
<212> TYPE: PRT
<213> ORGANISM: Rattus norvegicus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 55

Lys Asn Ala Val Glu Glu Tyr Val Tyr Glu Met Arg Asp
1 5 10

<210> SEQ ID NO 56
<211> LENGTH: 16
<212> TYPE: PRT
<213> ORGANISM: Rattus norvegicus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 56

Arg Ala Gly Gly Ile Glu Thr Ile Ala Asn Glu Tyr Ser Asp Arg Cys
1 5 10 15

<210> SEQ ID NO 57
<211> LENGTH: 17
<212> TYPE: PRT
<213> ORGANISM: Rattus norvegicus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (17)
<223> OTHER INFORMATION: May or may not be present

<400> SEQUENCE: 57

-continued

```
Arg Glu Phe Ser Ile Thr Asp Val Val Pro Tyr Pro Ile Ser Leu Arg
 1               5                  10                  15

Trp


<210> SEQ ID NO 58
<211> LENGTH: 19
<212> TYPE: PRT
<213> ORGANISM: Rattus norvegicus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (19)
<223> OTHER INFORMATION: May or may not be present

<400> SEQUENCE: 58

Arg Trp Asn Ser Pro Ala Glu Glu Gly Ser Ser Asp Cys Glu Val Phe
 1               5                  10                  15

Pro Lys Asn


<210> SEQ ID NO 59
<211> LENGTH: 8
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present

<400> SEQUENCE: 59

Lys Val Leu Thr Phe Tyr Arg Lys
 1               5


<210> SEQ ID NO 60
<211> LENGTH: 10
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (10)
<223> OTHER INFORMATION: May or may not be present

<400> SEQUENCE: 60

Lys Asn Thr Val Gln Gly Phe Lys Arg Phe
 1               5                  10


<210> SEQ ID NO 61
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 61
```

-continued

```
Lys Gln Val Tyr Val Asp Lys Leu Ala Glu Leu Lys Ser
  1               5                  10


<210> SEQ ID NO 62
<211> LENGTH: 15
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (15)
<223> OTHER INFORMATION: May or may not be present

<400> SEQUENCE: 62

Lys Val Leu Ala Thr Ala Phe Asp Thr Thr Leu Gly Gly Arg Lys
  1               5                  10                  15


<210> SEQ ID NO 63
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 63

Lys Asn Ala Val Glu Glu Tyr Val Tyr Glu Met Arg Asp
  1               5                  10


<210> SEQ ID NO 64
<211> LENGTH: 16
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 64

Arg Ala Gly Gly Ile Glu Thr Ile Ala Asn Glu Tyr Ser Asp Arg Cys
  1               5                  10                  15


<210> SEQ ID NO 65
<211> LENGTH: 17
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (17)
<223> OTHER INFORMATION: May or may not be present

<400> SEQUENCE: 65

Arg Glu Phe Ser Ile Thr Asp Val Val Pro Tyr Pro Ile Ser Leu Arg
  1               5                  10                  15
```

-continued

Trp

<210> SEQ ID NO 66
<211> LENGTH: 8
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present

<400> SEQUENCE: 66

Lys Val Leu Thr Phe Tyr Arg Lys
1 5

<210> SEQ ID NO 67
<211> LENGTH: 10
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (10)
<223> OTHER INFORMATION: May or may not be present

<400> SEQUENCE: 67

Lys Asn Thr Val Gln Gly Phe Lys Arg Phe
1 5 10

<210> SEQ ID NO 68
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 68

Lys Gln Val Tyr Val Asp Lys Leu Ala Glu Leu Lys Ser
1 5 10

<210> SEQ ID NO 69
<211> LENGTH: 15
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (15)
<223> OTHER INFORMATION: May or may not be present

<400> SEQUENCE: 69

Lys Val Leu Ala Thr Ala Phe Asp Thr Thr Ile Gly Gly Arg Lys
1 5 10 15

<210> SEQ ID NO 70
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 70

Lys Asn Ala Val Glu Glu Tyr Val Tyr Glu Met Arg Asp
1 5 10

<210> SEQ ID NO 71
<211> LENGTH: 16
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 71

Arg Ala Gly Gly Ile Glu Thr Ile Ala Asn Glu Tyr Ser Asp Arg Cys
1 5 10 15

<210> SEQ ID NO 72
<211> LENGTH: 17
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (17)
<223> OTHER INFORMATION: May or may not be present

<400> SEQUENCE: 72

Arg Glu Phe Ser Ile Thr Asp Val Val Pro Tyr Pro Ile Ser Leu Arg
1 5 10 15

Trp

<210> SEQ ID NO 73

<400> SEQUENCE: 73

000

<210> SEQ ID NO 74
<211> LENGTH: 8
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present -continued

<400> SEQUENCE: 74

Lys Val Phe His Gly Leu Lys Ser
1 5

<210> SEQ ID NO 75
<211> LENGTH: 9
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 75

Lys Tyr Ala Ile Ser Met Ala Arg Lys
1 5

<210> SEQ ID NO 76
<211> LENGTH: 10
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (10)
<223> OTHER INFORMATION: May or may not be present

<400> SEQUENCE: 76

Arg Val Asn Lys Pro Pro Val Pro Lys Leu
1 5 10

<210> SEQ ID NO 77
<211> LENGTH: 11
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (11)
<223> OTHER INFORMATION: May or may not be present

<400> SEQUENCE: 77

Lys Leu Ser Pro Glu Glu Leu Leu Leu Arg Trp
1 5 10

<210> SEQ ID NO 78
<211> LENGTH: 11
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (11)
<223> OTHER INFORMATION: May or may not be present

<400> SEQUENCE: 78

-continued

```
Lys Ile Lys Val Pro Val Asp Trp Asn Arg Val
  1               5                  10


<210> SEQ ID NO 79
<211> LENGTH: 12
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 79

Arg Gln Phe Val Thr Ala Thr Asp Val Val Arg Gly
  1               5                  10


<210> SEQ ID NO 80
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 80

Arg Asn Trp Met Asn Ser Leu Gly Val Asn Pro Arg Val
  1               5                  10


<210> SEQ ID NO 81
<211> LENGTH: 15
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (15)
<223> OTHER INFORMATION: May or may not be present

<400> SEQUENCE: 81

Lys Met Ile Asn Leu Ser Val Pro Asp Thr Ile Asp Glu Arg Thr
  1               5                  10                  15


<210> SEQ ID NO 82
<211> LENGTH: 16
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 82

Arg Val Tyr Ala Leu Pro Glu Asp Leu Val Glu Val Asn Pro Lys Met
  1               5                  10                  15
```

-continued

<210> SEQ ID NO 83
<211> LENGTH: 18
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (18)
<223> OTHER INFORMATION: May or may not be present

<400> SEQUENCE: 83

Lys Phe Ser Leu Val Gly Ile Ala Gly Gln Asp Leu Asn Glu Gly Asn
1 5 10 15

Arg Thr

<210> SEQ ID NO 84
<211> LENGTH: 19
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (19)
<223> OTHER INFORMATION: May or may not be present

<400> SEQUENCE: 84

Lys Gly Asp Glu Glu Gly Ile Pro Ala Val Val Ile Asp Met Ser Gly
1 5 10 15

Leu Arg Glu

<210> SEQ ID NO 85
<211> LENGTH: 8
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present

<400> SEQUENCE: 85

Lys Val Phe His Gly Leu Lys Ser
1 5

<210> SEQ ID NO 86
<211> LENGTH: 9
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 86

Lys Tyr Ala Ile Ser Met Ala Arg Lys
1 5

-continued

<210> SEQ ID NO 87
<211> LENGTH: 10
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (10)
<223> OTHER INFORMATION: May or may not be present

<400> SEQUENCE: 87

```
Arg Val Asn Lys Pro Pro Tyr Pro Lys Leu
  1               5                  10
```

<210> SEQ ID NO 88
<211> LENGTH: 11
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (11)
<223> OTHER INFORMATION: May or may not be present

<400> SEQUENCE: 88

```
Lys Leu Ser Pro Glu Glu Leu Leu Leu Arg Trp
  1               5                  10
```

<210> SEQ ID NO 89
<211> LENGTH: 11
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (11)
<223> OTHER INFORMATION: May or may not be present

<400> SEQUENCE: 89

```
Lys Ile Lys Val Pro Val Asp Trp Met Arg Val
  1               5                  10
```

<210> SEQ ID NO 90
<211> LENGTH: 12
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 90

```
Arg Gln Phe Val Thr Ala Thr Asp Val Val Arg Gly
  1               5                  10
```

<210> SEQ ID NO 91

-continued

<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 91

Arg Asn Trp Met Asn Ser Leu Gly Val Asn Pro Arg Val
1 5 10

<210> SEQ ID NO 92

<400> SEQUENCE: 92

000

<210> SEQ ID NO 93
<211> LENGTH: 15
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (15)
<223> OTHER INFORMATION: May or may not be present

<400> SEQUENCE: 93

Lys Met Ile Asn Leu Ser Val Pro Asp Thr Ile Asp Glu Arg Thr
1 5 10 15

<210> SEQ ID NO 94
<211> LENGTH: 16
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 94

Arg Val Tyr Ala Leu Pro Glu Asp Leu Val Glu Val Asn Pro Lys Met
1 5 10 15

<210> SEQ ID NO 95
<211> LENGTH: 18
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (18)
<223> OTHER INFORMATION: May or may not be present

<400> SEQUENCE: 95

Lys Glu Ser Leu Val Gly Ile Ala Gly Gln Asp Leu Asn Glu Gly Asn

-continued 1 5 10 15

Arg Thr

<210> SEQ ID NO 96
<211> LENGTH: 19
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (19)
<223> OTHER INFORMATION: May or may not be present

<400> SEQUENCE: 96

Lys Gly Asp Glu Glu Gly Ile Pro Ala Val Val Ile Asp Met Ser Gly
1 5 10 15

Leu Arg Glu

<210> SEQ ID NO 97
<211> LENGTH: 8
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (8)
<223> OTHER INFORMATION: May or may not be present

<400> SEQUENCE: 97

Lys Val Phe His Gly Leu Lys Thr
1 5

<210> SEQ ID NO 98
<211> LENGTH: 9
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (9)
<223> OTHER INFORMATION: May or may not be present

<400> SEQUENCE: 98

Lys Tyr Ala Ile Ser Met Ala Arg Lys
1 5

<210> SEQ ID NO 99
<211> LENGTH: 10
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (10)
<223> OTHER INFORMATION: May or may not be present

<400> SEQUENCE: 99

-continued

```
Arg Val Asn Lys Pro Pro Tyr Pro Lys Leu
  1               5                  10


<210> SEQ ID NO 100
<211> LENGTH: 11
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (11)
<223> OTHER INFORMATION: May or may not be present

<400> SEQUENCE: 100

Lys Leu Ser Pro Glu Glu Leu Leu Leu Arg Trp
  1               5                  10


<210> SEQ ID NO 101
<211> LENGTH: 11
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (11)
<223> OTHER INFORMATION: May or may not be present

<400> SEQUENCE: 101

Lys Ile Lys Val Pro Val Asp Trp Asn Arg Val
  1               5                  10


<210> SEQ ID NO 102
<211> LENGTH: 12
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (12)
<223> OTHER INFORMATION: May or may not be present

<400> SEQUENCE: 102

Arg Gln Phe Val Thr Ala Thr Asp Val Val Arg Gly
  1               5                  10


<210> SEQ ID NO 103
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 103

Arg Asn Trp Met Asn Ser Leu Gly Val Asn Pro Arg Val
  1               5                  10
```

-continued

<210> SEQ ID NO 104
<211> LENGTH: 15
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (15)
<223> OTHER INFORMATION: May or may not be present

<400> SEQUENCE: 104

```
Lys Met Ile Asn Leu Ser Val Pro Asp Thr Ile Asp Glu Arg Thr
  1               5                  10                  15
```

<210> SEQ ID NO 105
<211> LENGTH: 16
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (16)
<223> OTHER INFORMATION: May or may not be present

<400> SEQUENCE: 105

```
Arg Val Tyr Ala Leu Pro Glu Asp Leu Val Glu Val Asn Pro Lys Met
  1               5                  10                  15
```

<210> SEQ ID NO 106
<211> LENGTH: 19
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (19)
<223> OTHER INFORMATION: May or may not be present

<400> SEQUENCE: 106

```
Lys Gly Asp Glu Glu Gly Ile Pro Ala Val Val Ile Asp Met Ser Gly
  1               5                  10                  15

Leu Arg Glu
```

<210> SEQ ID NO 107
<211> LENGTH: 13
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 107

```
Arg Asn Trp Met Asn Ser Leu Gly Val Asn Pro Arg Val
  1               5                  10
```

-continued

<210> SEQ ID NO 108
<211> LENGTH: 13
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 108

Arg Asn Trp Met Asn Ser Leu Gly Val Asn Pro Arg Val
1 5 10

<210> SEQ ID NO 109
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 109

Arg Asn Trp Met Asn Ser Leu Gly Val Asn Pro Arg Val
1 5 10

<210> SEQ ID NO 110
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 110

Arg Asn Trp Met Asn Ser Leu Gly Val Asn Pro Arg Val
1 5 10

<210> SEQ ID NO 111
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 111

Arg Asn Trp Met Asn Ser Leu Gly Val Asn Pro Arg Val
1 5 10

<210> SEQ ID NO 112
<211> LENGTH: 13
<212> TYPE: PRT

-continued

```
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 112

Arg Asn Trp Met Asn Ser Leu Gly Val Asn Pro Arg Val
  1               5                   10


<210> SEQ ID NO 113
<211> LENGTH: 13
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 113

Arg Asn Trp Met Asn Ser Leu Gly Val Asn Pro Arg Val
  1               5                   10


<210> SEQ ID NO 114
<211> LENGTH: 13
<212> TYPE: PRT
<213> ORGANISM: Homo sapiens
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 114

Arg Asn Trp Met Asn Ser Leu Gly Val Asn Pro Arg Val
  1               5                   10


<210> SEQ ID NO 115
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 115

Arg Asn Trp Met Asn Ser Leu Gly Val Asn Pro Arg Val
  1               5                   10


<210> SEQ ID NO 116
<211> LENGTH: 13
<212> TYPE: PRT
<213> ORGANISM: Mus musculus
<220> FEATURE:
<221> NAME/KEY: MOD_RES
```

-continued

```
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 116

Arg Asn Trp Met Asn Ser Leu Gly Val Asn Pro Arg Val
  1               5                  10


<210> SEQ ID NO 117
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 117

Arg Asn Trp Met Asn Ser Leu Gly Val Asn Pro Arg Val
  1               5                  10


<210> SEQ ID NO 118
<211> LENGTH: 13
<212> TYPE: PRT
<213> ORGANISM: Mus musculus
<220> FEATURE:
<221> NAME/KEY: MOD_RES
<222> LOCATION: (1)
<223> OTHER INFORMATION: May or may not be present
<220> FEATURE:
<221> NAME/KEY: MOD_RES
<222> LOCATION: (13)
<223> OTHER INFORMATION: May or may not be present

<400> SEQUENCE: 118

Arg Asn Trp Met Asn Ser Leu Gly Val Asn Pro Arg Val
  1               5                  10


<210> SEQ ID NO 119
<211> LENGTH: 724
<212> TYPE: PRT
<213> ORGANISM: Homo sapiens
<220> FEATURE:
<221> NAME/KEY: MOD_RES
<222> LOCATION: (3)..(13)
<223> OTHER INFORMATION: Variable amino acid
<220> FEATURE:
<221> NAME/KEY: MOD_RES
<222> LOCATION: (220)..(275)
<223> OTHER INFORMATION: Variable amino acid
<220> FEATURE:
<221> NAME/KEY: MOD_RES
<222> LOCATION: (538)..(561)
<223> OTHER INFORMATION: Variable amino acid
<220> FEATURE:
<221> NAME/KEY: MOD_RES
<222> LOCATION: (691)..(707)
<223> OTHER INFORMATION: Variable amino acid

<400> SEQUENCE: 119

Met Pro Xaa Xaa Xaa Xaa Xaa Xaa Xaa Xaa Xaa Xaa Xaa Thr Phe Ala
  1               5                  10                  15

Phe Gln Ala Glu Ile Ala Gln Leu Met Ser Leu Ile Ile Asn Thr Phe
             20                  25                  30
```

-continued

```
Tyr Ser Asn Lys Glu Ile Phe Leu Arg Glu Leu Ile Ser Asn Ala Ser
        35                  40                  45

Asp Ala Leu Asp Lys Ile Arg Tyr Glu Ser Leu Thr Asp Pro Ser Lys
    50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Tyr Ile Asp Gln Glu Glu Leu Asn Lys Thr Lys Pro Ile
        275                 280                 285

Trp Thr Arg Asn Pro Asp Asp Ile Thr Gln Glu Glu Tyr Gly Glu Phe
    290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Lys Asn Asn
            340                 345                 350

Ile Lys Leu Tyr Val Arg Arg Val Phe Ile Met Asp Ser Cys Asp Glu
        355                 360                 365

Leu Ile Pro Glu Tyr Leu Asn Phe Ile Arg Gly Val Val Asp Ser Glu
    370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
                405                 410                 415

Ser Glu Leu Ala Glu Asp Lys Glu Asn Tyr Lys Lys Phe Tyr Glu Ala
            420                 425                 430

Phe Ser Lys Asn Leu Lys Leu Gly Ile His Glu Asp Ser Thr Asn Arg
        435                 440                 445
```

-continued

```
Arg Arg Leu Ser Glu Leu Leu Arg Tyr His Thr Ser Gln Ser Gly Asp
    450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
            500                 505                 510

Met Thr Glu Pro Ile Asp Glu Tyr Cys Val Gln Gln Leu Lys Glu Phe
        515                 520                 525

Asp Gly Lys Ser Leu Val Ser Val Thr Xaa Xaa Xaa Xaa Xaa Xaa Xaa
    530                 535                 540

Xaa Xaa Xaa Xaa Xaa Xaa Xaa Xaa Xaa Xaa Xaa Xaa Xaa Xaa Xaa Xaa
545                 550                 555                 560

Xaa Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
            580                 585                 590

Thr Ser Thr Tyr Gly Trp Thr Ala Asn Met Glu Arg Ile Met Lys Ala
        595                 600                 605

Gln Ala Leu Arg Asp Asn Ser Thr Met Gly Tyr Met Met Ala Lys Lys
    610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
        675                 680                 685

Gly Ile Xaa Xaa Xaa Xaa Xaa Xaa Xaa Xaa Xaa Xaa Xaa Xaa Xaa Xaa
    690                 695                 700

Xaa Xaa Xaa Ile Pro Pro Leu Glu Gly Asp Glu Asp Ala Ser Arg Met
705                 710                 715                 720

Glu Glu Val Asp


<210> SEQ ID NO 120
<211> LENGTH: 733
<212> TYPE: PRT
<213> ORGANISM: Mus sp.
<220> FEATURE:
<221> NAME/KEY: MOD_RES
<222> LOCATION: (227)..(290)
<223> OTHER INFORMATION: Variable amino acid
<220> FEATURE:
<221> NAME/KEY: MOD_RES
<222> LOCATION: (547)..(570)
<223> OTHER INFORMATION: Variable amino acid

<400> SEQUENCE: 120

Met Pro Glu Glu Thr Gln Thr Gln Asp Gln Pro Met Glu Glu Glu Glu
  1               5                  10                  15

Val Glu Thr Phe Ala Phe Gln Ala Glu Ile Ala Gln Leu Met Ser Leu
             20                  25                  30

Ile Ile Asn Thr Phe Tyr Ser Asn Lys Glu Ile Phe Leu Arg Glu Leu
         35                  40                  45

Ile Ser Asn Ser Ser Asp Ala Leu Asp Lys Ile Arg Tyr Glu Ser Leu
```

-continued

```
     50                  55                  60

Thr Asp Pro Ser Lys Leu Asp Ser Gly Lys Glu Leu His Ile Asn Leu
 65                  70                  75                  80

Ile Pro Ser Lys Gln Asp Arg Thr Leu Thr Ile Val Asp Thr Gly Ile
                 85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Leu Asn Lys Thr Lys Pro Ile Trp Thr Arg Asn Pro Asp Asp
    290                 295                 300

Ile Thr Asn Glu Glu Tyr Gly Glu Phe Tyr Lys Ser Leu Thr Asn Asp
305                 310                 315                 320

Trp Glu Glu His Leu Ala Val Lys His Phe Ser Val Glu Gly Gln Leu
                325                 330                 335

Glu Phe Arg Ala Leu Leu Phe Val Pro Arg Arg Ala Pro Phe Asp Leu
            340                 345                 350

Phe Glu Asn Arg Lys Lys Lys Asn Asn Ile Lys Leu Tyr Val Arg Arg
        355                 360                 365

Val Phe Ile Met Asp Asn Cys Glu Glu Leu Ile Pro Glu Tyr Leu Asn
    370                 375                 380

Phe Ile Arg Gly Val Val Asp Ser Glu Asp Leu Pro Leu Asn Ile Ser
385                 390                 395                 400

Arg Glu Met Leu Gln Gln Ser Lys Ile Leu Lys Val Ile Arg Lys Asn
                405                 410                 415

Leu Val Lys Lys Cys Leu Glu Leu Phe Thr Glu Leu Ala Glu Asp Lys
            420                 425                 430

Glu Asn Tyr Lys Lys Phe Tyr Glu Gln Phe Ser Lys Asn Ile Lys Leu
        435                 440                 445

Gly Ile His Glu Asp Ser Gln Asn Arg Lys Lys Leu Ser Glu Leu Leu
    450                 455                 460

Arg Tyr Tyr Thr Ser Ala Ser Gly Asp Glu Met Val Ser Leu Lys Asp
465                 470                 475                 480
```

-continued

```
Tyr Cys Thr Arg Met Lys Glu Asn Gln Lys His Ile Tyr Phe Ile Thr
                485                 490                 495

Gly Glu Thr Lys Asp Gln Val Ala Asn Ser Ala Phe Val Glu Arg Leu
            500                 505                 510

Arg Lys His Cys Leu Glu Val Ile Tyr Met Ile Glu Pro Ile Asp Glu
        515                 520                 525

Tyr Cys Val Gln Gln Leu Lys Glu Phe Glu Gly Lys Thr Leu Val Ser
    530                 535                 540

Val Thr Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Asn Leu Cys Lys Ile Met
                565                 570                 575

Lys Asp Ile Leu Glu Lys Lys Val Glu Lys Val Val Val Ser Asn Arg
            580                 585                 590

Leu Val Thr Ser Pro Cys Cys Ile Val Thr Ser Thr Tyr Gly Trp Thr
        595                 600                 605

Ala Asn Met Glu Arg Ile Met Lys Ala Gln Ala Leu Arg Asp Asn Ser
    610                 615                 620

Thr Met Gly Tyr Met Ala Ala Lys Lys His Leu Glu Ile Asn Pro Asp
625                 630                 635                 640

His Ser Ile Ile Glu Thr Leu Arg Gln Lys Ala Glu Ala Asp Lys Asn
                645                 650                 655

Asp Lys Ser Val Lys Asp Leu Val Ile Leu Leu Tyr Glu Thr Ala Leu
            660                 665                 670

Leu Ser Ser Gly Phe Ser Leu Glu Asp Pro Gln Thr His Ala Asn Arg
        675                 680                 685

Ile Tyr Arg Met Ile Lys Leu Gly Leu Gly Ile Asp Glu Asp Asp Pro
    690                 695                 700

Thr Val Asp Asp Thr Ser Ala Ala Val Thr Glu Glu Met Pro Pro Leu
705                 710                 715                 720

Glu Gly Asp Asp Asp Thr Ser Arg Met Glu Glu Val Asp
                725                 730


<210> SEQ ID NO 121
<211> LENGTH: 9
<212> TYPE: PRT
<213> ORGANISM: Unknown Organism
<220> FEATURE:
<223> OTHER INFORMATION: Description of Unknown Organism: Hypothetical
      peptide

<400> SEQUENCE: 121

Ala Lys Pro Val Leu Glu Asp Leu Arg
  1               5
```